(12) United States Patent
Cui et al.

(10) Patent No.: US 9,738,904 B2
(45) Date of Patent: Aug. 22, 2017

(54) INSECT RESISTANT AND HERBICIDE TOLERANT BREEDING STACK OF SOYBEAN EVENT PDAB9582.814.19.1 AND PDAB4468.04.16.1

(75) Inventors: Yunxing C. Cui, Carmel, IN (US); Thomas Hoffman, Zionsville, IN (US); Dawn M. Parkhurst, Avon, IN (US); Ning Zhou, Zionsville, IN (US); Barry Wiggins, Westfield, IN (US); Dayakar Pareddy, Carmel, IN (US); Gregory A. Bradfisch, Carmel, IN (US); James E. Dripps, Carmel (IN); Sandra G. Toledo, West Lafayette, IN (US); Nathan Bard, Edgerton, WI (US); Michael Vercauteren, Lafayette, IN (US); Nandi Nagaraj, Indianapolis, IN (US); Brandon Bishop, Whitestown, IN (US); Gregory J. Gilles, Alpharetta, GA (US); Terry R. Wright, Carmel, IN (US); Julissa Colon, West Lafayette, IN (US); Ricardo A. Barnes, Ponce, PR (US); Nathan J. VanOpdorp, Geneseo, IL (US); Yonghe Bai, Westfield, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 701 days.

(21) Appl. No.: 14/234,923

(22) PCT Filed: Jul. 26, 2012

(86) PCT No.: PCT/US2012/048302
§ 371 (c)(1),
(2), (4) Date: Aug. 7, 2014

(87) PCT Pub. No.: WO2013/016516
PCT Pub. Date: Jan. 31, 2013

(65) Prior Publication Data
US 2014/0344994 A1    Nov. 20, 2014

Related U.S. Application Data

(60) Provisional application No. 61/521,798, filed on Aug. 10, 2011, provisional application No. 61/511,664, filed on Jul. 26, 2011.

(51) Int. Cl.
| | |
|---|---|
| *A01H 1/00* | (2006.01) |
| *A01H 5/00* | (2006.01) |
| *A01H 5/10* | (2006.01) |
| *C12N 5/04* | (2006.01) |
| *C07H 21/04* | (2006.01) |
| *C12N 15/82* | (2006.01) |
| *C12Q 1/68* | (2006.01) |
| *A01N 37/38* | (2006.01) |
| *A01N 37/44* | (2006.01) |
| *A01N 65/20* | (2009.01) |

(52) U.S. Cl.
CPC ......... *C12N 15/8286* (2013.01); *A01N 37/38* (2013.01); *A01N 37/44* (2013.01); *A01N 65/20* (2013.01); *C12N 15/8209* (2013.01); *C12N 15/8274* (2013.01); *C12N 15/8277* (2013.01); *C12Q 1/6895* (2013.01); *C12Q 2600/13* (2013.01)

(58) Field of Classification Search
None
See application file for complete search history.

(56) References Cited

U.S. PATENT DOCUMENTS

| | | | |
|---|---|---|---|
| 4,808,426 A * | 2/1989 | Strop | C11B 1/00 426/417 |
| 2001/0026940 A1 | 10/2001 | Cardineau et al. | |
| 2004/0031072 A1 | 2/2004 | La Rosa et al. | |
| 2007/0044171 A1 | 2/2007 | Kovalic et al. | |
| 2007/0271630 A1 | 11/2007 | Boukharov et al. | |
| 2009/0191636 A1 | 7/2009 | Ramage et al. | |

FOREIGN PATENT DOCUMENTS

| | | |
|---|---|---|
| WO | WO2007053482 A2 | 5/2007 |
| WO | WO2008141154 A2 | 11/2008 |
| WO | WO2011066384 A1 | 6/2011 |

OTHER PUBLICATIONS deMaagd et al, Trends in Genetics (2001) 17:193-199.*
Walker et al, J. Econ. Entomol. (2000) 93:613-622.*
Hohe et al, Plant Cell Rep. (2003) 21:1135-1142.*
International Search Report dated Oct. 24, 2012 from related International Application No. PCT/US2012/048302.

* cited by examiner

*Primary Examiner* — Mykola V Kovalenko
(74) *Attorney, Agent, or Firm* — James Daly, IV; Barnes & Thornburg LLP

(57) ABSTRACT

A breeding stack of soybean event 9582.814.19.1 and soybean event pDAB4468.04.16.1 resulted in the novel soybean event pDAB9582.814.19.1::pDAB4468.04.16.1. Soybean event pDAB9582.814.19.1::pDAB4468.04.16.1 comprises genes encoding AAD-12, Cry1F, Cry1Ac (synpro), and PAT, affording insect resistance and herbicide tolerance to soybean crops containing the event, and enabling methods for crop protection and protection of stored products.

13 Claims, 3 Drawing Sheets

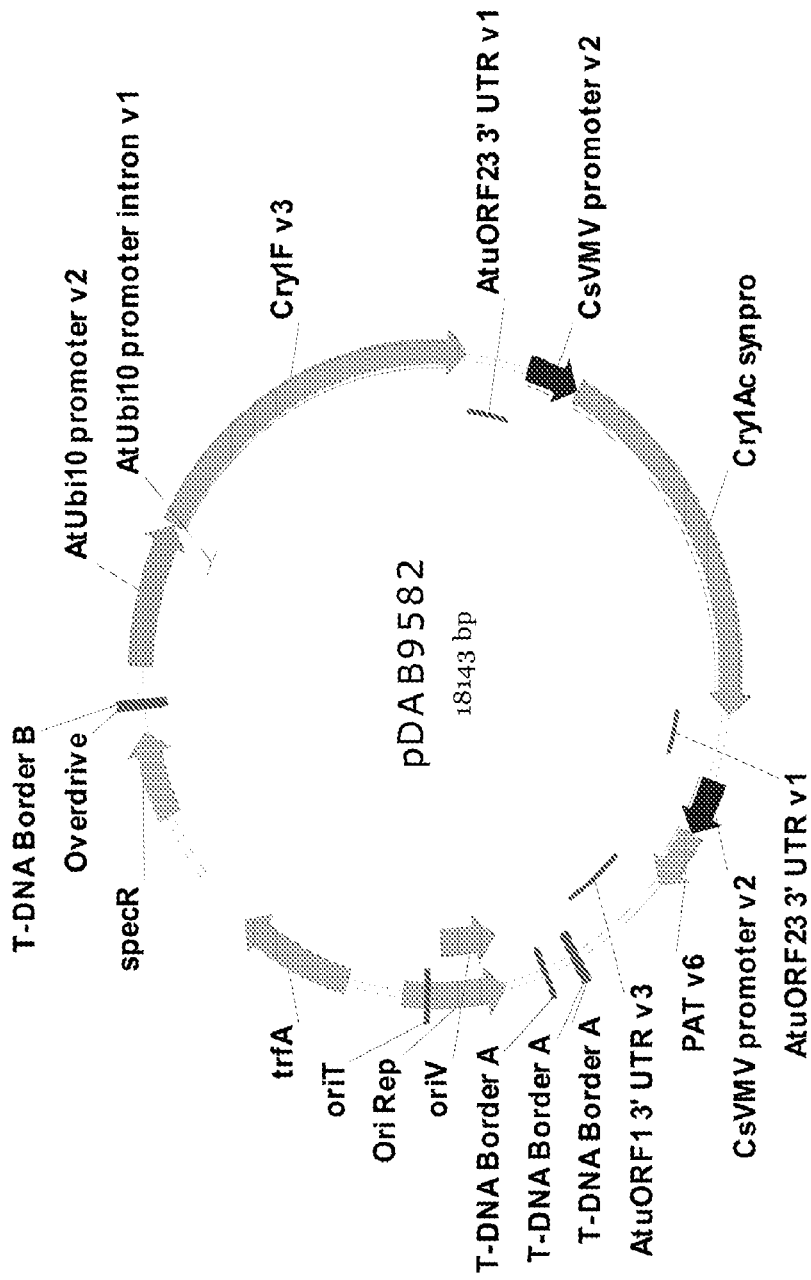
Figure 1. is a plasmid Map of pDAB9582 containing the *cry1F* v3, *cry1Ac* and *pat* v6 expression cassette.

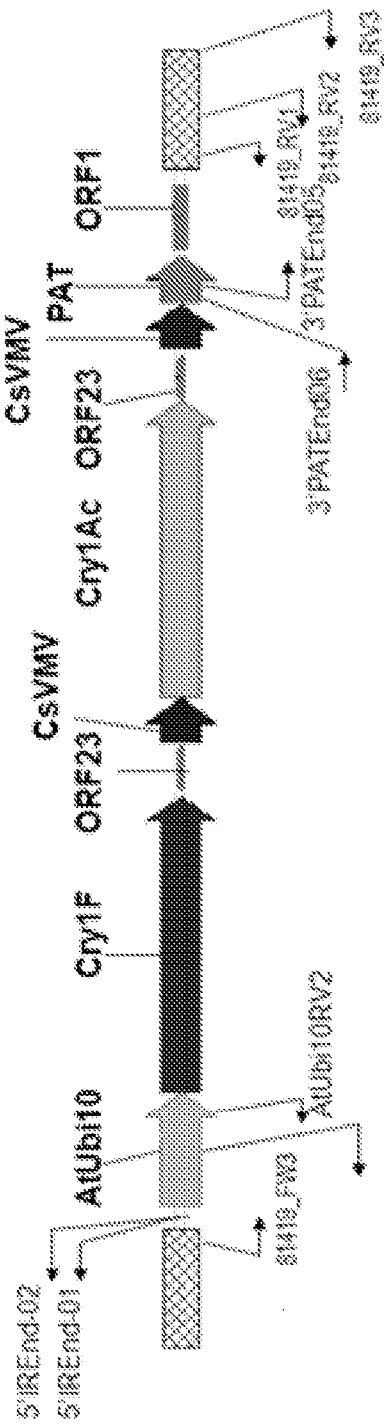
Figure 2. The diagram depicts the primer locations for confirming the 5' and 3' border sequence of the soybean event - pDAB9582.814.19.1.

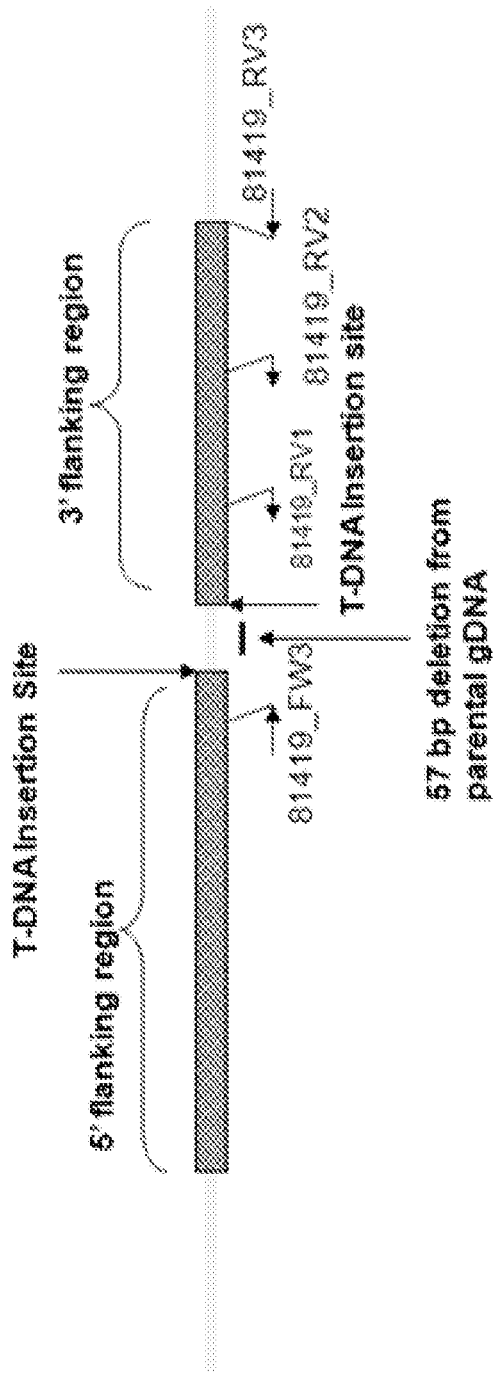
Figure 3. The diagram depicts the genomic sequence arrangement in soybean event pDAB9582.814.19.1

INSECT RESISTANT AND HERBICIDE TOLERANT BREEDING STACK OF SOYBEAN EVENT PDAB9582.814.19.1 AND PDAB4468.04.16.1

CROSS-REFERENCE TO RELATED APPLICATIONS

This application is a US National Phase filing of PCT/US2012/048302, filed on Jul. 26, 2012, which claims benefits of U.S. provisional applications 61/511,664 filed on Jul. 26, 2011, and 61/521,798, filed on Aug. 10, 2011. The disclosure of which is expressly incorporated entirely by reference.

BACKGROUND OF INVENTION

The genes encoding Cry1F and Cry1Ac synpro (Cry1Ac) are capable of imparting insect resistance, e.g. resistance to lepidopteran insects, to transgenic plants; and the gene encoding PAT (phosphinothricin acetyltransferase) is capable of imparting tolerance to the herbicide phoshpinothricin (glufosinate) to transgenic plants. PAT has been successfully expressed in soybean for use both as a selectable marker in producing insect resistant transgenic crops, and to impart commercial levels of tolerance to the herbicide glufosinate in transgenic crops. The gene encoding AAD-12 (aryloxyalkanoate dioxygenase-12) is capable of imparting commercial levels of tolerance to the phenoxyacetic acid herbicides, 2,4-D and MCPA, and the pyridyloxyacetic acid herbicides, triclopyr and fluroxypyr, when expressed in transgenic plants.

The expression of foreign genes in plants is known to be influenced by their location in the plant genome, perhaps due to chromatin structure (e.g., heterochromatin) or the proximity of transcriptional regulatory elements (e.g., enhancers) close to the integration site (Weising et al., *Ann. Rev. Genet* 22:421-477, 1988). At the same time the presence of the transgene at different locations in the genome will influence the overall phenotype of the plant in different ways. For this reason, it is often necessary to screen a large number of events in order to identify an event characterized by optimal expression of an introduced gene of interest. For example, it has been observed in plants and in other organisms that there may be a wide variation in levels of expression of an introduced gene among events. There may also be differences in spatial or temporal patterns of expression, for example, differences in the relative expression of a transgene in various plant tissues, that may not correspond to the patterns expected from transcriptional regulatory elements present in the introduced gene construct. For this reason, it is common to produce hundreds to thousands of different events and screen those events for a single event that has desired transgene expression levels and patterns for commercial purposes. An event that has desired levels or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are well adapted to local growing conditions.

It is desirable to be able to detect the presence of a particular event or multiple events in order to determine whether progeny of a sexual cross contain a transgene or group of transgenes of interest. In addition, a method for detecting a particular event or multiple events would be helpful for complying with regulations requiring the pre-market approval and labeling of foods derived from recombinant crop plants, for example, or for use in environmental monitoring, monitoring traits in crops in the field, or monitoring products derived from a crop harvest, as well as for use in ensuring compliance of parties subject to regulatory or contractual terms.

It is possible to detect the presence of one or more transgenic events by any nucleic acid detection method known in the art including, but not limited to, the polymerase chain reaction (PCR) or DNA hybridization using nucleic acid probes. These detection methods generally focus on frequently used genetic elements, such as promoters, terminators, marker genes, etc., because for many DNA constructs, the coding region is interchangeable. As a result, such methods may not be useful for discriminating between different events, particularly those produced using the same DNA construct or very similar constructs unless the DNA sequence of the flanking DNA adjacent to the inserted heterologous DNA is known. For example, an event-specific PCR assay is described in United States Patent Application 2006/0070139 for maize event DAS-59122-7. It would be desirable to have a simple and discriminative method for the identification of breeding stack soybean event pDAB9582.814.19.1::pDAB4468.04.16.1.

BRIEF SUMMARY OF THE INVENTION

The present invention relates to a new insect resistant and herbicide tolerant transgenic soybean breeding stack event, designated soybean event pDAB9582.814.19.1::pDAB4468.04.16.1. This breeding stack comprises cry1F, cry1Ac and pat, as described herein, and aad-12 and pat, as described herein and in International Patent Application No. WO/2012/075426 inserted into specific sites within the genome of a soybean cell. Representative soybean seed of a soybean line comprising soybean event pDAB9582.814.19.1 and a soybean line comprising soybean event pDAB4468.04.16.1 has been deposited with American Type Culture Collection (ATCC) with the Accession No. PTA-12006 and PTA-10442, respectively. The DNA of soybean plants containing this event includes the junction/flanking sequences described herein that characterize the location of the inserted DNA within the soybean genome. SEQ ID NO:1, SEQ ID NO:2, and SEQ ID NO:15 are diagnostic for soybean event pDAB9582.814.19.1::pDAB4468.04.16.1. More particularly, sequences surrounding the junctions at bp 1400/1401, bp 1536/1537 of SEQ ID NO:1, bp 152/153 of SEQ ID NO:2, bp 2730/2731 of SEQ ID NO:15, and bp 9121/9122 of SEQ ID NO:15 are diagnostic for soybean event pDAB9582.814.19.1::pDAB4468.04.16.1. Examples of sequences comprising these junctions that are characteristic of DNA of soybeans containing soybean event pDAB9582.814.19.1::pDAB4468.04.16.1 are described herein.

In one embodiment, the invention provides a soybean plant, or part thereof, that is resistant to *Pseudoplusia includens* (soybean looper) and that has a genome comprising one or more sequences selected from the group consisting of bp 1385-1415 of SEQ ID NO:1; bp 1350-1450 of SEQ ID NO:1; bp 1300-1500 of SEQ ID NO:1; bp 1200-1600 of SEQ ID NO:1; bp 137-168 of SEQ ID NO:2; bp 103-203 of SEQ ID NO:2; and bp 3-303 of SEQ ID NO:2; and one or more sequences selected from the group consisting of bp 2680-2780 of SEQ ID NO:15; bp 2630-2830 of SEQ ID NO:15; bp 2530-2930 of SEQ ID NO:15; bp 9071-9171 of SEQ ID NO:15; bp 9021-9221 of SEQ ID NO:15; and, bp 8921-9321 of SEQ ID NO:15 and complements thereof. In another embodiment, the invention provides seed of such plants.

In another embodiment, the invention provides a method of controlling insects that comprises exposing insects to insect resistant soybean plants, wherein the soybean plants have a genome that contains one or more sequence selected from the group consisting of bp 1385-1415 of SEQ ID NO:1; bp 1350-1450 of SEQ ID NO:1; bp 1300-1500 of SEQ ID NO:1; bp 1200-1600 of SEQ ID NO:1; bp 137-168 of SEQ ID NO:2; bp 103-203 of SEQ ID NO:2; and bp 3-303 of SEQ ID NO:2; and one or more sequences selected from the group consisting of bp 2680-2780 of SEQ ID NO:15; bp 2630-2830 of SEQ ID NO:15; bp 2530-2930 of SEQ ID NO:15; bp 9071-9171 of SEQ ID NO:15; bp 9021-9221 of SEQ ID NO:15; and, bp 8921-9321 of SEQ ID NO:15, and compliments thereof; which are characteristic of the presence of soybean event pDAB9582.814.19.1::pDAB4468.04.16.1, to thereby control the insects. Presence of the cry1F v3 (cry1F) and cry1Ac synpro (cry1Ac) genes in soybean event pDAB9582.814.19.1::pDAB4468.04.16.1 imparts resistance to, for example, *Pseudoplusia includens* (soybean looper), *Anticarsia gemmatalis* (velvetbean caterpillar), *Epinotia aporema, Omoides indicatus, Rachiplusia nu, Spodoptera frugiperda, Spodoptera cosmoides, Spodoptera eridania, Heliothis virescens, Heliocoverpa zea, Spilosoma virginica* and *Elasmopalpus lignosellus*.

In one embodiment, the invention provides a soybean plant, or part thereof, that is tolerant to phenoxyacetic acid herbicides such as 2,4-D and MCPA. In another embodiment, the invention provides a soybean plant, or part thereof, that is tolerant to the pyridyloxyacetic acid herbicides such as triclopyr and fluroxypyr. In these embodiments the soybean plant has a genome comprising one or more sequences selected from the group consisting of bp 1385-1415 of SEQ ID NO:1; bp 1350-1450 of SEQ ID NO:1; bp 1300-1500 of SEQ ID NO:1; bp 1200-1600 of SEQ ID NO:1; bp 137-168 of SEQ ID NO:2; bp 103-203 of SEQ ID NO:2; bp 3-303 of SEQ ID NO:2; and one or more sequences selected from the group consisting of bp 2680-2780 of SEQ ID NO:15; bp 2630-2830 of SEQ ID NO:15; bp 2530-2930 of SEQ ID NO:15; bp 9071-9171 of SEQ ID NO:15; bp 9021-9221 of SEQ ID NO:15; and, bp 8921-9321 of SEQ ID NO:15 and complements thereof. In another embodiment, the invention provides seed of such plants.

In another embodiment, the invention provides a method of controlling weeds in a soybean crop that comprises applying phenoxyacetic acid herbicides such as 2,4-D and MCPA. In another embodiment, the invention provides a method of controlling weeds in a soybean crop that comprises applying pyridyloxyacetic acid herbicides, such as triclopyr and fluroxypyr, to the soybean crop, where the soybean crop comprises soybean plants that have a genome containing one or more sequences selected from the group consisting of bp 1385-1415 of SEQ ID NO:1; bp 1350-1450 of SEQ ID NO:1; bp 1300-1500 of SEQ ID NO:1; bp 1200-1600 of SEQ ID NO:1; bp 137-168 of SEQ ID NO:2; bp 103-203 of SEQ ID NO:2; bp 3-303 of SEQ ID NO:2; and one or more sequences selected from the group consisting of bp 2680-2780 of SEQ ID NO:15; bp 2630-2830 of SEQ ID NO:15; bp 2530-2930 of SEQ ID NO:15; bp 9071-9171 of SEQ ID NO:15; bp 9021-9221 of SEQ ID NO:15; and, bp 8921-9321 of SEQ ID NO:15 and compliments thereof. Presence of the aad-12 gene in breeding stack soybean event pDAB9582.814.19.1::pDAB4468.04.16.1; imparts tolerance to phenoxyacetic acid herbicides and pyridyloxyacetic acid herbicides.

In another embodiment, the invention provides a method of controlling weeds in a soybean crop that comprises applying glufosinate herbicide to the soybean crop, said soybean crop comprising soybean plants that have a genome containing one or more sequence selected from the group consisting of bp 1385-1415 of SEQ ID NO:1; bp 1350-1450 of SEQ ID NO:1; bp 1300-1500 of SEQ ID NO:1; bp 1200-1600 of SEQ ID NO:1; bp 137-168 of SEQ ID NO:2; bp 103-203 of SEQ ID NO:2; bp 3-303 of SEQ ID NO:2; and one or more sequences selected from the group consisting of bp 2680-2780 of SEQ ID NO:15; bp 2630-2830 of SEQ ID NO:15; bp 2530-2930 of SEQ ID NO:15; bp 9071-9171 of SEQ ID NO:15; bp 9021-9221 of SEQ ID NO:15; and, bp 8921-9321 of SEQ ID NO:15, and complements thereof, which are diagnostic for the presence of soybean event pDAB9582.814.19.1::pDAB4468.04.16.1. Presence of the pat v6 (pat) gene in soybean event pDAB9582.814.19.1::pDAB4468.04.16.1 imparts tolerance to glufosinate herbicide.

In another embodiment, the invention provides a method of detecting soybean event pDAB9582.814.19.1::pDAB4468.04.16.1 in a sample comprising soybean DNA, said method comprising:

(a) contacting said sample with a first primer at least 10 bp in length that selectively binds to a flanking sequence within bp 1-1400 of SEQ ID NO:1 or the complement thereof, and a second primer at least 10 bp in length that selectively binds to an insert sequence within bp 1401-1836 of SEQ ID NO:1 or the complement thereof; and assaying for an amplicon generated between said primers; or (b) contacting said sample with a first primer at least 10 bp in length that selectively binds to an insert sequence within bp 1-152 of SEQ ID NO:2 or the complement thereof, and a second primer at least 10 bp in length that selectively binds to flanking sequence within bp 153-1550 of SEQ ID NO:2 or the complement thereof; or (c) contacting said sample with a first primer at least 10 bp in length that selectively binds to an insert sequence within bp 2731-9121 of SEQ ID NO:15 or the complement thereof, and a second primer at least 10 bp in length that selectively binds to flanking sequence within bp 1-2730 of SEQ ID NO:15 or the complement thereof; or (d) contacting said sample with a first primer at least 10 bp in length that selectively binds to an insert sequence within bp 2731-9121 of SEQ ID NO:15 or the complement thereof, and a second primer at least 10 bp in length that selectively binds to flanking sequence within bp 9122-10,198 of SEQ ID NO:15 or the complement thereof; and (e) assaying for an amplicon generated between said primers.

In another embodiment, the invention provides a method of detecting soybean event pDAB9582.814.19.1::pDAB4468.04.16.1 comprising:

(a) contacting said sample with a first primer that selectively binds to a flanking sequence selected from the group consisting of bp 1-1400 of SEQ ID NO:1 and bp 153-1550 of SEQ ID NO:2, and complements thereof; and a second primer that selectively binds to SEQ ID NO:3, or the complement thereof; and a third primer that selectively binds to a flanking sequence of bp 1-2730 of SEQ ID NO:15 and bp 9122-10,198 of SEQ ID NO:15, and complements thereof; and a fourth primer that selectively binds to an insert sequence of 2731-9121 of SEQ ID NO:15, and complements thereof.

(b) subjecting said sample to polymerase chain reaction; and (c) assaying for an amplicon generated between said primers.

In another embodiment the invention provides a method of breeding a soybean plant comprising: crossing a first plant with a second soybean plant to produce a third soybean plant, said first plant comprising DNA comprising one or more sequence selected from the group consisting of bp 1385-1415 of SEQ ID NO:1; bp 1350-1450 of SEQ ID NO:1; bp 1300-1500 of SEQ ID NO:1; bp 1200-1600 of SEQ ID NO:1; bp 137-168 of SEQ ID NO:2; bp 103-203 of SEQ ID NO:2; and bp 3-303 of SEQ ID NO:2; and one or more sequences selected from the group consisting of bp 2680-2780 of SEQ ID NO:15; bp 2630-2830 of SEQ ID NO:15; bp 2530-2930 of SEQ ID NO:15; bp 9071-9171 of SEQ ID NO:15; bp 9021-9221 of SEQ ID NO:15; and, bp 8921-9321 of SEQ ID NO:15, and complements thereof; and assaying said third soybean plant for presence of DNA comprising one or more sequences selected from the group consisting of bp 1385-1415 of SEQ ID NO:1; bp 1350-1450 of SEQ ID NO:1; bp 1300-1500 of SEQ ID NO:1; bp 1200-1600 of SEQ ID NO:1; bp 137-168 of SEQ ID NO:2; bp 103-203 of SEQ ID NO:2; bp 3-303 of SEQ ID NO:2; bp 2680-2780 of SEQ ID NO:15; bp 2630-2830 of SEQ ID NO:15; bp 2530-2930 of SEQ ID NO:15; bp 9071-9171 of SEQ ID NO:15; bp 9021-9221 of SEQ ID NO:15; and, bp 8921-9321 of SEQ ID NO:15, and complements thereof.

In another embodiment the invention provides an isolated DNA molecule that is diagnostic for soybean event pDAB9582.814.19.1::pDAB4468.04.16.1. Such molecules include, in addition to SEQ ID NOS: 1, 2, and 15 molecules at least 25 bp in length comprising bp 1400-1401 of SEQ ID NO:1 and at least 10 bp of SEQ ID NO:1 in each direction from the bp 1400/1401 junction; amplicons at least 25 bp in length comprising 152-153 of SEQ ID NO:2 and at least 10 bpy of SEQ ID NO:2 in each direction from the bp 152/153 junction; amplicons at least 25 bp in length comprising bp 2730-2731 of SEQ ID NO:15 and at least 10 bp of SEQ ID NO:15 in each direction from the bp 2730/2731 junction; amplicons at least 25 bp in length comprising bp 9121-9122 of SEQ ID NO:15 and at least 10 bp of SEQ ID NO:15 in each direction from the bp 9121/9122 junction. Examples are bp 1385-1415 of SEQ ID NO:1; bp 1350-1450 of SEQ ID NO:1; bp 1300-1500 of SEQ ID NO:1; bp 1200-1600 of SEQ ID NO:1; bp 137-168 of SEQ ID NO:2; bp 103-203 of SEQ ID NO:2; and bp 3-303 of SEQ ID NO:2; bp 2680-2780 of SEQ ID NO:15; bp 2630-2830 of SEQ ID NO:15; bp 2530-2930 of SEQ ID NO:15; bp 9071-9171 of SEQ ID NO:15; bp 9021-9221 of SEQ ID NO:15; and, bp 8921-9321 of SEQ ID NO:15, and complements thereof.

In another embodiment the invention provides a method of controlling pests in soybean grain, seed, or seed meal which comprises including soybean event pDAB9582.814.19.1::pDAB4468.04.16.1 in said grain, seed, or seed meal as demonstrated by said grain, seed, or seed meal comprising DNA comprising one or more sequence selected from the group consisting of bp1385-1415 of SEQ ID NO:1; bp 1350-1450 of SEQ ID NO:1; bp 1300-1500 of SEQ ID NO:1; bp 1200-1600 of SEQ ID NO:1; bp 137-168 of SEQ ID NO:2; bp 103-203 of SEQ ID NO:2; and bp 3-303 of SEQ ID NO:2; and one or more sequences selected from the group consisting of bp 2680-2780 of SEQ ID NO:15; bp 2630-2830 of SEQ ID NO:15; bp 2530-2930 of SEQ ID NO:15; bp 9071-9171 of SEQ ID NO:15; bp 9021-9221 of SEQ ID NO:15; and, bp 8921-9321 of SEQ ID NO:15, and complements thereof.

The invention also includes soybean plant cells and plant parts including, but are not limited to pollen, ovule, flowers, shoots, roots, and leaves, and nuclei of vegetative cells, pollen cells, seed and seed meal, and egg cells, that contain breeding stack soybean event pDAB9582.814.19.1::pDAB4468.04.16.1.

In some embodiments, breeding stack soybean event pDAB9582.814.19.1::pDAB4468.04.16.1 can be combined with other traits, including, for example, other herbicide tolerance gene(s) and/or insect-inhibitory proteins and transcription regulatory sequences (i.e. RNA interference, dsRNA, transcription factors, etc). The additional traits may be stacked into the plant genome via plant breeding, re-transformation of the transgenic plant containing breeding stack soybean event pDAB9582.814.19.1::pDAB4468.04.16.1, or addition of new traits through targeted integration.

Other embodiments include the excision of polynucleotide sequences which comprise breeding stack soybean event pDAB9582.814.19.1::pDAB4468.04.16.1, including for example, the pat gene expression cassette. Upon excision of a polynucleotide sequence, the modified event may be re-targeted at a specific chromosomal site wherein additional polynucleotide sequences are stacked with breeding stack soybean event pDAB9582.814.19.1::pDAB4468.04.16.1.

In one embodiment, the present invention encompasses a soybean chromosomal target site located on chromosome 02 between the flanking sequences set forth in SEQ ID NOS:1 and 2.

In one embodiment the present invention encompasses a soybean chromosomal target site located on chromosome 04 between the flanking sequences set forth in SEQ ID NO:15.

In one embodiment, the present invention encompasses a method of making a transgenic soybean plant comprising inserting a heterologous nucleic acid at a position on chromosome 02 between the genomic sequences set forth in SEQ ID NOS:1 and 2, i.e. between bp 1-1400 of SEQ ID NO:1 and bp 153-1550 of SEQ ID NO:2.

In one embodiment, the present invention encompasses a method of making a transgenic soybean plant comprising inserting a heterologous nucleic acid at a position on chromosome 04 between the genomic sequences set forth in SEQ ID NO:15, i.e. between bp 1-2730 of SEQ ID NO:15 and bp 9122-10,198 of SEQ ID NO:15.

Additionally, the subject invention provides assays for detecting the presence of the subject event in a sample (of soybeans, for example). The assays can be based on the DNA sequence of the recombinant construct, inserted into the soybean genome, and on the genomic sequences flanking the insertion site. Kits and conditions useful in conducting the assays are also provided.

The subject invention relates in part to the cloning and analysis of the DNA sequences of the border regions resulting from insertion of T-DNA from pDAB9582 and pDAB4468 in transgenic soybean lines. These sequences are unique. Based on the insert and junction sequences, event-specific primers can be and were generated. PCR analysis demonstrated that these events can be identified by analysis of the PCR amplicons generated with these event-specific primer sets. Thus, these and other related procedures can be used to uniquely identify soybean lines comprising the event of the subject invention.

SEED DEPOSIT

As part of this disclosure at least 2500 seeds of a soybean line comprising soybean event pDAB9582.814.19.1 and 2500 seeds of a soybean line comprising soybean event pDAB4468.04.16.1 have been deposited and made available to the public without restriction (but subject to patent rights), with the American Type Culture Collection (ATCC), 10801 University Boulevard, Manassas, Va., 20110. The deposits, designated as ATCC Deposit No. PTA-10442 (pDAB4468.04.16.1) and ATCC Deposit No. PTA-12006 (pDAB9582.814.19.1), were made on behalf of Dow AgroSciences LLC on Oct. 22, 2009 and Jul. 21, 2011, respectively. These deposits were made and will be maintained in accordance with and under the terms of the Budapest Treaty with respect to seed deposits for the purposes of patent procedure.

BRIEF DESCRIPTION OF THE SEQUENCES

SEQ ID NO:1 is the 5' DNA flanking border sequence for soybean event pDAB9582.814.19.1. Nucleotides 1-1400 are genomic sequence. Nucleotides 1401-1535 are a rearranged sequence from pDAB9582. Nucleotides 1536-1836 are insert sequence.

SEQ ID NO:2 is the 3' DNA flanking border sequence for soybean event pDAB9582.814.19.1. Nucleotides 1-152 are insert sequence. Nucleotides 153-1550 are genomic sequence.

SEQ ID NO:3 is the DNA sequence of pDAB9582, which is annotated below in Table 1.

SEQ ID NO:4 is oligonucleotide primer 81419_FW3 for confirmation of 5' border genomic DNA.

SEQ ID NO:5 is oligonucleotide primer 81419_RV1 for confirmation of 3' border genomic DNA.

SEQ ID NO:6 is oligonucleotide primer 81419_RV2 for confirmation of 3' border genomic DNA.

SEQ ID NO:7 is oligonucleotide primer 81419_RV3 for confirmation of 3' border genomic DNA.

SEQ ID NO:8 is oligonucleotide primer 5'IREnd-01 for confirmation of 5' border genomic DNA.

SEQ ID NO:9 is oligonucleotide primer 5'IREnd-02 for confirmation of 5' border genomic DNA.

SEQ ID NO:10 is oligonucleotide primer AtUbi10RV1 for confirmation of 5' border genomic DNA.

SEQ ID NO:11 is oligonucleotide primer AtUbi10RV2 for confirmation of 5' border genomic DNA.

SEQ ID NO:12 is oligonucleotide primer 3'PATEnd05 for confirmation of 3' border genomic DNA.

SEQ ID NO:13 is oligonucleotide primer 3'PATEnd06 for confirmation of 3' border genomic DNA.

SEQ ID NO:14 is the confirmed sequence of soybean event pDAB9582.814.19.1. Including the 5' genomic flanking sequence, pDAB9582 T-strand insert, and 3' genomic flanking sequence.

SEQ ID NO:15 is the confirmed sequence of soybean event pDAB4468.04.16.1. Including the 5' genomic flanking sequence, pDAB4468 T-strand insert, and 3' genomic flanking sequence.

BRIEF DESCRIPTION OF THE FIGURES

FIG. 1 is a plasmid Map of pDAB9582 containing the cry1F, cry1Ac and pat expression cassettes.

FIG. 2 depicts the primer locations for confirming the 5' and 3' border sequence of the soybean event pDAB9582.814.19.1.

FIG. 3 depicts the genomic sequence arrangement in soybean event pDAB9582.814.19.1

DETAILED DESCRIPTION OF THE INVENTION

The flanking sequences of soybean event pDAB9582.814.19.1::pDAB4468.04.16.1 insertion have been sequenced and characterized. Event specific assays were developed. It has also been mapped onto the soybean genome (soybean chromosome 02 and 04). The events can be introgressed together into further elite lines.

As alluded to above in the Background section, the introduction and integration of a transgene into a plant genome involves some random events (hence the name "event" for a given insertion that is expressed). That is, with many transformation techniques such as *Agrobacterium* transformation, the biolistic transformation (i.e. gene gun), and silicon carbide mediated transformation (i.e. WHISKERS™), it is unpredictable where in the genome a transgene will become inserted. Thus, identifying the flanking plant genomic DNA on both sides of the insert can be important for identifying a plant that has a given insertion event. For example, PCR primers can be designed that generate a PCR amplicon across the junction region of the insert and the host genome. This PCR amplicon can be used to identify a unique or distinct type of insertion event.

Definitions and examples are provided herein to help describe the present invention and to guide those of ordinary skill in the art to practice the invention. Unless otherwise noted, terms are to be understood according to conventional usage by those of ordinary skill in the relevant art. The nomenclature for DNA bases as set forth at 37 CFR §1.822 is used.

As used herein, the term "progeny" denotes the offspring of any generation of a parent plant which comprises breeding stack soybean event pDAB9582.814.19.1:: pDAB4468.04.16.1.

A transgenic "event" is produced by transformation of plant cells with heterologous DNA, i.e., a nucleic acid construct that includes the transgenes of interest, regeneration of a population of plants resulting from the insertion of the transgene into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety that includes the genomic/transgene DNA. Even after repeated back-crossing to a recurrent parent, the inserted transgene DNA and flanking genomic DNA (genomic/transgene DNA) from the transformed parent is present in the progeny of the cross at the same chromosomal location. The term "event" also refers to DNA from the original transformant and progeny thereof comprising the inserted DNA and flanking genomic sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

A "junction sequence" or "border sequence" spans the point at which DNA inserted into the genome is linked to DNA from the soybean native genome flanking the insertion point, the identification or detection of one or the other junction sequences in a plant's genetic material being sufficient to be diagnostic for the event. Included are the DNA sequences that span the insertions in herein-described soybean events and similar lengths of flanking DNA. Specific examples of such diagnostic sequences are provided herein; however, other sequences that overlap the junctions of the insertions, or the junctions of the insertions and the genomic sequence, are also diagnostic and could be used according to the subject invention.

The subject invention relates in part to event identification using such flanking, junction, and insert sequences. Related PCR primers and amplicons are included in the invention. According to the subject invention, PCR analysis methods using amplicons that span across inserted DNA and its borders can be used to detect or identify commercialized transgenic soybean varieties or lines derived from the subject proprietary transgenic soybean lines.

The flanking/junction sequences are diagnostic for breeding stack soybean event pDAB9582.814.19.1::pDAB4468.04.16.1. Based on these sequences, event-specific primers were generated. PCR analysis demonstrated that these soybean lines can be identified in different soybean genotypes by analysis of the PCR amplicons generated with these event-specific primer sets. Thus, these and other related procedures can be used to uniquely identify these soybean lines. The sequences identified herein are unique.

Detection techniques of the subject invention are especially useful in conjunction with plant breeding, to determine which progeny plants comprise a given event, after a parent plant comprising an event of interest is crossed with another plant line in an effort to impart one or more additional traits of interest in the progeny. These PCR analysis methods benefit soybean breeding programs as well as quality control, especially for commercialized transgenic soybean seeds. PCR detection kits for these transgenic soybean lines can also now be made and used. This can also benefit product registration and product stewardship.

Furthermore, flanking soybean/genomic sequences can be used to specifically identify the genomic location of each insert. This information can be used to make molecular marker systems specific to each event. These can be used for accelerated breeding strategies and to establish linkage data.

Still further, the flanking sequence information can be used to study and characterize transgene integration processes, genomic integration site characteristics, event sorting, stability of transgenes and their flanking sequences, and gene expression (especially related to gene silencing, transgene methylation patterns, position effects, and potential expression-related elements such as MARS [matrix attachment regions], and the like).

In light of all the subject disclosure, it should be clear that the subject invention includes seeds of a soybean line produced from a cross between a soybean line comprising event pDAB9582.814.19.1 and soybean line comprising event pDAB4468.04.16.1, seeds of those two parental lines being available under ATCC Deposit No. PTA-12006 and PTA-10442, respectively. The subject invention also includes an herbicide-tolerant soybean plant produced from a cross between a soybean line comprising soybean event pDAB9582.814.19.1 and a soybean line comprising soybean event pDAB4468.04.16.1. The subject invention further includes parts of said plant, such as leaves, tissue samples, seeds produced by said plant, pollen, and the like (wherein they comprise cry1F, cry1Ac, pat, and SEQ ID NOS: 1 and 2 in addition to aad-12, pat and SEQ ID NO:15).

Still further, the subject invention includes descendant and/or progeny plants of plants grown from the deposited seed, preferably a herbicide-resistant soybean plant wherein said plant has a genome comprising a detectable wild-type junction sequence as described herein. As used herein, the term "soybean" means Glycine max and includes all varieties thereof that can be bred with a soybean plant.

This invention further includes processes of making crosses using a plant of the subject invention as at least one parent. For example, the subject invention includes an $F_1$ hybrid plant having as one or both parents any of the plants exemplified herein, including but not limited to having one parent comprising soybean event pDAB9582.814.19.1 and another parent comprising pDAB4468.04.16.1. Also within the subject invention is seed produced by such $F_1$ hybrids of the subject invention. This invention includes a method for producing an $F_1$ hybrid seed by crossing an exemplified plant with a different (e.g. in-bred parent) plant and harvesting the resultant hybrid seed. The subject invention includes an exemplified plant that is either a female parent or a male parent. Characteristics of the resulting plants may be improved by careful consideration of the parent plants.

An insect resistant/2,4 D-tolerant/glufosinate-tolerant soybean plant of the subject invention can be bred by first sexually crossing a first parental soybean plant consisting of a soybean plant grown from seed of any one of the lines referred to herein, and a second parental soybean plant, thereby producing a plurality of first progeny plants; then selecting a first progeny plant that is resistant to glufosinate and/or 2,4-D; selfing the first progeny plant, thereby producing a plurality of second progeny plants; and then selecting from the second progeny plants a plant that is resistant to glufosinate and/or 2,4-D. These steps can further include the back-crossing of the first progeny plant or the second progeny plant to the second parental soybean plant or a third parental soybean plant. A soybean crop comprising soybean seeds of the subject invention, or progeny thereof, can then be planted.

It is also to be understood that two different transgenic plants can also be mated to produce offspring that contain two independently segregating, added, exogenous genes. Selfing of appropriate progeny can produce plants that are homozygous for both added, exogenous genes. Back-crossing to a parental plant and out-crossing with a non-transgenic plant are also contemplated, as is vegetative propagation. Other breeding methods commonly used for different traits and crops are known in the art. Backcross breeding has been used to transfer genes for a simply inherited, highly heritable trait into a desirable homozygous cultivar or inbred line, which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting parent is expected to have the attributes of the recurrent parent (e.g., cultivar) and the desirable trait transferred from the donor parent.

Likewise an insect resistant/2,4 D-tolerant/glufosinate-tolerant soybean plant of the subject invention can be transformed with additional transgenes using methods known in the art. Transformation techniques such as Agrobacterium transformation, the biolistic transformation (i.e. gene gun), and silicon carbide mediated transformation (i.e. WHISKERS), can be used to introduced additional trangene(s) into the genome of breeding stack soybean event pDAB9582.814.19.1::pDAB4468.04.16.1. Selection and characterization of transgenic plants containing the newly inserted transgenes can be completed to identify plants which contain a stable integrant of the novel transgene in addition to aad-12, cry1F, cry1Ac, pat genes of the subject invention.

The DNA molecules of the present invention can be used as molecular markers in a marker assisted breeding (MAB) method. DNA molecules of the present invention can be used in methods (such as, AFLP markers, RFLP markers, RAPD markers, SNPs, and SSRs) that identify genetically linked agronomically useful traits, as is known in the art. The insect resistance and herbicide-tolerance traits can be tracked in the progeny of a cross with a soybean plant of the subject invention (or progeny thereof and any other soybean cultivar or variety) using the MAB methods. The DNA molecules are markers for this trait, and MAB methods that are well known in the art can be used to track the hebicide-resistance trait(s) in soybean plants where at least one soybean line of the subject invention, or progeny thereof, was a parent or ancestor. The methods of the present invention can be used to identify any soybean variety having the subject event.

Methods of the subject invention include a method of producing an insect resistant/herbicide-tolerant soybean plant wherein said method comprises breeding with a plant of the subject invention. More specifically, said methods can comprise crossing two plants of the subject invention, or one plant of the subject invention and any other plant. Preferred methods further comprise selecting progeny of said cross by analyzing said progeny for an event detectable according to the subject invention and favorable varietal performance (e.g. yield). For example, the subject invention can be used to track the subject event through breeding cycles with plants comprising other desirable traits, such as agronomic traits, disease tolerance or resistance, nematode tolerance or resistance and maturity date. Plants comprising the subject event and the desired trait can be detected, identified, selected, and quickly used in further rounds of breeding, for example. The subject event/trait can also be combined through breeding, and tracked according to the subject invention, with further insect resistant trait(s) and/or with further herbicide tolerance traits. Embodiments of the latter are plants comprising the subject event combined with a glyphosate tolerance gene, which confers tolerance to the herbicide glyphosate.

Thus, the subject invention can be combined with, for example, traits encoding glyphosate resistance (e.g., resistant plant or bacterial EPSPS, GOX, GAT), glufosinate resistance (e.g., pat, bar), acetolactate synthase (ALS)-inhibiting herbicide resistance (e.g., imidazolinones [such as imazethapyr], sulfonylureas, triazolopyrimidine sulfonanilide, pyrmidinylthiobenzoates, and other chemistries [Csr1, SurA, et al.]), bromoxynil resistance (e.g., Bxn), resistance to inhibitors of HPPD (4-hydroxlphenyl-pyruvate-dioxygenase) enzyme, resistance to inhibitors of phytoene desaturase (PDS), resistance to photosystem II inhibiting herbicides (e.g., psbA), resistance to photosystem I inhibiting herbicides, resistance to protoporphyrinogen oxidase IX (PPO)-inhibiting herbicides (e.g., PPO-1), resistance to phenylurea herbicides (e.g., CYP76B1), dicamba-degrading enzymes (see, e.g., US 20030135879), and others could be stacked alone or in multiple combinations to provide the ability to effectively control or prevent weed shifts and/or resistance to any herbicide of the aforementioned classes.

Additionally, breeding stack soybean event pDAB9582.814.19.1::pDAB4468.04.16.1 can be combined with one or more additional input (e.g., insect resistance, pathogen resistance, or stress tolerance, et al.) or output (e.g., increased yield, improved oil profile, improved fiber quality, et al.) traits. Thus, the subject invention can be used to provide a complete agronomic package of improved crop quality with the ability to flexibly and cost effectively control any number of agronomic pests.

Methods to integrate a polynucleotide sequence within a specific chromosomal site of a plant cell via homologous recombination have been described within the art. For instance, site specific integration as described in US Patent Application Publication No. 2009/0111188 A1, herein incorporated by reference, describes the use of recombinases or integrases to mediate the introduction of a donor polynucleotide sequence into a chromosomal target. In addition, International Patent Application No. WO 2008/021207, herein incorporated by reference, describes zinc finger mediated-homologous recombination to integrate one or more donor polynucleotide sequences within specific locations of the genome. The use of recombinases such as FLP/FRT as described in U.S. Pat. No. 6,720,475, herein incorporated by reference, or CRE/LOX as described in U.S. Pat. No. 5,658,772, herein incorporated by reference, can be utilized to integrate a polynucleotide sequence into a specific chromosomal site. Finally the use of meganucleases for targeting donor polynucleotides into a specific chromosomal location was described in Puchta et al., PNAS USA 93 (1996) pp. 5055-5060).

Other methods for site specific integration within plant cells are generally known and applicable (Kumar et al., Trends in Plant Sci. 6(4) (2001) pp. 155-159). Furthermore, site-specific recombination systems which have been identified in several prokaryotic and lower eukaryotic organisms may be applied to use in plants. Examples of such systems include, but are not limited too; the R/RS recombinase system from the pSR1 plasmid of the yeast *Zygosaccharomyces rouxii* (Araki et al. (1985) J. Mol. Biol. 182: 191-203), and the Gin/gix system of phage Mu (Maeser and Kahlmann (1991) Mol. Gen. Genet. 230: 170-176).

In some embodiments of the present invention, it can be desirable to integrate or stack a new transgene(s) in proximity to an existing transgenic event. The transgenic event can be considered a preferred genomic locus which was selected based on unique characteristics such as single insertion site, normal Mendelian segregation and stable expression, and a superior combination of efficacy, including herbicide tolerance and agronomic performance in and across multiple environmental locations. The newly integrated transgenes should maintain the transgene expression characteristics of the existing transformants. Moreover, the development of assays for the detection and confirmation of the newly integrated event would be overcome as the genomic flanking sequences and chromosomal location of the newly integrated event are already identified. Finally, the integration of a new transgene into a specific chromosomal location which is linked to an existing transgene would expedite the introgression of the transgenes into other genetic backgrounds by sexual out-crossing using conventional breeding methods.

In some embodiments of the present invention, it can be desirable to excise polynucleotide sequences from a transgenic event. For instance transgene excision as described in Provisional U.S. Patent Application No. 61/297,628, herein incorporated by reference, describes the use of zinc finger nucleases to remove a polynucleotide sequence, consisting of a gene expression cassette, from a chromosomally integrated transgenic event. The polynucleotide sequence which is removed can be a selectable marker. Upon excision and removal of a polynucleotide sequence the modified transgenic event can be retargeted by the insertion of a polynucleotide sequence. The excision of a polynucleotide sequence and subsequent retargeting of the modified transgenic event provides advantages such as re-use of a selectable marker or the ability to overcome unintended changes to the plant transcriptome which results from the expression of specific genes.

The subject invention discloses herein a specific site on chromosome 02 in the soybean genome that is excellent for insertion of heterologous nucleic acids. Thus, the subject invention provides methods to introduce heterologous nucleic acids of interest into this pre-established target site or in the vicinity of this target site. The subject invention also encompasses a soybean seed and/or a soybean plant comprising any heterologous nucleotide sequence inserted at the disclosed target site or in the general vicinity of such site. One option to accomplish such targeted integration is to excise and/or substitute a different insert in place of the pat expression cassette exemplified herein. In this general regard, targeted homologous recombination, for example and without limitation, can be used according to the subject invention.

As used herein gene, event or trait "stacking" is combining desired traits into one transgenic line. Plant breeders stack transgenic traits by making crosses between parents that each have a desired trait and then identifying offspring that have both of these desired traits. Another way to stack genes is by transferring two or more genes into the cell nucleus of a plant at the same time during transformation. Another way to stack genes is by re-transforming a transgenic plant with another gene of interest. For example, gene stacking can be used to combine two or more different traits, including for example, two or more different insect traits, insect resistance trait(s) and disease resistance trait(s), two or more herbicide resistance traits, and/or insect resistance trait(s) and herbicide resistant trait(s). The use of a selectable marker in addition to a gene of interest can also be considered gene stacking.

"Homologous recombination" refers to a reaction between any pair of nucleotide sequences having corresponding sites containing a similar nucleotide sequence through which the two nucleotide sequences can interact (recombine) to form a new, recombinant DNA sequence. The sites of similar nucleotide sequence are each referred to herein as a "homology sequence." Generally, the frequency of homologous recombination increases as the length of the homology sequence increases. Thus, while homologous recombination can occur between two nucleotide sequences that are less than identical, the recombination frequency (or efficiency) declines as the divergence between the two sequences increases. Recombination may be accomplished using one homology sequence on each of the donor and target molecules, thereby generating a "single-crossover" recombination product. Alternatively, two homology sequences may be placed on each of the target and donor nucleotide sequences. Recombination between two homology sequences on the donor with two homology sequences on the target generates a "double-crossover" recombination product. If the homology sequences on the donor molecule flank a sequence that is to be manipulated (e.g., a sequence of interest), the double-crossover recombination with the target molecule will result in a recombination product wherein the sequence of interest replaces a DNA sequence that was originally between the homology sequences on the target molecule. The exchange of DNA sequence between the target and donor through a double-crossover recombination event is termed "sequence replacement."

A preferred plant, or a seed, of the subject invention comprises in its genome operative aad-12, cry1F v3, cry1Ac synpro and pat v6 nucleotide sequences, as identified herein, together with at least 20-500 or more contiguous flanking nucleotides on both sides of the insert, as identified herein. Unless indicated otherwise, reference to flanking sequences refers to those identified with respect to SEQ ID NOS: 1, 2, and 15. All or part of these flanking sequences could be expected to be transferred to progeny that receives the inserted DNA as a result of a sexual cross of a parental line that includes the event.

The subject invention includes tissue cultures of regenerable cells of a plant of the subject invention. Also included is a plant regenerated from such tissue culture, particularly where said plant is capable of expressing all the morphological and physiological properties of an exemplified variety. Preferred plants of the subject invention have all the physiological and morphological characteristics of a plant grown from the deposited seed. This invention further comprises progeny of such seed and seed possessing the quality traits of interest.

As used herein, a "line" is a group of plants that display little or no genetic variation between individuals for at least one trait. Such lines may be created by several generations of self-pollination and selection, or vegetative propagation from a single parent using tissue or cell culture techniques.

As used herein, the terms "cultivar" and "variety" are synonymous and refer to a line which is used for commercial production.

"Stability" or "stable" means that with respect to the given component, the component is maintained from generation to generation and, preferably, at least three generations.

"Commercial Utility" is defined as having good plant vigor and high fertility, such that the crop can be produced by farmers using conventional farming equipment, and the oil with the described components can be extracted from the seed using conventional crushing and extraction equipment "Agronomically elite" means that a line has desirable agronomic characteristics such as yield, maturity, disease resistance, and the like, in addition to the insect resistance and herbicide tolerance due to the subject event(s). Any and all of these agronomic characteristics and data points can be used to identify such plants, either as a point or at either end or both ends of a range of chracteristics used to define such plants.

As one skilled in the art will recognize in light of this disclosure, preferred embodiments of detection kits, for example, can include probes and/or primers directed to and/or comprising "junction sequences" or "transition sequences" (where the soybean genomic flanking sequence meets the insert sequence). For example, this includes a polynucleotide probes, primers, and/or amplicons designed to identify one or both junction sequences (where the insert meets the flanking sequence), as indicated in the Table above. One common design is to have one primer that hybridizes in the flanking region, and one primer that hybridizes in the insert. Such primers are often each about at least ~15 residues in length. With this arrangement, the primers can be used to generate/amplify a detectable amplicon that indicates the presence of an event of the subject invention. These primers can be used to generate an amplicon that spans (and includes) a junction sequence as indicated above.

The primer(s) "touching down" in the flanking sequence is typically not designed to hybridize beyond about 1200 bases or so beyond the junction. Thus, typical flanking primers would be designed to comprise at least 15 residues of either strand within 1200 bases into the flanking sequences from the beginning of the insert. That is, primers comprising a sequence of an appropriate size from (or hybridizing to) base pairs 800 to 1400 of SEQ ID NO:1 and/or base pairs 153 to 753 of SEQ ID NO:2 and/or base pairs 2130 to 2730 of SEQ ID NO:15 and/or base pairs 9122 to 9722 of SEQ ID NO:15 are within the scope of the subject invention. Insert primers can likewise be designed anywhere on the insert of SEQ ID NO:3 or anywhere between base pairs 2731 and 9121 of SEQ ID NO:15, and can be used, for example, non-exclusively for such primer design.

One skilled in the art will also recognize that primers and probes can be designed to hybridize, under a range of standard hybridization and/or PCR conditions wherein the primer or probe is not perfectly complementary to the exemplified sequence. That is, some degree of mismatch can be tolerated. For an approximately 20 nucleotide primer, for example, typically one or two or so nucleotides do not need to bind with the opposite strand if the mismatched base is internal or on the end of the primer that is opposite the amplicon. Various appropriate hybridization conditions are provided below. Synthetic nucleotide analogs, such as inosine, can also be used in probes. Peptide nucleic acid (PNA) probes, as well as DNA and RNA probes, can also be used. What is important is that such probes and primers are diagnostic for (able to uniquely identify and distinguish) the presence of an event of the subject invention.

It should be noted that errors in PCR amplification can occur which might result in minor sequencing errors, for example. That is, unless otherwise indicated, the sequences listed herein were determined by generating long amplicons from soybean genomic DNAs, and then cloning and sequencing the amplicons. It is not unusual to find slight differences and minor discrepancies in sequences generated and determined in this manner, given the many rounds of amplification that are necessary to generate enough amplicon for sequencing from genomic DNAs. One skilled in the art should recognize and be put on notice that any adjustments needed due to these types of common sequencing errors or discrepancies are within the scope of the subject invention.

It should also be noted that it is not uncommon for some genomic sequence to be deleted, for example, when a sequence is inserted during the creation of an event. Thus, some differences can also appear between the subject flanking sequences and genomic sequences listed in GENBANK, for example.

Components of the DNA sequence "insert" are illustrated in the Figures and are discussed in more detail below in the Examples. The DNA polynucleotide sequences of these components, or fragments thereof, can be used as DNA primers or probes in the methods of the present invention.

In some embodiments of the invention, compositions and methods are provided for detecting the presence of the transgene/genomic insertion region, in plants and seeds and the like, from a soybean plant. DNA sequences are provided that comprise the subject 5' transgene/genomic insertion region junction sequence provided herein (between base pairs 800 to 1400 of SEQ ID NO:1 and SEQ ID NO:3), segments thereof, and complements of the exemplified sequences and any segments thereof. DNA sequences are provided that comprise the subject 3' transgene/genomic insertion region junction sequence provided herein (between base pairs 153 to 753 of SEQ ID NO:2 and SEQ ID NO:3), segments thereof, and complements of the exemplified sequences and any segments thereof. DNA sequences are provided that comprise the subject 3' transgene/genomic insertion region junction sequence provided herein (between base pairs 1 to 2730 of SEQ ID NO:15 and 2731 to 9121 SEQ ID NO:15), segments thereof, and complements of the exemplified sequences and any segments thereof. DNA sequences are provided that comprise the subject 3' transgene/genomic insertion region junction sequence provided herein (between base pairs 9122 to 10,198 of SEQ ID NO:15 and 2731 to 9121 of SEQ ID NO:15), segments thereof, and complements of the exemplified sequences and any segments thereof. The insertion region junction sequence spans the junction between heterologous DNA inserted into the genome and the DNA from the soybean cell flanking the insertion site. Such sequences can be diagnostic for the given event.

Based on these insert and border sequences, event-specific primers can be generated. PCR analysis demonstrated that soybean lines of the subject invention can be identified in different soybean genotypes by analysis of the PCR amplicons generated with these event-specific primer sets. These and other related procedures can be used to uniquely identify these soybean lines. Thus, PCR amplicons derived from such primer pairs are unique and can be used to identify these soybean lines.

In some embodiments, DNA sequences that comprise a contiguous fragment of the novel transgene/genomic insertion region are an aspect of this invention. Included are DNA sequences that comprise a sufficient length of polynucleotides of transgene insert sequence and a sufficient length of polynucleotides of soybean genomic sequence from one or more of the three aforementioned soybean plants and/or sequences that are useful as primer sequences for the production of an amplicon product diagnostic for one or more of these soybean plants.

Related embodiments pertain to DNA sequences that comprise at least 10, 11, 12, 13, 14, 15, 16, 17, 18, 19, 20, 21, 22, 23, 24, 25, or more contiguous nucleotides of a transgene portion of a DNA sequence identified herein (such as SEQ ID NO:1 and segments thereof), or complements thereof, and a similar length of flanking soybean DNA sequence from these sequences, or complements thereof. Such sequences are useful as DNA primers in DNA amplification methods. The amplicons produced using these primers are diagnostic for any of the soybean event referred to herein. Therefore, the invention also includes the amplicons produced by such DNA primers and homologous primers.

This invention also includes methods of detecting the presence of DNA, in a sample, that corresponds to the soybean event referred to herein. Such methods can comprise: (a) contacting the sample comprising DNA with a primer set that, when used in a nucleic acid amplification reaction with DNA from at least one of these soybean event, produces an amplicon that is diagnostic for said event(s); (b) performing a nucleic acid amplification reaction, thereby producing the amplicon; and (c) detecting the amplicon.

Further detection methods of the subject invention include a method of detecting the presence of a DNA, in a sample, corresponding to said event, wherein said method comprises: (a) contacting the sample comprising DNA with a probe that hybridizes under stringent hybridization conditions with DNA from at least one of said soybean event and which does not hybridize under the stringent hybridization conditions with a control soybean plant (non-event-of-interest DNA); (b) subjecting the sample and probe to stringent hybridization conditions; and (c) detecting hybridization of the probe to the DNA.

In still further embodiments, the subject invention includes methods of producing a soybean plant comprising soybean event pDAB9582.814.19.1::pDAB4468.04.16.1 of the subject invention, wherein said method comprises the steps of: (a) sexually crossing a first parental soybean line (comprising an expression cassettes of the present invention, which confers glufosinate tolerance to plants of said line) and a second parental soybean line (that lacks this herbicide tolerance trait) thereby producing a plurality of progeny plants; and (b) selecting a progeny plant by the use of molecular markers. Such methods may optionally comprise the further step of back-crossing the progeny plant to the second parental soybean line to producing a true-breeding soybean plant that comprises the insect resistant, 2,4-D, and glufosinate tolerant trait.

According to another aspect of the invention, methods of determining the zygosity of progeny of a cross with said event is provided. Said methods can comprise contacting a sample, comprising soybean DNA, with a primer set of the subject invention. Said primers, when used in a nucleic-acid amplification reaction with genomic DNA from at least one of said soybean event, produces a first amplicon that is diagnostic for at least one of said soybean events. Such methods further comprise performing a nucleic acid amplification reaction, thereby producing the first amplicon; detecting the first amplicon; and contacting the sample comprising soybean DNA with a second primer set (said second primer set, when used in a nucleic-acid amplification reaction with genomic DNA from soybean plants, produces a second amplicon comprising the native soybean genomic DNA homologous to the soybean genomic region); and performing a nucleic acid amplification reaction, thereby producing the second amplicon. The methods further comprise detecting the second amplicon, and comparing the first and second amplicons in a sample, wherein the presence of both amplicons indicates that the sample is heterozygous for the transgene insertion.

DNA detection kits can be developed using the compositions disclosed herein and methods well known in the art of DNA detection. The kits are useful for identification of the subject soybean event DNA in a sample and can be applied to methods for breeding soybean plants containing this DNA. The kits contain DNA sequences homologous or complementary to the amplicons, for example, disclosed herein, or to DNA sequences homologous or complementary to DNA contained in the transgene genetic elements of the subject events. These DNA sequences can be used in DNA amplification reactions or as probes in a DNA hybridization method. The kits may also contain the reagents and materials necessary for the performance of the detection method.

A "probe" is an isolated nucleic acid molecule to which is attached a conventional detectable label or reporter molecule (such as a radioactive isotope, ligand, chemiluminescent agent, or enzyme). Such a probe is complementary to a strand of a target nucleic acid, in the case of the present invention, to a strand of genomic DNA from one of said soybean events, whether from a soybean plant or from a sample that includes DNA from the event. Probes according to the present invention include not only deoxyribonucleic or ribonucleic acids but also polyamides and other probe materials that bind specifically to a target DNA sequence and can be used to detect the presence of that target DNA sequence.

"Primers" are isolated/synthesized nucleic acids that are annealed to a complementary target DNA strand by nucleic acid hybridization to form a hybrid between the primer and the target DNA strand, then extended along the target DNA strand by a polymerase, e.g., a DNA polymerase. Primer pairs of the present invention refer to their use for amplification of a target nucleic acid sequence, e.g., by the polymerase chain reaction (PCR) or other conventional nucleic-acid amplification methods.

Probes and primers are generally 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, or 1000, or 2000, or 5000 polynucleotides or more in length. Such probes and primers hybridize specifically to a target sequence under high stringency hybridization conditions. Preferably, probes and primers according to the present invention have complete sequence similarity with the target sequence, although probes differing from the target sequence and that retain the ability to hybridize to target sequences may be designed by conventional methods.

Methods for preparing and using probes and primers are described, for example, in Molecular Cloning: A Laboratory Manual, 2nd ed., vol. 1-3, ed. Sambrook et al., Cold Spring Harbor Laboratory Press, Cold Spring Harbor, N.Y., 1989. PCR-primer pairs can be derived from a known sequence, for example, by using computer programs intended for that purpose.

Primers and probes based on the flanking DNA and insert sequences disclosed herein can be used to confirm (and, if necessary, to correct) the disclosed sequences by conventional methods, e.g., by re-cloning and sequencing such sequences.

The nucleic acid probes and primers of the present invention hybridize under stringent conditions to a target DNA sequence. Any conventional nucleic acid hybridization or amplification method can be used to identify the presence of DNA from a transgenic event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989. Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. The term "stringent conditions" is functionally defined with regard to the hybridization of a nucleic-acid probe to a target nucleic acid (i.e., to a particular nucleic-acid sequence of interest) by the specific hybridization procedure discussed in Sambrook et al., 1989, at 9.52-9.55. See also, Sambrook et al., 1989 at 9.47-9.52 and 9.56-9.58. Accordingly, the nucleotide sequences of the invention may be used for their ability to selectively form duplex molecules with complementary stretches of DNA fragments.

Depending on the application envisioned, one can use varying conditions of hybridization to achieve varying degrees of selectivity of probe towards target sequence. For applications requiring high selectivity, one will typically employ relatively stringent conditions to form the hybrids, e.g., one will select relatively low salt and/or high temperature conditions, such as provided by about 0.02 M to about 0.15 M NaCl at temperatures of about 50° C. to about 70° C. Stringent conditions, for example, could involve washing the hybridization filter at least twice with high-stringency wash buffer (0.2×SSC, 0.1% SDS, 65° C.). Appropriate stringency conditions which promote DNA hybridization, for example, 6.0× sodium chloride/sodium citrate (SSC) at about 45° C., followed by a wash of 2.0×SSC at 50° C. are known to those skilled in the art. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. Such selective conditions tolerate little, if any, mismatch between the probe and the template or target strand. Detection of DNA sequences via hybridization is well-known to those of skill in the art, and the teachings of U.S. Pat. Nos. 4,965,188 and 5,176,995 are exemplary of the methods of hybridization analyses.

In a particularly preferred embodiment, a nucleic acid of the present invention will specifically hybridize to one or more of the primers (or amplicons or other sequences) exemplified or suggested herein, including complements and fragments thereof, under high stringency conditions. In one aspect of the present invention, a marker nucleic acid molecule of the present invention has the nucleic acid sequence as set forth herein in one of the exemplified sequences, or complements and/or fragments thereof.

In another aspect of the present invention, a marker nucleic acid molecule of the present invention shares between 80% and 100% or 90% and 100% sequence identity with such nucleic acid sequences. In a further aspect of the present invention, a marker nucleic acid molecule of the present invention shares between 95% and 100% sequence identity with such sequence. Such sequences may be used as markers in plant breeding methods to identify the progeny of genetic crosses. The hybridization of the probe to the target DNA molecule can be detected by any number of methods known to those skilled in the art, these can include, but are not limited to, fluorescent tags, radioactive tags, antibody based tags, and chemiluminescent tags.

Regarding the amplification of a target nucleic acid sequence (e.g., by PCR) using a particular amplification primer pair, "stringent conditions" are conditions that permit the primer pair to hybridize only to the target nucleic-acid sequence to which a primer having the corresponding wild-type sequence (or its complement) would bind and preferably to produce a unique amplification product, the amplicon.

The term "specific for (a target sequence)" indicates that a probe or primer hybridizes under stringent hybridization conditions only to the target sequence in a sample comprising the target sequence.

As used herein, "amplified DNA" or "amplicon" refers to the product of nucleic-acid amplification of a target nucleic acid sequence that is part of a nucleic acid template. For example, to determine whether the soybean plant resulting from a sexual cross contains transgenic event genomic DNA from the soybean plant of the present invention, DNA extracted from a soybean plant tissue sample may be subjected to nucleic acid amplification method using a primer pair that includes a primer derived from flanking sequence in the genome of the plant adjacent to the insertion site of inserted heterologous DNA, and a second primer derived from the inserted heterologous DNA to produce an amplicon that is diagnostic for the presence of the event DNA. The amplicon is of a length and has a sequence that is also diagnostic for the event. The amplicon may range in length from the combined length of the primer pairs plus one nucleotide base pair, and/or the combined length of the primer pairs plus about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500, 750, 1000, 1250, 1500, 1750, 2000, or more nucleotide base pairs (plus or minus any of the increments listed above). Alternatively, a primer pair can be derived from flanking sequence on both sides of the inserted DNA so as to produce an amplicon that includes the entire insert nucleotide sequence. A member of a primer pair derived from the plant genomic sequence may be located a distance from the inserted DNA sequence. This distance can range from one nucleotide base pair up to about twenty thousand nucleotide base pairs. The use of the term "amplicon" specifically excludes primer dimers that may be formed in the DNA thermal amplification reaction.

Nucleic-acid amplification can be accomplished by any of the various nucleic-acid amplification methods known in the art, including the polymerase chain reaction (PCR). A variety of amplification methods are known in the art and are described, inter alia, in U.S. Pat. No. 4,683,195 and U.S. Pat. No. 4,683,202. PCR amplification methods have been developed to amplify up to 22 kb of genomic DNA. These methods as well as other methods known in the art of DNA amplification may be used in the practice of the present invention. The sequence of the heterologous transgene DNA insert or flanking genomic sequence from a subject soybean event can be verified (and corrected if necessary) by amplifying such sequences from the event using primers derived from the sequences provided herein followed by standard DNA sequencing of the PCR amplicon or of the cloned DNA.

The amplicon produced by these methods may be detected by a plurality of techniques. Agarose gel electrophoresis and staining with ethidium bromide is a common well known method of detecting DNA amplicons. Another such method is Genetic Bit Analysis where an DNA oligonucleotide is designed which overlaps both the adjacent flanking genomic DNA sequence and the inserted DNA sequence. The oligonucleotide is immobilized in wells of a microwell plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labeled ddNTPs specific for the expected next base. Readout may be fluorescent or ELISA-based. A signal indicates presence of the insert/flanking sequence due to successful amplification, hybridization, and single base extension.

Another method is the Pyrosequencing technique as described by Winge (Innov. Pharma. Tech. 00:18-24, 2000). In this method an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. DNTPs are added individually and the incorporation results in a light signal that is measured. A light signal indicates the presence of the transgene insert/flanking sequence due to successful amplification, hybridization, and single or multi-base extension.

Fluorescence Polarization is another method that can be used to detect an amplicon of the present invention. Following this method, an oligonucleotide is designed which overlaps the genomic flanking and inserted DNA junction. The oligonucleotide is hybridized to single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization, and single base extension.

TAQMAN® (PE Applied Biosystems, Foster City, Calif.) is a method of detecting and quantifying the presence of a DNA sequence. Briefly, a FRET oligonucleotide probe is designed that overlaps the genomic flanking and insert DNA junction. The FRET probe and PCR primers (one primer in the insert DNA sequence and one in the flanking genomic sequence) are cycled in the presence of a thermostable polymerase and dNTPs. During specific amplification, Taq DNA polymerase cleans and releases the fluorescent moiety away from the quenching moiety on the FRET probe. A fluorescent signal indicates the presence of the flanking/transgene insert sequence due to successful amplification and hybridization.

Molecular Beacons have been described for use in sequence detection. Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking genomic/transgene insert sequence due to successful amplification and hybridization.

Having disclosed a location in the soybean genome that is excellent for an insertion, the subject invention also comprises a soybean seed and/or a soybean plant comprising at least one non-soybean event pDAB9582.814.19.1:: pDAB4468.04.16.1 insert in the general vicinity of this genomic location. One option is to substitute a different insert in place of the ones from soybean event pDAB9582.814.19.1::pDAB4468.04.16.1 exemplified herein. In these general regards, targeted homologous recombination, for example, can be used according to the subject invention. This type of technology is the subject of, for example, WO 03/080809 A2 and the corresponding published U.S. application (US 20030232410). Thus, the subject invention includes plants and plant cells comprising a heterologous insert (in place of or with multi-copies of the aad-12, cry1F, cry1Ac, or pat genes), flanked by all or a recognizable part of the flanking sequences identified herein (bp 1-1400 of SEQ ID NO:1 and bp 153-1550 of SEQ ID NO:2 and bp 1-2730 of SEQ ID NO:15 and bp 9122-10,198 of SEQ ID NO:15). An additional copy (or additional copies) of a aad-12, cry1F, cry1Ac, or pat could also be targeted for insertion in this/these manner(s).

All patents, patent applications, provisional applications, and publications referred to or cited herein are incorporated by reference in their entirety to the extent they are not inconsistent with the explicit teachings of this specification.

The following examples are included to illustrate procedures for practicing the invention and to demonstrate certain preferred embodiments of the invention. These examples should not be construed as limiting. It should be appreciated by those of skill in the art that the techniques disclosed in the following examples represent specific approaches used to illustrate preferred modes for its practice. However, those of skill in the art should, in light of the present disclosure, appreciate that many changes can be made in these specific embodiments while still obtaining like or similar results without departing from the spirit and scope of the invention. Unless otherwise indicated, all percentages are by weight and all solvent mixture proportions are by volume unless otherwise noted.

The following abbreviations are used unless otherwise indicated.
bp base pair
° C. degrees Celsius
DNA deoxyribonucleic acid
EDTA ethylenediaminetetraacetic acid
kb kilobase
μg microgram
μL microliter
mL milliliter
M molar mass
PCR polymerase chain reaction
PTU plant transcription unit
SDS sodium dodecyl sulfate
SSC a buffer solution containing a mixture of sodium chloride and sodium citrate, pH 7.0
TBE a buffer solution containing a mixture of Tris base, boric acid and EDTA, pH 8.3

Embodiments of the present invention are further defined in the following Examples. It should be understood that these Examples are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

The disclosure of each reference set forth herein is incorporated herein by reference in its entirety.

EXAMPLES

Example 1: Transformation and Selection of the Cr1F and Cry1Ac Soybean Event pDAB9582.814.19.1

Transgenic soybean (*Glycine max*) containing the soybean event pDAB9582.814.19.1 was generated through *Agrobacterium*-mediated transformation of soybean cotyledonary node explants. The disarmed *Agrobacterium* strain EHA101 (Hood et al., 1993), carrying the binary vector pDAB9582 (FIG. 1) containing the selectable marker, pat v6, and the genes of interest, cry1F v3 and cry1Ac synpro, within the T-strand DNA region, was used to initiate transformation. The DNA sequence for pDAB9582 is given in SEQ ID NO:3, which is annotated below in Table 1.

TABLE 1

Gene elements located on pDAB9582.

| bp (SEQ ID NO: 3) | Construct element | Reference |
|---|---|---|
| 272-1593 | AtUbi10 Promoter | Callis, et al., (1990) *J. Biol. Chem.*, 265: 12486-12493 |
| 1602-5048 | Cry1F | Referenced above |
| 5151-5607 | ORF23 3'UTR | U.S. Pat. No. 5,428,147 |
| 5671-6187 | CsVMV Promoter | Verdaguer et al., (1996) *Plant Mol. Biol.*, 31: 1129-1139 |
| 6197-9667 | Cry 1AC | Referenced above |
| 9701-10157 | ORF23 3'UTR | U.S. Pat. No. 5,428,147 |
| 10272-10788 | CsVMV Promoter | Verdaguer et al., (1996) *Plant Mol. Biol.*, 31: 1129-1139 |
| 10796-11347 | PAT | Wohlleben et al., (1988) *Gene* 70: 25-37 |
| 11450-12153 | ORF1 3'UTR | Huang et al., (1990) *J. Bacteriol.* 172: 1814-1822 |

*Agrobacterium*-mediated transformation was carried out using a modified procedure of Zeng et al. (2004). Briefly, soybean seeds (cv Maverick) were germinated on basal media and cotyledonary nodes were isolated and infected with *Agrobacterium*. Shoot initiation, shoot elongation, and rooting media were supplemented with cefotaxime, timentin and vancomycin for removal of *Agrobacterium*. Glufosinate selection was employed to inhibit the growth of non-transformed shoots. Selected shoots were transferred to rooting medium for root development and then transferred to soil mix for acclimatization of plantlets.

Terminal leaflets of selected plantlets were leaf painted with glufosinate to screen for putative transformants. The screened plantlets were transferred to the greenhouse, allowed to acclimate and then leaf-painted with glufosinate to reconfirm tolerance and deemed to be putative transformants. The screened plants were sampled and molecular analyses for the confirmation of the selectable marker gene and/or the gene of interest were carried out. $T_0$ plants were allowed to self fertilize in the greenhouse to give rise to $T_1$ seed.

This event, soybean event pDAB9582.814.19.1, was generated from an independent transformed isolate. The $T_1$ plants were backcrossed and introgressed into elite varieties over subsequent generations. The event was selected based on its unique characteristics such as single insertion site, normal Mendelian segregation, stable expression, and a superior combination of efficacy, including herbicide tolerance and agronomic performance. The following examples contain the data which were used to characterize soybean event pDAB9582.814.19.1.

Example 2: Characterization of Protein Expression in Soybean Event pDAB9582.814.19.1

The biochemical properties of the recombinant Cry1F, Cry1Ac, and PAT proteins expressed in soybean event pDAB9582.814.19.1 were characterized. Quantitative enzyme-linked immunosorbent assay (ELISA) is a biochemical assay known within the art that can be used to characterize the biochemical properties of the proteins and confirm expression of these proteins in soybean event pDAB9582.814.19.1.

Example 2.1: Expression of the PAT, Cry1F, and Cry1Ac Protein in Plant Tissues

Samples of soybean tissues were isolated from the test plants and prepared for expression analysis. The PAT protein was extracted from soybean plant tissues with a phosphate buffered saline solution containing the detergent Tween-20 (PBST) containing 0.5% Bovine Serum Albumin (BSA). The plant tissue was centrifuged; the aqueous supernatant was collected, diluted with appropriate buffer as necessary, and analyzed using an PAT ELISA kit in a sandwich format. The kit was used following the manufacturer's suggested protocol (Envirologix, Portland, Me.). This assay measured the expressed PAT protein.

The Cry1F protein was extracted from soybean plant tissues with a phosphate buffered saline solution containing the detergent Tween-20 (PBST). The plant tissue was centrifuged; the aqueous supernatant was collected, diluted with appropriate buffer as necessary, and analyzed using an Cry1F ELISA kit in a sandwich format. The kit was used following the manufacturer's suggested protocol (Strategic Diagnostics Inc., Newark, Del.). This assay measured the expressed Cry1F protein.

The Cry1Ac protein was extracted from soybean plant tissues with a phosphate buffered saline solution containing the detergent Tween-20 (PBST) containing 0.5% Bovine Serum Albumin (BSA). The plant tissue was centrifuged; the aqueous supernatant was collected, diluted with appropriate buffer as necessary, and analyzed using an Cry1Ac ELISA kit in a sandwich format. The kit was used following the manufacturer's suggested protocol (Strategic Diagnostics Inc., Newark, Del.). This assay measured the Cry1Ac protein.

Detection analysis was performed to investigate the expression stability and inheritability both vertically (between generations) and horizontally (between lineages within a generation) in soybean event pDAB9582.814.19.1.

Example 2.2: Expression of the PAT, Cry1F, and Cry1Ac Protein in Plant Tissues

Levels of Cry1F, Cry1Ac and PAT proteins were determined in Soybean Event pDAB9582.814.19.1. The soluble, extractable proteins were measured using a quantitative enzyme-linked immunosorbent assay (ELISA) method from soybean leaf tissue. From $T_2$ to $T_6$ generations Soybean Events pDAB9582.814.19.1, expression was stable (not segregating) and consistent across all lineages. Table 2 lists the mean expression level of the transgenic proteins in soybean event pDAB9582.814.19.1.

TABLE 2

Mean expression level of different transgenic proteins in soybean event pDAB9582.814.19.1.
Expression Level of Different Proteins (ng/cm$^2$)

| Event | Cry1F | Cry1 Ac | PAT |
|---|---|---|---|
| Soybean event pDAB9582.814.19.1 | 133 | 17.4 | 12 |

Example 3: Cloning and Characterization of DNA Sequence in the Insert and the Flanking Border Regions of Soybean Event pDAB9582.814.19.1

To characterize and describe the genomic insertion site, the sequence of the flanking genomic T-DNA border regions of soybean event pDAB9582.814.19.1 were determined. Genomic sequence of soybean event pDAB9582.814.19.1 was confirmed, comprising 1400 bp of 5' flanking border sequence (SEQ ID NO:1) and 1398 bp of 3' flanking border sequence (SEQ ID NO:2). PCR amplification based on the soybean event pDAB9582.814.19.1 border sequences validated that the border regions were of soybean origin and that the junction regions are unique sequences for soybean event pDAB9582.814.19.1. The junction regions could be used for event-specific identification of soybean event pDAB9582.814.19.1. In addition, the T-strand insertion site was characterized by amplifying a genomic fragment corresponding to the region of the identified flanking border sequences from the genome of untransformed soybean. Comparison of soybean event pDAB9582.814.19.1 with the untransformed genomic sequence revealed that a deletion of about 57 bp from the original locus resulted during the T-strand integration. Overall, the characterization of the insert and border sequence of soybean event pDAB9582.814.19.1 indicated that an intact copy of the T-strand from pDAB9582 was present in the soybean genome.

TABLE 3

List of primers and their sequences used in the confirmation of soybean genomic DNA in soybean event pDAB9582.814.19.1

| SEQ ID NO: | Primer Name | Size (bp) | Sequence (5' to 3') | Purpose |
|---|---|---|---|---|
| SEQ ID NO: 4 | 81419_FW3 | 30 | TTTCTCCTATCCGTC AAATAAATCTGCTCC | confirmation of 5' border genomic DNA, used with AtUbi10RV1 or RV2; with 5'IREnd-01 or 5'IREnd-02 |

TABLE 3-continued

List of primers and their sequences used in the confirmation of soybean genomic DNA in soybean event pDAB9582.814.19.1

| SEQ ID NO: | Primer Name | Size (bp) | Sequence (5' to 3') | Purpose |
|---|---|---|---|---|
| SEQ ID NO: 5 | 81419_RV1 | 27 | GGGTGATTTGGTGCCAAAAGTTATGTT | confirmation of 3' border genomic DNA, used with 3'PATEnd05 or 3'PATEnd06 |
| SEQ ID NO: 6 | 81419_RV2 | 24 | TGGAGGGTCATATCGCAAAAGACT | confirmation of 3' border genomic DNA, used with 3'PATEnd05 or 3'PATEnd06 |
| SEQ ID NO: 7 | 81419_RV3 | 24 | GTTCTGCGTCGTGGAGGGTCATAT | confirmation of 3' border genomic DNA, used with 3'PATEnd05 or 3'PATEnd06 |
| SEQ ID NO: 8 | 5'IREnd-01 | 29 | CGAGCTTTCTAATTTCAAACTATTCGGGC | confirmation of 5' border genomic DNA, used with 81419_FW3 |
| SEQ ID NO: 9 | 5'IREnd-02 | 30 | TCCTAGATCATCAGTTCATACAAACCTCCA | confirmation of 5' border genomic DNA, used with 81419_FW3 |
| SEQ ID NO: 10 | AtUbi10RV1 | 29 | CGGTCCTAGATCATCAGTTCATACAAACC | confirmation of 5' border genomic DNA, used with 81419_FW3 |
| SEQ ID NO: 11 | AtUbi10RV2 | 28 | CACTCGTGTTCAGTCCAATGACCAATAA | confirmation of 5' border genomic DNA, used with 81419_FW3 |
| SEQ ID NO: 12 | 3'PATEnd05 | 20 | GCTCCTCCAAGGCCAGTTAG | confirmation of 3' border genomic DNA, used with 81419_RV1, RV2 or RV3 |
| SEQ ID NO: 13 | 3'PATEnd06 | 20 | CCAGTTAGGCCAGTTACCCA | confirmation of 3' border genomic DNA, used with 81419_RV1, RV2 or RV3 |

TABLE 4

Conditions for standard PCR amplification of the border regions and event-specific sequences in soybean event pDAB9582.814.19.1.

| Target Sequence | Primer Set | PCR Mixture | Pre-denature (° C./min) | Denature (° C./sec.) | Extension (° C./min:sec) | Final Extension (° C./min) |
|---|---|---|---|---|---|---|
| 5' border | 81419_FW3/AtUbi10RV1 | D | 95/3 | 98/10 | 68/4:00 32 cycles | 72/10 |
| 5' border | 81419_FW3/5'IREnd-01 | D | 95/3 | 98/10 | 68/4:00 32 cycles | 72/10 |
| 3' border | 3'PATEnd05/81419_RV2 | D | 95/3 | 98/10 | 68/4:00 35 cycles | 72/10 |
| 3' border | 3'PATEnd05/81419_RV3 | D | 95/3 | 98/10 | 68/4:00 35 cycles | 72/10 |
| 3' border | 3'PATEnd06/81419_RV2 | D | 95/3 | 98/10 | 68/4:00 35 cycles | 72/10 |
| 3'border | 3'PATEnd06/81419_RV3 | D | 95/3 | 98/10 | 68/4:00 32 cycles | 72/10 |
| Across the insert locus | 81419_FW3/81419_RV3 | D | 95/3 | 98/10 | 68/4:00 32 cycles | 72/10 |

TABLE 5

PCR mixture for standard PCR amplification of the border regions and event specific sequences in soybean event pDAB9582.814.19.1.

| PCR Mixture A | | PCR Mixture B | |
|---|---|---|---|
| Reagent | 1 x reaction (µL) | Reagent | 1 x reaction (µL) |
| H20 | 0.8 | H20 | 14.6 |
| ACCPRIME PFX SUPERMIX | 20 | 10X LA TAQ BUFFER | 2 |
| — | — | MgCl2 (25 mM) | 0.6 |
| — | — | dNTP (2.5 uM) | 1.6 |
| 10 uM primer | 0.2 | 10 uM primer | 0.1 |
| gDNA digestion | 1 | gDN digestion | 1 |
| — | — | LA TAQ (5 U/ul) | 0.1 |
| rxn vol: | 22 | rxn vol: | 20 |

| PCR Mixture C | | PCR Mixture D | |
|---|---|---|---|
| Reagent | 1 x reaction (µL) | Reagent | 1 x reaction (µL) |
| H20 | 28 | H20 | 11.6 |
| 10X PCR buffer II (Mg-plus) | 5 | 10X PCR buffer II (Mg-plus) | 2 |
| MgCl$_2$ [25 mM] | 1.5 | MgCl$_2$ [25 mM] | 0.6 |
| dNTP [2.5 mM] | 8 | dNTP [2.5 mM] | 3.2 |
| Adaptor PCR primer (10 µM) | 1 | primer1 (10 µM) | 0.4 |
| GOI nested primer (10 µM) | 1 | primer2 (10 µM) | 0.4 |
| DNA binded Beads | 5 | DNA Template | 0.2 |
| LA TAQ (5 U/ul) | 0.5 | LA TAQ (5 U/ul) | 1.6 |
| rxn vol: | 50 | rxn vol: | 20 |

Example 3.1: Confirmation of Soybean Genomic Sequences

The 5' and 3' flanking borders aligned to a *Glycine max* whole genome shotgun sequence from chromosome 02, indicating that the transgene of soybean event pDAB9582.814.19.1 was inserted in soybean genome chromosome 02. To confirm the insertion site of soybean event pDAB9582.814.19.1 from the soybean genome, PCR was carried out with different pairs of primers (FIG. 2, Table 3, Table 4, and Table 5). Genomic DNA from soybean event pDAB9582.814.19.1 and other transgenic or non-transgenic soybean lines was used as a template. To confirm that the 5' border sequences are correct a primer designed to bind to the At Ubi10 promoter gene element, for example AtUbi10RV1, and a primer designed to bind to the cloned 5' end border on soybean genome chromosome 02, primer designated 81419_FW3, were used for amplifying the DNA segment that spans the At Ubi10 promoter gene element to 5' end border sequence. Similarly, for confirmation of the cloned 3' border sequence a pat specific primer, for example 3'PAT-End05, and three primers designed according to the cloned 3' end border sequence, designated 81419_RV1, 81419_RV2 and 81419_RV3, were used for amplifying DNA segments that span the pat gene to 3' border sequence. DNA fragments with expected sizes were amplified only from the genomic DNA of soybean event pDAB9582.814.19.1 with each primer pair, but not from DNA samples from other transgenic soybean lines or the non-transgenic control. The results indicate that the cloned 5' and 3' border sequences are the flanking border sequences of the T-strand insert for soybean event pDAB9582.814.19.1.

To further confirm the DNA insertion in the soybean genome, a PCR amplification spanning the soybean border sequences was completed on genomic DNA which did not contain the T-strand insert for soybean event pDAB9582.814.19.1. Primer 81419_FW3, designed according to the 5' end border sequence, and one primer 81419-RV3, designed for the 3' end border sequence, were used to amplify DNA segments which contained the locus where the pDAB9582 T-strand integrated. As expected, PCR amplification completed with the primer pair of 81419_FW3 and 81419_RV3 produced an approximately a 1.5 kb DNA fragment from all the other soybean control lines but not pDAB9582.814.19.1. Aligning the identified 5' and 3' border sequences of soybean event pDAB9582.814.19.1 with a *Glycine max* whole genome shotgun sequence from chromosome 02 revealed about 57 bp deletion from the original locus. (FIG. 3). These results demonstrated that the transgene of soybean event pDAB8294 was inserted into the site of soybean genome chromosome 02.

Example 4: Soybean Event pDAB9582.814.19.1 Characterization Via Southern Blot

Southern blot analysis was used to establish the integration pattern of soybean event pDAB9582.814.19.1. These experiments generated data which demonstrated the integration and integrity of the cry1Ac and cry1F transgenes within the soybean genome. Soybean event pDAB9582.814.19.1 was characterized as a full length, simple integration event containing a single copy of the cry1Ac and cry1F plant transcription unit (PTU) from plasmid pDAB9582.

Southern blot data suggested that a T-strand fragment inserted into the genome of soybean event pDAB9582.814.19.1. Detailed Southern blot analysis was conducted using probes specific to the cry1Ac and cry1F gene, contained in the T-strand integration region of pDAB9582.814.19.1, and descriptive restriction enzymes that have cleavage sites located within the plasmid and produce hybridizing fragments internal to the plasmid or fragments that span the junction of the plasmid with soybean genomic DNA (border fragments). The molecular weights indicated from the Southern hybridization for the combination of the restriction enzyme and the probe were unique for the event, and established its identification patterns. These analyses also showed that the plasmid fragment had been inserted into soybean genomic DNA without rearrangements of the cry1Ac and cry1F PTU.

Example 4.1: Soybean Leaf Sample Collection and Genomic DNA (gDNA) Isolation

Genomic DNA was extracted from leaf tissue harvested from individual soybean plants containing soybean event pDAB9582.814.19.1. In addition, gDNA was isolated from a conventional soybean plant, Maverick, which contains the genetic background that is representative of the substance line, absent the cry1Ac and cry1F genes. Individual genomic DNA was extracted from lyophilized leaf tissue following the standard CTAB method (Sambrook et al (1989)). Following extraction, the DNA was quantified spectrofluorometrically using PICO GREEN reagent (Invitrogen, Carlsbad, Calif.). The DNA was then visualized on an agarose gel to confirm values from the PICO GREEN analysis and to determine the DNA quality.

Example 4.2: DNA Digestion and Separation

For Southern blot molecular characterization of soybean event pDAB9582.814.19.1, ten micrograms (10 μg) of genomic DNA was digested. Genomic DNA from the soybean event pDAB9582.814.19.1 and non-transgenic soybean line Maverick was digested by adding approximately five units of selected restriction enzyme per μg of DNA and the corresponding reaction buffer to each DNA sample. Each sample was incubated at approximately 37° C. overnight. The restriction enzymes AseI, HindIII, NsiI, and NdeI were used individually for the single digests (New England Biolabs, Ipswich, Mass.). The restriction enzymes NotI and ApaLI were used together for a double digestion (New England Biolabs, Ipswich, Mass.). In addition, a positive hybridization control sample was prepared by combining plasmid DNA, pDAB9582 with genomic DNA from the non-transgenic soybean variety, Maverick. The plasmid DNA/genomic DNA cocktail was digested using the same procedures and restriction enzyme as the test samples.

After the digestions were incubated overnight, 25 μL QUICK-PRECIP PLUS SOLUTION (Edge Biosystems, Gaithersburg, Md.) was added and the digested DNA samples were precipitated with isopropanol. The precipitated DNA pellet was resuspended in 15 μL, of 1× loading buffer (0.01% bromophenol blue, 10.0 mM EDTA, 10.0% glycerol, 1.0 mM Tris pH 7.5). The DNA samples and molecular size markers were then electrophoresed through 0.85% agarose gels with 0.4×TAE buffer (Fisher Scientific, Pittsburgh, Pa.) at 35 volts for approximately 18-22 hours to achieve fragment separation. The gels were stained with ethidium bromide (Invitrogen, Carlsbad, Calif.) and the DNA was visualized under ultraviolet (UV) light.

Example 4.3: Southern Transfer and Membrane Treatment

Southern blot analysis was performed essentially as described by Memelink, et al. (1994). Briefly, following electrophoretic separation and visualization of the DNA fragments, the gels were depurinated with 0.25M HCl for approximately 20 minutes, and then exposed to a denaturing solution (0.4 M NaOH, 1.5 M NaCl) for approximately 30 minutes followed by neutralizing solution (1.5 M NaCl, 0.5 M Tris pH 7.5) for at least 30 minutes. Southern transfer was performed overnight onto nylon membranes using a wicking system with 10×SSC. After transfer the DNA was bound to the membrane by UV crosslinking following by briefly washing membrane with a 2×SSC solution. This process produced Southern blot membranes ready for hybridization.

Example 4.4: DNA Probe Labeling and Hybridization

The DNA fragments bound to the nylon membrane were detected using a labeled probe (Table 6). Probes were generated by a PCR-based incorporation of a digoxigenin (DIG) labeled nucleotide, [DIG-11]-dUTP, into the DNA fragment amplified from plasmid pDAB9582 using primers specific to gene elements. Generation of DNA probes by PCR synthesis was carried out using a PCR DIG Probe Synthesis Kit (Roche Diagnostics, Indianapolis, Ind.) following the manufacturer's recommended procedures. Labeled probes were analyzed by agarose gel electrophoresis to determine their quality and quantity. A desired amount of labeled probe was then used for hybridization to the target DNA on the nylon membranes for detection of the specific fragments using the procedures essentially as described for DIG EASY HYB SOLUTION (Roche Diagnostics, Indianapolis, Ind.). Briefly, nylon membrane blots containing fixed DNA were briefly washed with 2×SSC and pre-hybridized with 20-25 mL of pre-warmed DIG EASY HYB SOLUTION in hybridization bottles at approximately 45-55° C. for about 2 hours in a hybridization oven. The pre-hybridization solution was then decanted and replaced with ~15 mL of pre-warmed DIG EASY HYB SOLUTION containing a desired amount of specific probes denatured by boiling in a water bath for approximately five minutes. The hybridization step was then conducted at approximately 45-55° C. overnight in the hybridization oven.

At the end of the probe hybridization, DIG EASY HYB SOLUTIONS containing the probes were decanted into clean tubes and stored at approximately −20° C. These probes could be reused up to two times according to the manufacturer's recommended procedure. The membrane blots were rinsed briefly and washed twice in clean plastic containers with low stringency wash buffer (2×SSC, 0.1% SDS) for approximately five minutes at room temperature, followed by washing twice with high stringency wash buffer (0.1×SSC, 0.1% SDS) for 15 minutes each at approximately 65° C. The membrane blots briefly washed with 1× Maleic acid buffer from the DIG WASH AND BLOCK BUFFER SET (Roche Diagnostics, Indianapolis, Ind.) for approximately 5 minutes. This was followed by blocking in a 1× blocking buffer for 2 hours and an incubation with anti-DIG-AP (alkaline phosphatase) antibody (Roche Diagnostics, Indianapolis, Ind.) in 1× blocking buffer also for a minimum of 30 minutes. After 2-3 washes with 1× washing buffer, specific DNA probes remain bound to the membrane blots and DIG-labeled DNA standards were visualized using CDP-STAR CHEMILUMINESCENT NUCLEIC ACID DETECTION SYSTEM (Roche Diagnostics, Indianapolis, Ind.) following the manufacturer's recommendation. Blots were exposed to chemiluminescent film for one or more time points to detect hybridizing fragments and to visualize molecular size standards. Films were developed with an ALL-PRO 100 PLUS film developer (Konica Minolta, Osaka, Japan) and images were scanned. The number and sizes of detected bands were documented for each probe. DIG-LABELED DNA MOLECULAR WEIGHT MARKER II (DIG MWM II) and DIG-LABELED DNA MOLECULAR WEIGHT MARKER VII (DIG MWM VII), visible after DIG detection as described, were used to determine hybridizing fragment size on the Southern blots.

TABLE 6

Location and length of probes used in Southern analysis.

| Probe Name | Genetic Element | Length (bp) |
| --- | --- | --- |
| Cry1Ac | cry1Ac | 1720 |
| Cry1F | cry1F | 1746 |
| specR | Spectinomycin resistance gene | 750 |
| OriRep | Ori Rep | 852 |
| trfA | Replication initiation protein trfA | 1119 |

Example 4.5: Southern Blot Results

Expected and observed fragment sizes with a particular digest and probe, based on the known restriction enzyme sites of the cry1Ac and cry1F PTU, are given in Table 7. Two types of fragments were identified from these digests and hybridizations: internal fragments where known enzyme sites flank the probe region and are completely contained within the insertion region of the cry1Ac and cry1F PTU, and border fragments where a known enzyme site is located at one end of the probe region and a second site is expected in the soybean genome. Border fragment sizes vary by event because, in most cases, DNA fragment integration sites are unique for each event. The border fragments provide a means to locate a restriction enzyme site relative to the integrated DNA and to evaluate the number of DNA insertions. Southern blot analyses completed on multiple generations of soybean containing soybean event pDAB9582.814.19.1 produced data which suggested that a low copy, intact cry1Ac and cry1F PTU from plasmid pDAB9582 was inserted into the soybean genome of soybean event pDAB9582.814.19.1.

TABLE 7

Predicted and observed hybridizing fragments in Southern blot analysis.

| DNA Probe | Restriction Enzymes | Samples | Expected Fragment Sizes (bp)[1] | Observed Fragment Size (bp)[2] |
|---|---|---|---|---|
| Cry1Ac | AseI | pDAB9582 | 13476 | >14000 |
| | | Maverick | none | none |
| | | Soybean Event pDAB9582.814.19.1 | >7286 | ~7400 |
| | Nsi I | pDAB9582 | 15326 | >15000 |
| | | Maverick | none | none |
| | | Soybean Event pDAB9582.814.19.1 | >9479 | >10000 |
| | Not I + ApaLI | pDAB9582 | 4550 | ~4500 |
| | | Maverick | none | none |
| | | Soybean Event pDAB9582.814.19.1 | 4550 | ~4500 |
| Cry1F | NdeI | pDAB9582 | 8071 | ~8000 |
| | | Maverick | none | none |
| | | Soybean Event pDAB9582.814.19.1 | 5569 | ~7500 |
| | Nsi I | pDAB9582 | 11044 | 11000 |
| | | Maverick | none | none |
| | | Soybean Event pDAB9582.814.19.1 | >9479 | >10000 |
| | Hind III | pDAB9582 | 7732 | ~7700 |
| | | Maverick | none | none |
| | | Soybean Event pDAB9582.814.19.1 | 7732 | ~7700 |
| SpecR | NsiI | pDAB9582 | 15320 | ~15000 |
| | | Maverick | none | none |
| | | Soybean Event pDAB9582.814.19.1 | none | none |
| trfA | NsiI | pDAB9582 | 15320 | ~15000 |
| | | Maverick | none | none |
| | | Soybean Event pDAB9582.814.19.1 | none | none |
| oriREP | NdeI | pDAB9582 | 5239 | ~5000 |
| | | Maverick | none | none |
| | | Soybean Event pDAB9582.814.19.1 | none | none |

[1]Expected fragment sizes are based on the plasmid map of pDAB9582.
[2]Observed fragment sizes are considered approximately from these analyses and are based on the indicated sizes of the DIG-LABELED DNA MOLECULAR WEIGHT MARKER II and MARK VII fragments.

The restriction enzymes AseI and NsiI bind and cleave unique restriction sites in plasmid pDAB9582. Subsequently, these enzymes were selected to characterize the cry1Ac gene insert in soybean event pDAB9582.814.19.1. Border fragments of >7286 bp or >9479 bp were predicted to hybridize with the probe following AseI and NsiI digests, respectively (Table 7). Single cry1Ac hybridization bands of about 7400 and >10000 bp were observed when AseI and NsiI digests were used, respectively. The hybridization of the probe to bands of this size suggests the presence of a single site of insertion for the cry1Ac gene in the soybean genome of soybean event pDAB9582.814.19.1. Restriction enzymes NotI and ApaLI were selected to perform a double digestion and to release a fragment which contains the cry1Ac plant transcription unit (PTU; promoter/gene/terminator) (Table 7). The predicted 4550 bp fragments were observed with the probe following NotI and ApaLI double digestion. Results obtained with the enzyme digestion of the pDAB9582.814.19.1 samples followed by probe hybridization indicated that an intact cry1Ac PTU from plasmid pDAB9582 was inserted into the soybean genome of soybean event pDAB9582.814.19.1.

The restriction enzymes NdeI and NsiI bind and cleave restriction sites in plasmid pDAB9582. Subsequently, these enzymes were selected to characterize the cry1F gene insert in soybean event pDAB9582.814.19.1. Border fragments of >5569 bp and >9479 were predicted to hybridize with the probe following the NdeI and NsiI digests, respectively (Table 7). Single cry1F hybridization bands of ~7500 bp and >10000 bp were observed when NdeI and NsiI were used, respectively. The hybridization of the probe to bands of this size suggests the presence of a single site of insertion for the cry1F gene in the soybean genome of soybean event pDAB9582.814.19.1. Restriction enzyme, HindIII, was selected to release a fragment which contains the cry1F plant transcription unit (PTU; promoter/gene/terminator) (Table 7). The predicted 7732 bp fragment was observed with the probe following the HindIII digestions. Results obtained with the enzyme digestion of the pDAB9582.814.19.1 samples followed by probe hybridization indicated that an intact cry1F PTU from plasmid pDAB9582 was inserted into the soybean genome of soybean event pDAB9582.814.19.1.

Example 4.6: Absence of Backbone Sequences

Southern blot analysis was also conducted to verify the absence of the spectinomycin resistance gene (specR), Ori Rep element and replication initiation protein trfA (trf A element) in soybean event pDAB9582.814.19.1. No specific hybridization to spectinomycin resistance, Ori Rep element or trf A element is expected when appropriate positive (pDAB9582 added to Maverick genomic DNA) and negative (Maverick genomic DNA) controls are included for Southern analysis. Following the NsiI digestion and hybridization with the specR specific probe, one expected size band of 15320 bp was observed in the positive control sample (pDAB9582 added to Maverick genomic DNA). The specR probe did not hybridize to samples of the negative control and soybean event pDAB9582.814.19.1. Similarly, one expected size band of 15320 bp was detected in the positive control sample (pDAB9582 plus maverick) but absent from the samples of the negative control and soybean event pDAB9582.814.19.1 after NsiI digestion and hybridization with trfA probe. Another expected size band of 5329 bp was detected in the positive control sample (pDAB9582 added to Maverick genomic DNA) but absent from the samples of the negative control and soybean event pDAB9582.814.19.1 after NdeI digestion and hybridization with OriRep specific probe. These data indicate the absence of spectinomycin resistance gene, Ori Rep element and replication initiation protein trfA in soybean event pDAB9582.814.19.1.

Example 5: Agronomic and Yield Field Trial and Herbicide Tolerance

To test the agronomic characteristics and efficacy of soybean event pDAB9582.814.19.1 the event was planted in an efficacy trial at Santa Isabel, Puerto Rico in October 2010 and February 2011. The cultivar Maverick, which was originally transformed to produce event pDAB9582.814.19.1, was planted in each nursery and included as a control in the experiments. Seed for the T3 nursery was derived from single plant selections at the T2 stage and seed for the T4 nursery was derived from single plant selections at the T3 stage. Four lineages of the event were tested each generation. Each lineage was planted in a plot which was 4 rows wide and 7.5 feet long. The spacing between rows was 30 inches. Plots were grown under lights for approximately 2.5 weeks to compensate for the short day length in Puerto Rico. Each nursery was sprayed with glufosinate at a rate of 411 g ae/ha. One plot of the control plants, Maverick, was sprayed with the same rate of glufosinate and a second plot was non-sprayed and used as control comparison for the event.

Data was collected on emergence, general appearance, vigor, height, lodging, and maturity. Herbicide tolerance was assessed by visually looking for chlorosis, leaf necrosis and plant death (Table 8).

For comparisons of soybean event pDAB9582.814.19.1 with Maverick, only data from the unsprayed block of Maverick were used. For comparison of the sprayed and non-sprayed treatments, data from the soybean event pDAB9582.814.19.1 block sprayed with a given treatment were compared with data from the Maverick control non-sprayed block. Soybean event pDAB9582.814.19.1 showed tolerance to the glufosinate herbicide application. In contrast, none of the Maverick plants were tolerant to the herbicide treatments.

rated 4 days after infestation. Larvae that were not responsive to gentle probing were considered dead. Leaf damage was assessed by visually scoring the percentage of leaf punch consumed by the insect.

Field evaluations were conducted by collecting leaf samples from seed increase nursery plots in Santa Isabel, Puerto Rico and sending these leaves to Indianapolis, Ind. for testing. The nursery plot for soybean event pDAB9582.814.19.1 was planted in February 2011 and consisted of approximately 180 plants arranged in four rows. Each row was 2.3 m long and spaced 76.2 cm apart; individual plants were spaced 5.1 cm apart within each row. In March 2011, one fully-expanded, mainstem trifoliate leaf, located approximately four nodes below the meristem, was excised from 10 soybean event pDAB9582.814.19.1 plants and 10 'Maverick' plants. The leaves were placed in labeled plastic bags, (one per bag) and sealed. The bagged leaves were packed and transferred to the laboratory. In the laboratory, one or two 3.33 cm (1.31 in) diameter leaf discs were punched from each trifoliate leaf to provide a total of 16 leaf discs. Each leaf disc was placed a in test arena on top of 2% agar, infested with one neonate *S. frugiperda* larva, and sealed with a perforated plastic lid. The leaf discs were held in a controlled environment chamber for 7 days, at which time mortality and leaf consumption were rated. Larvae not responsive to gentle probing were considered dead. Leaf damage was assessed by visually scoring the percentage of leaf punch consumed by the insect.

The results obtained from these replicated experiments indicated the soybean event pDAB9582.814.19.1 sustained significantly lower damage than the Maverick control plants

TABLE 8

Comparison of soybean event pDAB9582.814.19.1 to Maverick. Values are averages from $T_3$ and $T_4$ nurseries. Each nursery of soybean event pDAB9582.814.19.1 was sprayed with glufosinate at the V3 stage at a rate of 411 g ae/ha.

| Event | Emergence (%) | Appearance (1 = poor to 9 = good) | Vigor (1 = poor to 9 = good) | Height (cm) | Lodging (%) | Maturity (day) |
| --- | --- | --- | --- | --- | --- | --- |
| pDAB9582.814.19.1 | 90 | 8 | 8 | 69 | 1 | 91 |
| Maverick | 82 | 8 | 8 | 64 | 1 | 91 |

Example 6: Characterization of Insecticidal Activity for Soybean Event pDAB9582.814.19.1

Field and greenhouse evaluations were conducted to characterize the activity of Cry1Ac and Cry1F in soybean event pDAB9582.814.19.1 against lab reared soybean pests including *Anticarsia gemmatalis* (velvetbean caterpillar), *Pseudoplusia includens* (soybean looper) and *Spodoptera frugiperda* (fall armyworm). Soybean event pDAB9582.814.19.1 was compared against non-transformed soybean variety Maverick, to determine the level of plant protection provided by the Cry1F and Cry1 Ac proteins.

Greenhouse trials were conducted on approximately four week old plants. Fifteen plants were used to evaluate the soybean event pDAB9582.814.19.1 and the Maverick control. For each insect species tested (*Anticarsia gemmatalis*, *Pseudoplusia includes*, and *Spodoptera frugiperda*) 3 leaf punches were made from each plant for a total of 45 leaf discs/plant/insect species. The 1.4 cm diameter (or 1.54 cm$^2$) leaf punches were placed in a test arena on top of 2% water agar, infested with one neonate larvae and sealed with a perforated plastic lid. Mortality and leaf consumption were for all insects tested. Thus, the soybean event pDAB9582.814.19.1 has insecticidal activity over this broad host range.

Example 7: Sequence of Soybean Event pDAB9582.814.19.1

SEQ ID NO:14 provides the sequence of soybean event pDAB9582.814.19.1. This sequence contains the 5' genomic flanking sequence, the T-strand insert of pDAB9582 and 3' genomic flanking sequences. With respect to SEQ ID NO:14, residues 1-1400 are 5' genomic flanking sequence, residues 1401-1536 are residues of a rearrangement from the pDAB9582 plasmid and 1537-13896 are residues of the pDAB9582 T-strand insert, and residues 13897-15294 are 3' flanking sequence. The junction sequence or transition with respect to the 5' end of the insert thus occurs at residues 1400-1401 of SEQ ID NO:14. The junction sequence or transition with respect to the 3' end of the insert thus occurs at residues 13896-13897 of SEQ ID NO:14.

It should be noted that progeny from soybean event pDAB9582.814.19.1 may have sequences which slightly deviate from SEQ ID NO:14. During the introgression and breeding process of introducing soybean event pDAB9582.814.19.1 into the genome of plant cells, it is not uncommon for some deletions or other alterations of the insert to occur. Moreover, errors in PCR amplification can occur which might result in minor sequencing errors. For example, flanking sequences listed herein were determined by generating amplicons from soybean genomic DNAs, and then cloning and sequencing the amplicons. It is not unusual to find slight differences and minor discrepancies in sequences generated and determined in this manner, given the many rounds of amplification that are necessary to generate enough amplicon for sequencing from genomic DNAs. One skilled in the art should recognize and be put on notice that any adjustments needed due to these types of common sequencing errors or discrepancies are within the scope of the subject invention. Thus, the relevant segment of the plasmid sequence provided herein might comprise some minor variations. Thus, a plant comprising a polynucleotide having some range of identity with the subject insert sequence is within the scope of the subject invention. Identity to the sequence of SEQ ID NO:14 can be a polynucleotide sequence having at least 90%, 91%, 92%, 93%, 94%, 95%, 96%, 97%, 98%, 99%, or 100% sequence identity with a sequence exemplified or described herein. Thus, some differences between SEQ ID NO:14 and soybean event pDAB9582.814.19.1 progeny plants may be identified and are within scope of the present invention.

Example 8: Breeding Stack Soybean Event pDAB4468.04.16.1 and Soybean Event pDAB9582.814.19.1

Example 8.1: Sexual Crossing of Soybean Event pDAB4468.04.16.1 and Soybean Event pDAB9582.814.19.1

Soybean event pDAB4468.04.16.1 as described in International Patent Application No. WO/2012/075426 was sexually crossed with soybean event pDAB9582.814.19.1. The anthers of soybean event pDAB4468.04.16.1 were manually rubbed across the stigma of soybean event pDAB9582.814.19.1, thereby fertilizing soybean event pDAB9582.814.19.1. The resulting $F_1$ progeny which contained integration events from both soybean event pDAB9582.814.19.1 and soybean event pDAB4468.04.16.1 were screened for tolerance to 2,4-D and glufosinate herbicides to identify progeny plants which contained both integration events.

Example 8.2: Characterization of Protein Expression in the Breeding Stack Soybean Event pDAB9582.814.19.1::pDAB4468.04.16.1

The biochemical properties of the recombinant Cry1F, Cry 1Ac, AAD12 and PAT proteins expressed in the breeding stack soybean event pDAB9582.814.19.1::pDAB8264.44.06.1 were characterized. A total of 51 $F_1$ plants were confirmed to contain both soybean event pDAB9582.814.19.1 and pDAB4468.04.16.1 by event specific TAQMAN® assays, using assays based on those disclosed at U.S. Provisional Patent Application No. 61/511,658 and International Patent Application No. WO/2011/066360, respectively. Next, an enzyme linked immunosorbent assay (ELISA) was used to quantify the expression of PAT and AAD12 proteins whereas Cry1Ac and Cry1F proteins were quantified by multiplexed immunoassays utilizing electrochemiluminescent technology from Meso-Scale Discovery (MSD). Collectively, these assays were used to characterize the biochemical properties of the proteins and confirm expression of these proteins in the breeding stack soybean event pDAB9582.814.19.1::pDAB4468.04.16.1.

Expression of the PAT Protein in Plant Tissues

Levels of PAT protein were determined in the breeding stack soybean event pDAB9582.814.19.1::pDAB4468.04.16.1. The soluble, extractable PAT protein was measured using a quantitative enzyme-linked immunosorbent assay (Envirologix, Portland, Me.) for testing soybean leaf tissue.

A total of 51 $F_1$ plants were confirmed to contain both soybean event pDAB9582.814.19.1 and pDAB4468.04.16.1 by event specific TAQMAN® assays. Samples of soybean leaf tissue were isolated from these greenhouse grown test plants at the V3-V4 growth stage and prepared for expression analysis. The PAT protein was extracted from the soybean plant tissues with a phosphate buffered saline solution containing the detergent Tween-20 (PBST) and 1% polyvinylpyrrolidone 40 (PVP-40). The samples were then extracted using a GENOGRINDER™ at 1500 rpm for 5 minutes. The plant extract was centrifuged; the aqueous supernatant was collected, diluted with appropriate buffer as necessary, and analyzed using an PAT ELISA kit in a sandwich format. The kit was used following the manufacturer's suggested protocol. This assay measured the expressed PAT protein in the leaf tissue.

Detection analysis was performed to investigate the expression heritability in the breeding stack soybean event pDAB9582.814.19.1::pDAB4468.04.16.1. At the F1 generation, plants of the breeding stack soybean event pDAB9582.814.19.1::pDAB4468.04.16.1 expressed PAT (Table 9).

TABLE 9

Average PAT Expression in the breeding stack soybean event pDAB9582.814.19.1::pDAB4468.04.16.1

| Event | Average PAT Expression (ng/cm$^2$) |
|---|---|
| pDAB9582.814.19.1::pDAB4468.04.16.1 | 3.99 |

Expression of the Cry1F and Cry1Ac Proteins in Plant Tissues

Levels of Cry1F and Cry1Ac proteins were determined in the breeding stack soybean event pDAB9582.814.19.1::pDAB4468.04.16.1. The soluble, extractable Cry1F and Cry1Ac proteins were measured using a multiplexed MSD assay (Meso-Scale Discovery, Gaithersburg, Md.) for soybean leaf tissue.

A total of 51 $F_1$ plants were confirmed to contain both soybean event pDAB9582.814.19.1 and pDAB4468.04.16.1 by event specific TAQMAN® assays. Samples of soybean leaf tissue were isolated from these greenhouse grown test plants at the V3-V4 growth stage and prepared for expression analysis. The Cry1F and Cry1Ac proteins were extracted from the soybean plant tissues with PBST and 1% PVP40. The samples were then extracted using a GENOGRINDER™ at 1500 rpm for 5 minutes. The plant extract was centrifuged; the aqueous supernatant was collected, diluted with appropriate buffer as necessary, and analyzed using a Cry1F/Cry1Ac multiplex MSD assay from Meso-Scale Discovery. This assay measured the Cry1F and Cry1Ac protein in the leaf tissue.

Detection analysis was performed to investigate the expression heritability in the breeding stack soybean event pDAB9582.814.19.1::pDAB4468.04.16.1. At the $F_1$ generation, plants of the breeding stack soybean event pDAB9582.814.19.1::pDAB4468.04.16.1 expressed Cry1F and Cry1Ac (Table 10).

TABLE 10

Average Cry1F and Cry1Ac Expression in the breeding stack soybean event pDAB9582.814.19.1::pDAB4468.04.16.1

| Event | Average Cry1F Expression (ng/cm$^2$) | Average Cry1Ac Expression (ng/cm$^2$) |
|---|---|---|
| pDAB9582.814.19.1::pDAB4468.04.16.1 | 139.73 | 33.90 |

Expression of the AAD12 Proteins in Plant Tissues

Levels of AAD12 protein were determined in the breeding stack soybean event pDAB9582.814.19.1::pDAB4468.04.16.1. The soluble, extractable AAD12 protein was measured using a quantitative enzyme-linked immunosorbent assay (Acadia Bioscience, Portland, Me.) for testing soybean leaf tissue.

A total of 51 $F_1$ plants were confirmed to contain both soybean event pDAB9582.814.19.1 and pDAB4468.04.16.1 by event specific TAQMAN® assays. Samples of soybean leaf tissue were isolated from these greenhouse grown test plants at the V3-V4 growth stage and prepared for expression analysis. The AAD12 protein was extracted from the soybean plant tissues with a phosphate buffered saline solution containing the detergent Tween-20 (PBST) and 0.5% bovine serum albumin (BSA). The samples were then extracted using a GENOGRINDER™ at 1500 rpm for 5 minutes. The plant extract was centrifuged; the aqueous supernatant was collected, diluted with appropriate buffer as necessary, and analyzed using an AAD12 ELISA kit in a sandwich format. The kit was used following the manufacturer's suggested protocol (Acadia, Portland, Me.). This assay measured the expressed AAD12 protein in the leaf tissue.

Detection analysis was performed to investigate the expression heritability in the breeding stack soybean event pDAB9582.814.19.1::pDAB4468.04.16.1. At the F1 generation, plants of the breeding stack soybean event pDAB9582.814.19.1::pDAB4468.04.16.1 expressed AAD12 (Table 11).

TABLE 11

Average AAD12 Expression in the breeding stack Soybean Event pDAB9582.814.19.1::pDAB4468.04.16.1

| Event | Average AAD12 Expression (ng/cm$^2$) |
|---|---|
| pDAB9582.814.19.1::pDAB4468.04.16.1 | 110.2 |

Example 8.3: Herbicide Tolerance of the Breeding Stack Soybean Event pDAB9582.814.19.1::pDAB4468.04.16.1

Herbicide tolerance of the breeding stack, soybean event pDAB9582.814.19.1::pDAB4468.04.16.1 was assayed in a greenhouse study. Soybean event pDAB9582.814.19.1::pDAB4468.04.16.1 seed were planted in pots and grown to maturity. Fifty-three (53) mature $F_1$ plants were sprayed with a single herbicide application which consisted of 840 g ae/ha 2,4-D at the V3-V4 growth stage (characterized by the unifoliate and first three to four trifoliate leaves being fully developed). The resulting tolerance to these herbicides was measured by counting the number of surviving plants. All fifty-three plants were found to be resistant to the herbicide application. Comparatively, control plants which did not contain the aad-12 gene and were expected to be susceptible to the application of the 2,4-D herbicides were included in the study.

In summary, the aad-12 gene which was present in the soybean event pDAB4468.04.16.1 parental line conferred tolerance to the 2,4-D herbicide. This trait was passed and inherited in soybean pDAB9582.814.19.1::pDAB4468.04.16.1, thereby providing herbicidal tolerance to soybean event pDAB9582.814.19.1::pDAB4468.04.16.1. Comparatively, control plants which did not contain the aad-12 gene were susceptible to the application of the 2,4-D herbicide.

Example 8.4: Characterization of Insecticidal Activity of Soybean Event pDAB9582.814.19.1::pDAB4468.04.16.1

Greenhouse evaluations were conducted to characterize the activity of Cry1Ac and Cry1F in the breeding stack soybean event pDAB9582.814.19.1::pDAB4468.04.16.1 against lab reared soybean pests including *Anticarsia gemmatalis* (velvetbean caterpillar) and *Pseudoplusia includens* (soybean looper). The breeding stack soybean event pDAB9582.814.19.1::pDAB4468.04.16.1 was compared against soybean event pDAB9582.814.19.1, soybean event pDAB4468.04.16.1 and non-transformed soybean variety Maverick, to determine if the level of plant protection provided by the Cry1F and Cry1 Ac proteins changes when stacked. In addition, the breeding stack soybean event pDAB9582.814.19.1::pDAB4468.04.16.1 and soybean event pDAB4468.04.16.1 were sprayed with a single herbicide application containing 840 g ae/ha 2,4-D prior to the bioassays to confirm the absence of negative biological impact from the herbicides against the insects.

Greenhouse trials were conducted on approximately three week old plants. Five to ten plants each were used to evaluate the breeding stack soybean event pDAB9582.814.19.1::pDAB4468.04.16.1, soybean event pDAB9582.814.19.1, and the negative controls: sprayed soybean event pDAB4468.04.16.1 and Maverick. For each insect species tested (*Anticarsia gemmatalis* and *Pseudoplusia includes*), 3 leaf punches were made from each plant per insect species. The 1.4 cm diameter (or 1.54 cm$^2$) leaf punches were placed in a test arena on top of 1.5% water agar, infested with one neonate larva and sealed with a perforated plastic lid. Mortality and leaf consumption were rated 4 days after infestation. Larvae that were not responsive to gentle probing were considered dead. Leaf damage was assessed by visually scoring the percentage of leaf area consumed by the insect.

The results obtained from these replicated experiments (Table 12) indicated that the breeding stack soybean event pDAB9582.814.19.1::pDAB4468.04.16.1 was consistent with soybean event pDAB9582.814.19.1 and sustained significantly lower damage to leaf tissue (0.6-0.8%) than soybean event pDAB4468.04.16.1 (94-99%) and Maverick (96-97%) controls against the soybean looper and velvetbean caterpillar. High mortality (100%) was recorded for both the breeding stack soybean event pDAB9582.814.19.1::pDAB4468.04.16.1 and soybean event pDAB9582.814.19.1 while the pDAB4468.04.16.1 and Maverick plants resulted in low mortality (0%) and all of the insects placed on these control plants survived. Thus, the breeding stack soybean event pDAB9582.814.19.1::pDAB4468.04.16.1 has comparable insecticidal activity to soybean event pDAB9582.814.19.1.

TABLE 12

Mean percent leaf damage and mortality of *Pseudoplusia includens*, soybean looper, (SBL) and *Anticarsia gemmatalis*, velvetbean caterpillar, (VBC) fed on various soybean event. (n = 15-24)

| Treatment | Insect | Mean % leaf damage at 4 DAI* | Mean % mortality |
|---|---|---|---|
| pDAB4468.04.16.1 | SBL | 99.2 | 0 |
| pDAB4468.04.16.1 | VBC | 93.7 | 0 |
| pDAB9582.814.19.1 | SBL | 0.6 | 100 |
| pDAB9582.814.19.1 | VBC | 0.6 | 100 |
| pDAB9582.814.19.1::pDAB4468.04.16.1 | SBL | 0.5 | 100 |
| pDAB9582.814.19.1::pDAB4468.04.16.1 | VBC | 0.8 | 100 |
| Maverick | SBL | 96.1 | 0 |
| Maverick | VBC | 96.8 | 0 |

*DAI = days after infestation

Having illustrated and described the principles of the present invention, it should be apparent to persons skilled in the art that the invention can be modified in arrangement and detail without departing from such principles. We claim all modifications that are within the spirit and scope of the appended claims.

All publications and published patent documents cited in this specification are incorporated herein by reference to the same extent as if each individual publication or patent application was specifically and individually indicated to be incorporated by reference.

The invention claimed is:

1. A method of controlling insects, said method comprising contacting insects with insect resistant soybean plants of event pDAB9582.814.19.1::pDAB4468.04.16.1, wherein said event comprises SEQ ID NO: 14, encoding cry1F, cry1Ac and phosphinothricin acetyltransferase (pat), and SEQ ID NO: 15, encoding aryloxyalkanoate dioxygenase-12 (aad-12) and pat, to thereby control insects selected from the group consisting of *Pseudoplusia includens, Anticarsia gemmatalis* and *Spodoptera frugiperda*.

2. The method of claim 1 wherein said insects are *Pseudoplusia includens*.

3. The method of claim 1 wherein said insects are *Anticarsia gemmatalis*.

4. The method of claim 1 wherein said insects are *Spodoptera frugiperda*.

5. A method of controlling weeds in an area comprising a soybean crop, said method comprising applying a glufosinate herbicide, a phenoxyacetic acid herbicide, a pyridyloxyacetic acid herbicide, or combinations thereof to said, wherein soybean plants of said soybean crop comprise event pDAB9582.814.19.1::pDAB4468.04.16.1, wherein said event comprises SEQ ID NO: 14, encoding cry1F, cry1Ac and pat, and SEQ ID NO: 15, encoding aad-12 and pat.

6. An isolated DNA molecule comprising one and more sequences selected from the group consisting of nucleotides 1385-1415 of SEQ ID NO: 1; nucleotides 1350-1450 of SEQ ID NO: 1; nucleotides 1300-1500 of SEQ ID NO: 1; nucleotides 1200-1600 of SEQ ID NO: 1; nucleotides 137-168 of SEQ ID NO:2; bp 103-203 of SEQ ID NO:2; and bp 3-303 of SEQ ID NO:2; or one or more sequences selected from the group consisting of nucleotides 2680-2780 of SEQ ID NO: 15; nucleotides 2630-2830 of SEQ ID NO:15; nucleotides 2530-2930 of SEQ ID NO:15; nucleotides 9071-9171 of SEQ ID NO:15; nucleotides 9021-9221 of SEQ ID NO: 15; and nucleotides 8921-9321 of SEQ ID NO: 15.

7. A method of breeding a soybean plant, comprising:
crossing a first soybean plant with a second soybean plant to produce a third soybean plant, wherein said first plant is a plant of event pDAB9582.814.19.1, wherein said event comprises SEQ ID NO: 14, encoding cry1F, cry1Ac and pat, and wherein said second plant is a plant of event pDAB4468.04.16.1, wherein said event comprises SEQ ID NO: 15, encoding aad-12 and pat; and
assaying said third soybean plant for presence of DNA comprising said SEQ ID NO: 14 and SEQ ID NO: 15.

8. An isolated DNA molecule comprising a junction sequence comprising at least one sequence selected from the group consisting of nucleotides 1385-1415 of SEQ ID NO:1; nucleotides 1350-1450 of SEQ ID NO:1; nucleotides 1300-1500 of SEQ ID NO:1; nucleotides 1200-1600 of SEQ ID NO:1; nucleotides 137-168 of SEQ ID NO:2; nucleotides 103-203 of SEQ ID NO:2; nucleotides 3-303 of SEQ ID NO:2 and full complements thereof; and comprising at least one sequence selected from the group consisting of bp 2680-2780 of SEQ ID NO:15; nucleotides 2630-2830 of SEQ ID NO: 15; nucleotides 2530-2930 of SEQ ID NO:15; nucleotides 9071-9171 of SEQ ID NO:15; nucleotides 9021-9221 of SEQ ID NO:15; nucleotides 8921-9321 of SEQ ID NO:15 and full complements thereof.

9. A soybean plant that is resistant to *Pseudoplusia includens*, wherein said plant comprises event pDAB9582.814.19.1::pDAB4468.04.16.1, wherein said event comprises SEQ ID NO: 14, encoding cry1F, cry1Ac and pat, and SEQ ID NO: 15, encoding aad-12 and pat.

10. A seed of the plant of claim 9, wherein said seed comprises said event.

11. Soybean meal produced from the plant of claim 9, wherein said meal comprises said event.

12. A method of controlling insect pests selected from the group consisting of *Pseudoplusia includens, Anticarsia gemmatalis*, and *Spodoptera frugiperda*, in soybean seed, meal, or flour, said method comprising contacting said insects with seed, meal, or flour that comprises event pDAB9582.814.19.1::pDAB4468.04.16.1, wherein said event comprises SEQ ID NO: 14 encoding cry1F, cry1Ac and pat, and SEQ ID NO: 15, encoding aad-12 and pat.

13. A part of the soybean plant of claim 9, wherein said part is selected from the group consisting of pollen, ovule, flowers, shoots, roots, and leaves, wherein said part comprises said event.

* * * * *

SEQUENCE LISTING

```
<160> NUMBER OF SEQ ID NOS: 15

<210> SEQ ID NO 1
<211> LENGTH: 1836
<212> TYPE: DNA
<213> ORGANISM: Glycine max

<400> SEQUENCE: 1
ttaacaatga ccaagattta tgctatatag aagacttgga gggcttaagg ctatgatata      60
ttatggatga tatggttctg atttgtgtag tttcgaagga tcaaatcaac catttgttgg     120
tacaatggga agaaaaaatg tttcatcat tccactctat tgaaaaagat ccaacaattg     180
taacaccccg acgaatcaca ccggaaagag aagaatccaa agattgtgta ggtatgagac     240
tgtatagttg atgaaaactt aaaaaaatta attggtacta cttataccaa caagatgcat     300
atatttttcg atagcctatc acataagaac ttcatagtta agggtgctta acttggagta     360
gttatgaaat gagtgacctt ttaaaataat tattgtctta ggttattgta tgaaaataaa     420
aaataataat aaatatacat aaaaaataat aattttataa aattaacctt atattatcat     480
taatttattt ttagattttg ttattcatta ttaatatatg aggtataaat gaaaaatata     540
attaatgtca cattaaaaaa ttaaaatgat aatttattttg aaacaaatta tttattttta     600
tacgacaatt ataatagaaa tttgagagta aaaaaaaatt gaaattcat aaaatatatg     660 aatatattca tttctcctat ccgtcaaata aatctgctcc ataatttatc taagcattgg     720
tcttgtagtt cagagtaata aaattttagc aattattagt tagtacagat acatttaaag     780
aaataatata ttttagcaac tagaagttta taaaaagttt taaattataa agacttatat     840
ataaatttag taaaactaga tggatgtccc aagtaatttt tatataacta ttctcgtaca     900
acattaatga aaatcttgtt tctattattt atatgtatat tattatttta ttttggaaca     960
atatgggatt aaaaactctt ataaattaaa tcttagaata agttttccta acatgttttt    1020
tttatggatg ttttcctaac atgttggtt atcttagttt tgctttaatt ttgtcggatt    1080 attttggac tttattaggt aattttgata aaacttttag ttgatgttag tagtttactc    1140
```

```
ttacataatg atttgatatt gaatgtgtat aattggaagg caataaatga agatcaagcg      1200
tacaagagtt cgccaatcaa gaggatttga agagagtaaa atattatgcg aagtcccatg      1260
tgaagaaaat ccaaccattg aataaaaaaa taaagttttt tctttggaat tgctaatgct      1320
acagcactta ttggtacttg tcctaaaaat gaaactctag ctatatttag cacttgatat      1380
tcatgaatca aacttctcta tgaaataacc gcggtgcgca tcggtgcctg ttgatcccgc      1440
gcaagtgggg atcttgaagc aagttccgct catcactaag tcgcttagca tgtttgacct      1500
tctcggacaa ctccttcttc tctttaattg atcaacagtc agcatcatca caccaaaagt      1560
taggcccgaa tagtttgaaa ttagaaagct cgcaattgag gtctacaggc caaattcgct      1620
cttagccgta caatattact caccggatcc taaccggtgt gatcatgggc cgcgattaaa      1680
aatctcaatt atatttggtc taatttagtt tggtattgag taaaacaaat tcggcgccat      1740
gcccgggcaa gcggccgcac aagtttgtac aaaaaagcag gctccgcggt gactgactga      1800
aaagcttgtc gacctgcagg tcaacggatc aggata                                1836
```

<210> SEQ ID NO 2
<211> LENGTH: 1550
<212> TYPE: DNA
<213> ORGANISM: Glycine max

<400> SEQUENCE: 2

```
gcacatagac acacacatca tctcattgat gcttggtaat aattgtcatt agattgtttt       60
tatgcataga tgcactcgaa atcagccaat tttagacaag tatcaaacgg atgtgacttc      120
agtacattaa aaacgtccgc aatatgatat tcattaattt tatattatct aaaagagtta      180
aaagagaaaa aagaaatatg acaattttt tctttcacat cttctaacct aaaagtatga      240
ctctatggag gctaagttta gaaaagata cggatctagg gtgtggaaac atcaatggtc      300
aactcctttt atatttcaat caattgggtt ttgctttatc tttacatttt ctccttttat      360
tttccacgtc tattcaaatc tacttgttag cgggtgatta ctcttttttc ttttatagat      420
gccaattatt tctctcctat gtattaaatt agagtatatt gtcttgaaag tgacttagta      480
ttttagttta tagtctctta aagaacgaca ccttttattc ttaactctct ttatcaagtt      540
ttaatttaaa attattttaa attaagtatg catacatatc ttaatatttt tcttaattat      600
ttttaaattc cctaaattta atgttttcat acaatgtaag agatatacat attaattata      660
tttaaagata aaacttactt tcctgcaata aaataaagaa aaggacagtc atacaattat      720
ataattaatc cagaatattt atagctttta aacatttatt ttctatcaat taagtaataa      780
ctttaaataa aattaagagt actttttat actccaaaga atttatttat tttcaacaaa      840
atcgtctgac tgtttcaatt gatcattatc agcctagcat aacctaaatt tcattttcaa      900
acataacttt tggcaccaaa tcacccggca ttgcaaaaaa gtcttttgcg atatgaccct      960
ccacgacgca gaaccactgt tattcattac catcactttt aatcctaatt tcccatacac     1020 ttacccttc catgacatct tcaaagcctt tattttgctt tcttgtttta agctgtttta     1080
acctaatttc atgcatataa acaaagagta aagcaaaggc aaatatttgt acgtatagtt     1140
tttagacaga aaaggaaagt aaattataga gataatgaag tttgctcttt taaattcgtc     1200
gtgatgttat ccatcatatc taaatgctta ttcctgtttt tgtcttttt ctctttacc     1260 ggagtttatt ttatataatt aattaaagtt agtagatcta tattcttttt catagataat     1320
ccatcttctt tggaggcaca tcgatcatta atcatagagt tttgagaagc attatcacta     1380
aagcttcaat taattatatc caataaacgg tattggtgta tgatgttatg atagcaaata     1440
```

```
gataatctaa tctatacgag ccacaaaagg ggcatgaact ctatctcgaa gaaattggag    1500
atgaagggat tgagattggc accttgtgct attattgccc actaatcatt              1550

<210> SEQ ID NO 3
<211> LENGTH: 12381
<212> TYPE: DNA
<213> ORGANISM: Artificial Sequence
<220> FEATURE:
<223> OTHER INFORMATION: Plasmid sequence of pDAB9582

<400> SEQUENCE: 3
agtcagcatc atcacaccaa aagttaggcc cgaatagttt gaaattagaa agctcgcaat      60
tgaggtctac aggccaaatt cgctcttagc cgtacaatat tactcaccgg atcctaaccg     120
gtgtgatcat gggccgcgat taaaaatctc aattatattt ggtctaattt agtttggtat     180
tgagtaaaac aaattcggcg ccatgcccgg gcaagcggcc gcacaagttt gtacaaaaaa     240
gcaggctccg cggtgactga ctgaaaagct tgtcgacctg caggtcaacg gatcaggata     300
ttcttgttta agatgttgaa ctctatggag gtttgtatga actgatgatc taggaccgga     360
taagttccct tcttcatagc gaacttattc aaagaatgtt ttgtgtatca ttcttgttac     420
attgttatta atgaaaaaat attattggtc attggactga acacgagtgt taaatatgga     480
ccaggcccca ataagatcc attgatatat gaattaaata acaagaataa atcgagtcac      540
caaaccactt gccttttta cgagacttg ttcaccaact tgatacaaaa gtcattatcc       600
tatgcaaatc aataatcata caaaaatatc aataacact aaaaaattaa aagaaatgga      660
taatttcaca atatgttata cgataaagaa gttacttttc caagaaattc actgatttta    720
taagcccact tgcattagat aaatggcaaa aaaaacaaa aaggaaaaga aataaagcac      780
gaagaattct agaaaatacg aaatacgctt caatgcagtg ggacccacgg ttcaattatt     840
gccaattttc agctccaccg tatatttaaa aaataaaacg ataatgctaa aaaaatataa     900
atcgtaacga tcgttaaatc tcaacggctg gatcttatga cgaccgttag aaattgtggt     960
tgtcgacgag tcagtaataa acggcgtcaa agtggttgca gccggcacac acgagtcgtg    1020
tttatcaact caaagcacaa atactttcc tcaacctaaa aataaggcaa ttagccaaaa     1080
acaactttgc gtgtaaacaa cgctcaatac acgtgtcatt ttattattag ctattgcttc    1140
accgccttag ctttctcgtg acctagtcgt cctcgtcttt tcttcttctt cttctataaa    1200 acaatacccca aagcttcttc ttcacaattc agatttcaat ttctcaaaat cttaaaaact   1260
ttctctcaat tctctctacc gtgatcaagg taaatttctg tgttccttat tctctcaaaa    1320
tcttcgattt tgttttcgtt cgatcccaat ttcgtatatg ttctttggtt tagattctgt   1380
taatcttaga tcgaagacga ttttctgggt ttgatcgtta gatatcatct taattctcga   1440
ttagggtttc ataaatatca tccgatttgt tcaaataatt tgagttttgt cgaataatta   1500
ctcttcgatt tgtgatttct atctagatct ggtgttagtt tctagtttgt gcgatcgaat   1560
ttgtcgatta atctgagttt ttctgattaa cagagatctc catggagaac aatatccaga   1620
accagtgtgt cccatacaat tgcctcaaca atcctgaagt tgagatcctc aacgaagaga   1680
ggagcactgg acgccttccc cttgacatct ccctctccct cacaaggttc cttttgtctg   1740
agtttgttcc tggtgtgggt gtggcctttg gcctctttga cctcatctgg ggcttcatca   1800
ccccatctga ttggagcctc ttccttctcc agattgaaca attgattgag cagaggattg   1860
agacccttga aaggaacaga gccatcacca cacttcgtgg ccttgctgac agctatgaaa   1920
```

```
tctacattga agcactccgt gagtgggaag ccaatcccaa caatgctcaa ctccgtgaag    1980
atgtgaggat tcgctttgcc aacacagatg acgctttgat cacagccatc aacaatttca    2040
ccctcaccag ctttgagatc cctttgctct cagtctatgt tcaagctgca aacctccact    2100
tgagcttgct tagggatgct gtgtccttcg gacaaggttg gggacttgac atagccactg    2160
tcaacaatca ctacaacaga ctcatcaact tgattcatcg ctacaccaaa cattgcttgg    2220
acacctacaa tcaaggattg gagaacctca gaggcaccaa cactcgccaa tgggcaaggt    2280
tcaaccagtt tagaagggat ctcacactca ctgtgcttga catagttgct ctcttcccca    2340
actatgatgt tcgcacctac ccaattcaaa ccagctccca acttacaagg gaaatctaca    2400
cctcctcagt cattgaggac agcccagttt ctgccaacat acccaatggt ttcaaccgtg    2460
ctgagtttgg tgtcagacca ccccatctca tggacttcat gaactccttg tttgtgactg    2520
ccgagactgt taggtcccaa actgtgtggg gaggccacct tgttagctcc cgcaacaccg    2580
ctggcaaccg catcaacttc ccatcctatg ggttttcaa tcctggtgga gccatctgga    2640
ttgcagatga ggacccaagg cctttctaca gaaccttgtc agatcctgtc tttgtcagag    2700
gaggctttgg caatcacac tatgttcttg gtttgagggg agtggctttt cagcagactg    2760
gcaccaatca cacccgcaca ttcagaaaca gcggcaccat tgacagcctt gatgagatcc    2820
cacctcaaga caacagcgga gcaccctgga acgactactc ccatgtgctc aatcatgtca    2880
cctttgtgcg ctggcctggt gagatcagcg gttcagattc ttggagagca ccaatgttct    2940
catggaccca tcgctctgcc acacccacaa acaccattga tccagagaga atcacccaga    3000
ttcccttggt gaaggcacac acacttcagt ctggaaccac agttgtcaga gggcctgggt    3060
tcactggtgg agacattctc agacgcacct ctggagggcc atttgcttac accattgtca    3120
acatcaatgg gcaacttccc cagcgttacc gtgccagaat ccgctatgct ccaccacta    3180
acttgagaat ctatgtcaca gttgctggtg aaaggatctt tgctggtcag ttcaacaaga    3240
caatggacac tggtgatcca ttgacattcc agtcattctc ctatgccacc atcaacactg    3300
cattcacctt tccaatgagc cagtccagct tcacagtggg tgcagatacc ttcagctccg    3360
gcaatgaggt gtacattgac cgcttttgagt tgattccagt gactgccaca cttgaggctg    3420
agtctgactt ggagcgtgct cagaaggccg tgaatgctct cttcacctct tcaaatcaga    3480
ttgggctcaa gacagatgtg actgactacc atatagaccg tgtttccaat cttgttgagt    3540
gcctctctga tgagttctgc ttggatgaga agaaagagtt gtcagagaag gtcaagcacg    3600
ccaagaggct ctctgatgag aggaacttgc ttcaagatcc caacttcaga gggatcaacc    3660
gtcaattgga tcgtggatgg aggggatcaa ctgacataac cattcaagga ggtgacgatg    3720
tgttcaagga gaactatgtc acactcttgg ggacctttga tgagtgctac ccaacatacc    3780
tttaccagaa gatagacgaa agcaagctca aggcctacac aagataccag ttgagaggtt    3840
acattgagga ctctcaagac cttgaaatct acctcatcag atacaacgcc aaacatgaga    3900
cagtcaatgt gcctgggact ggttcactct ggccactttc agccccaagc cccattggca    3960
agtgtgccca tcactcacat cacttctcct tggacataga tgttggctgc actgacttga    4020
atgaggacct tggtgtgtgg gtgatcttca agatcaagac ccaagatggc catgcaaggt    4080
tgggcaatct tgagtttctt gaagagaaac cacttgttgg agaagccctt gccagagtga    4140
agagggctga gaagaaatgg agggacaaga gagagaagtt ggagtgggaa acaaacattg    4200
tgtacaaaga agccaaagaa tcagttgatg ctttgttttgt gaactcccaa tatgataggc    4260
tccaagctga caccaacata gcaatgattc atgctgcaga caaagggtt cacagcattc    4320
```

```
gtgaagcata ccttcctgaa ctctcagtga ttcctggggt caatgctgca atctttgaag    4380
agcttgaagg acgcatcttc actgccttct ccttgtatga tgcaaggaat gtcatcaaga    4440
atggtgactt caacaatggc cttcctgct ggaatgtgaa agggcacgtg gatgttgaag    4500
agcagaacaa tcaccgctct gtccttgttg tccctgagtg ggaagctgaa gtttcacaag    4560
aagttcgtgt ctgccctggt cgtggctaca ttcttcgtgt gactgcttac aaagaaggct    4620
atggagaagg ttgtgtcacc atccacgaga tagagaacaa tactgatgaa ttgaagttca    4680
gcaactgtgt tgaggaagag gtctacccaa acaatactgt cacttgcaat gactacactg    4740
caactcaaga agagtatgag ggcacttaca cttctcgcaa ccgtggctat gatggagcct    4800
atgagagcaa ctcatctgtg cctgctgact atgcttcagc ctatgaagag aaggcataca    4860
ctgatggaag gcgtgacaat ccttgtgaaa gcaacagagg ctatggggac tacacacccc    4920
tcccagctgg ctatgtgacc aaagagttgg agtactttcc tgaaactgac aaggtttgga    4980
ttgagatagg agaaactgaa ggcacattca tagttgactc tgtggagctt ttgctcatgg    5040
aagagtgagt agttagctta atcacctaga gctcggtcac cagcataatt tttattaatg    5100
tactaaatta ctgttttgtt aaatgcaatt ttgcttctc gggattttaa tatcaaaatc    5160
tatttagaaa tacacaatat tttgttgcag gcttgctgga gaatcgatct gctatcataa    5220
aaattacaaa aaaattttat ttgcctcaat tattttagga ttggtattaa ggacgcttaa    5280
attatttgtc gggtcactac gcatcattgt gattgagaag atcagcgata cgaaatattc    5340
gtagtactat cgataattta tttgaaaatt cataagaaaa gcaaacgtta catgaattga    5400
tgaaacaata caaagacaga taaagccacg cacatttagg atattggccg agattactga    5460
atattgagta agatcacgga atttctgaca ggagcatgtc ttcaattcag cccaaatggc    5520
agttgaaata ctcaaaccgc cccatatgca ggagcggatc attcattgtt tgtttggttg    5580
cctttgccaa catgggagtc caaggttgcg gccgcgcgcc gaaacaaact ttgtatacaa    5640
aagttgccgc ggtgactgac tgaactaaac ccagaaggta attatccaag atgtagcatc    5700
aagaatccaa tgtttacggg aaaaactatg gaagtattat gtaagctcag caagaagcag    5760
atcaatatgc ggcacatatg caacctatgt tcaaaaatga agaatgtaca gatacaagat    5820
cctatactgc cagaatacga agaagaatac gtagaaattg aaaaagaaga accaggcgaa    5880
gaaaagaatc ttgaagacgt aagcactgac gacaacaatg aaaagaagaa gataaggtcg    5940
gtgattgtga agagacata gaggacacat gtaaggtgga aaatgtaagg gcggaaagta    6000
accttatcac aaaggaatct tatcccccac tacttatcct tttatatttt tccgtgtcat    6060
ttttgccctt gagttttcct atataaggaa ccaagttcgg catttgtgaa acaagaaaa    6120 aatttggtgt aagctatttt ctttgaagta ctgaggatac aacttcagag aaatttgtaa    6180
gtttgtagat ccaacaatgg acaacaatcc caacatcaac gagtgcattc cttacaactg    6240
cctgagcaac cctgaggttg aggtgctggg tggagaacgg attgagactg ttacacacc    6300 tatcgacatc tcgttgtcac ttacccaatt cctttgtca gagttcgtgc ccggtgctgg    6360
attcgtgctt ggacttgtcg atatcatttg gggaatcttt ggtccctctc aatgggacgc    6420
ctttcttgta cagatagagc agttaattaa ccaaagaata gaagaattcg ctaggaacca    6480
agccatctca aggttagaag gcctcagcaa cctttaccag atttacgcag aatcttttcg    6540
agagtgggaa gcagacccga ccaatcctgc cttaagagag gagatgcgca ttcaattcaa    6600
tgacatgaac agcgcgctga cgaccgcaat tccgctcttc gccgttcaga attaccaagt    6660
```

```
tcctcttta  tccgtgtacg  tgcaggctgc  caacctgcac  ttgtcggtgc  tccgcgatgt   6720
ctccgtgttc  ggacaacggt  ggggctttga  tgccgcaact  atcaatagtc  gttataatga   6780
tctgactagg  cttattggca  actataccga  ttatgctgtt  cgctggtaca  acacgggtct   6840
cgaacgtgtc  tggggaccgg  attctagaga  ttgggtcagg  tacaaccagt  tcaggcgaga   6900
gttgacacta  actgtcctag  acattgtcgc  tctctttccc  aactacgact  ctaggcgcta   6960
cccaatccgt  actgtgtcac  aattgacccg  ggaaatctac  acaaacccag  tcctcgagaa   7020
cttcgacggt  agctttcgag  gctcggctca  gggcatagag  agaagcatca  ggtctccaca   7080
cctgatggac  atattgaaca  gtatcacgat  ctacaccgat  gcgcaccgcg  gttattacta   7140
ctggtcaggg  catcagatca  tggcatcacc  cgttgggttc  tctggaccag  aattcacttt   7200
cccactttac  gggactatgg  gcaatgcagc  tccacaacaa  cgtattgttg  ctcaactcgg   7260
tcagggcgtg  tatagaacct  tgtccagcac  tctatatagg  agacctttca  acatcggcat   7320
caacaatcaa  caattgtctg  tgcttgacgg  gacagaattt  gcctatggaa  cctcctcaaa   7380
tctgccatcc  gctgtctaca  gaaagagcgg  aacagttgat  agcttggatg  agatccctcc   7440
acagaacaac  aacgttccac  ctaggcaagg  gtttagccat  cgccttagcc  atgtgtccat   7500
gttccgttca  ggctttagta  atagcagcgt  tagtatcatc  agagctccga  tgttctcttg   7560
gatacatcgt  agtgctgagt  ttaacaacat  aattgcatcc  gatagcatta  ctcagatccc   7620
agctgtcaag  gggaactttc  tctttaatgg  ttctgtcatt  tcaggaccag  gattcactgg   7680
aggcgacttg  gttaggctga  attcttccgg  caacaacatc  cagaatagag  ggtatattga   7740
agtgcccatt  cacttcccat  cgacatctac  cagatatcgt  gttcgtgtaa  ggtatgcctc   7800
tgttacccct  attcacctca  acgtcaattg  gggtaattcc  tccatctttt  ccaatacagt   7860
accagcgaca  gctacatcct  tggataatct  ccaatctagc  gatttcggtt  acttcgaaag   7920
tgccaatgcc  ttcacctctt  ccctaggtaa  catagtaggt  gttagaaatt  tctccggaac   7980
cgccggagtg  ataatcgacc  gcttcgaatt  cattcccgtt  actgcaacgc  tcgaggcaga   8040
gtctgacttg  gaaagagcac  agaaggcggt  gaatgctctg  ttcacttcgt  ccaatcagat   8100
tgggctcaag  acagatgtga  ctgactatca  catcgatcgc  gtttccaacc  ttgttgagtg   8160
cctctctgat  gagttctgtt  tggatgagaa  gaaggagttg  tccgagaagg  tcaaacatgc   8220
taagcgactt  agtgatgagc  ggaacttgct  tcaagatccc  aactttcgcg  ggatcaacag   8280
gcaactagat  cgtggatgga  ggggaagtac  ggacatcacc  attcaaggag  gtgatgatgt   8340
gttcaaggag  aactatgtta  cgctcttggg  tacctttgat  gagtgctatc  caacatacct   8400
gtaccagaag  atagatgaat  cgaaactcaa  agcctacaca  agataccagt  tgagaggtta   8460
catcgaggac  agtcaagacc  ttgagatcta  cctcatcaga  tacaacgcca  acatgagac   8520 agtcaatgtg  cctgggacgg  gttcactctg  gccactttca  gccccaagtc  catcggcaa   8580 gtgtgcccat  cactcacacc  acttctcctt  ggacatagac  gttggctgta  ccgacctgaa   8640
cgaagacctc  ggtgtgtggg  tgatcttcaa  gatcaagact  caagatggcc  atgccaggct   8700
aggcaatctg  gagtttctag  aagagaaacc  acttgttgga  gaagccctcg  ctagagtgaa   8760
gagggctgaa  aagaagtgga  gggacaagag  agagaagttg  gaatgggaaa  caaacattgt   8820
gtacaaagaa  gccaaagaaa  gcgttgacgc  tctgtttgtg  aactctcagt  atgataggct   8880
ccaagctgat  accaacatag  ctatgattca  tgctgcagac  aaacgcgttc  atagcattcg   8940
ggaagcttac  cttcctgaac  ttagcgtgat  tccgggtgtc  aatgctgcta  tctttgaaga   9000
gttagaaggg  cgcatcttca  ctgcattctc  cttgtatgat  gcgaggaatg  tcatcaagaa   9060
```

```
tggtgacttc aacaatggcc tatcctgctg gaatgtgaaa gggcacgtag atgtagaaga   9120
acagaacaat caccgctctg tccttgttgt tcctgagtgg gaagcagaag tttcacaaga   9180
agttcgtgtc tgtcctggtc gtggctacat tcttcgtgtt accgcgtaca aagaaggata   9240
cggagaaggt tgcgtcacca tacacgagat tgagaacaac accgacgagc tgaagttcag   9300
caactgcgtc gaggaggaag tctacccaaa caacaccgta acttgcaatg actacactgc   9360
gactcaagag gagtatgagg gtacttacac ttctcgcaat cgaggatacg atggagccta   9420
tgagagcaac tcttctgtac ccgctgacta tgcatcagcc tatgaggaga aggcttacac   9480
cgatggacgt agggacaatc cttgcgaatc taacagaggc tatggggact acacaccgtt   9540
accagccggc tatgtcacca aagagttaga gtactttcca gaaaccgaca aggtttggat   9600
tgagattgga gaaacggaag gaacattcat tgttgatagc gtggagttac ttctgatgga   9660
ggaatgagta gttagcttaa tcacctagag ctcggttacc tatcaaaatc tatttagaaa   9720
tacacaatat tttgttgcag gcttgctgga gaatcgatct gctatcataa aaattacaaa   9780
aaaattttat ttgcctcaat tatttagga ttggtattaa ggacgcttaa attatttgtc   9840
gggtcactac gcatcattgt gattgagaag atcagcgata cgaaatattc gtagtactat   9900
cgataattta tttgaaaatt cataagaaaa gcaaacgtta catgaattga tgaaacaata   9960
caaagacaga taaagccacg cacatttagg atattggccg agattactga atattgagta  10020
agatcacgga atttctgaca ggagcatgtc ttcaattcag cccaaatggc agttgaaata  10080
ctcaaaccgc cccatatgca ggagcggatc attcattgtt tgtttggttg cctttgccaa  10140
catgggagtc caaggttgcg gccgcgcgcc gacccagctt tcttgtacaa agtggttgcg  10200
gccgcttaat taaatttaaa tgcccggcg tttaaacgcg gccgcttaat taaggccggc   10260
ctgcagcaaa cccagaaggt aattatccaa gatgtagcat caagaatcca atgtttacgg  10320
gaaaaactat ggaagtatta tgtaagctca gcaagaagca gatcaatatg cggcacatat  10380
gcaacctatg ttcaaaaatg aagaatgtac agatacaaga tcctatactg ccagaatacg  10440
aagaagaata cgtagaaatt gaaaagaag aaccaggcga agaaaagaat cttgaagacg  10500
taagcactga cgacaacaat gaaaagaaga agataaggtc ggtgattgtg aaagagacat  10560
agaggacaca tgtaaggtgg aaaatgtaag ggcggaaagt aaccttatca caaaggaatc  10620
ttatcccca ctactatcc ttttatattt ttccgtgtca tttttgccct tgagttttcc    10680
tatataagga accaagttcg gcatttgtga aaacaagaaa aaatttggtg taagctattt  10740
tctttgaagt actgaggata caacttcaga gaaatttgta agtttgtaga tctccatgtc  10800
tccggagagg agaccagttg agattaggcc agctacagca gctgatatgg ccgcggtttg  10860
tgatatcgtt aaccattaca ttgagacgtc tacagtgaac tttaggacag agccacaaac  10920
accacaagag tggattgatg atctagagag gttgcaagat agataccctt ggttggttgc  10980
tgaggttgag ggtgttgtgg ctggtattgc ttacgctggg ccctggaagg ctaggaacgc  11040
ttacgattgg acagttgaga gtactgttta cgtgtcacat aggcatcaaa ggttgggcct  11100
aggatccaca ttgtacacac atttgcttaa gtctatggag gcgcaaggtt ttaagtctgt  11160
ggttgctgtt ataggccttc caaacgatcc atctgttagg ttgcatgagg ctttgggata  11220
cacagcccgg ggtacattgc gcgcagctgg atacaagcat ggtggatggc atgatgttgg  11280
ttttgcaa agggattttg agttgccagc tcctccaagg ccagttaggc cagttaccca    11340
gatctgaggt accctgagct tgagcttatg agcttatgag cttagagctc ggatccacta  11400
```

```
gtaacggccg ccagtgtgct ggaattcgcc cttgactaga taggcgccca gatcggcggc    11460
aatagcttct tagcgccatc ccgggttgat cctatctgtg ttgaaatagt tgcggtgggc    11520
aaggctctct ttcagaaaga caggcggcca aaggaaccca aggtgaggtg ggctatggct    11580
ctcagttcct tgtggaagcg cttggtctaa ggtgcagagg tgttagcggg atgaagcaaa    11640
agtgtccgat tgtaacaaga tatgttgatc ctacgtaagg atattaaagt atgtattcat    11700
cactaatata atcagtgtat tccaatatgt actacgattt ccaatgtctt tattgtcgcc    11760
gtatgtaatc ggcgtcacaa aataatcccc ggtgactttc ttttaatcca ggatgaaata    11820
atatgttatt ataattttg cgatttggtc cgttatagga attgaagtgt gcttgcggtc     11880
gccaccactc ccatttcata attttacatg tatttgaaaa ataaaaattt atggtattca    11940
atttaaacac gtatacttgt aaagaatgat atcttgaaag aaatatagtt taaatattta    12000
ttgataaaat aacaagtcag gtattatagt ccaagcaaaa acataaattt attgatgcaa    12060
gtttaaattc agaaatattt caataactga ttatatcagc tggtacattg ccgtagatga    12120
aagactgagt gcgatattat ggtgtaatac atagcggccg ggtttctagt caccggttag    12180
gatccgttta aactcgaggc tagcgcatgc acatagacac acacatcatc tcattgatgc    12240
ttggtaataa ttgtcattag attgttttta tgcatagatg cactcgaaat cagccaattt    12300
tagacaagta tcaaacggat gtgacttcag tacattaaaa acgtccgcaa tgtgttatta    12360
agttgtctaa gcgtcaattt g                                              12381

<210> SEQ ID NO 4
<211> LENGTH: 30
<212> TYPE: DNA
<213> ORGANISM: Artificial Sequence
<220> FEATURE:
<223> OTHER INFORMATION: 81419_FW3 Primer

<400> SEQUENCE: 4
tttctcctat ccgtcaaata aatctgctcc                                         30

<210> SEQ ID NO 5
<211> LENGTH: 27
<212> TYPE: DNA
<213> ORGANISM: Artificial Sequence
<220> FEATURE:
<223> OTHER INFORMATION: 81419_RV1 primer

<400> SEQUENCE: 5
gggtgatttg gtgccaaaag ttatgtt                                            27

<210> SEQ ID NO 6
<211> LENGTH: 24
<212> TYPE: DNA
<213> ORGANISM: Artificial Sequence
<220> FEATURE:
<223> OTHER INFORMATION: 81419_RV2 primer

<400> SEQUENCE: 6
tggagggtca tatcgcaaaa gact                                               24

<210> SEQ ID NO 7
<211> LENGTH: 24
<212> TYPE: DNA
<213> ORGANISM: Artificial Sequence
<220> FEATURE:
<223> OTHER INFORMATION: 81419_RV3 primer

<400> SEQUENCE: 7
```

-continued gttctgcgtc gtggagggtc atat    24

<210> SEQ ID NO 8
<211> LENGTH: 29
<212> TYPE: DNA
<213> ORGANISM: Artificial Sequence
<220> FEATURE:
<223> OTHER INFORMATION: 5'IREnd-01 primer

<400> SEQUENCE: 8
cgagctttct aatttcaaac tattcgggc    29

<210> SEQ ID NO 9
<211> LENGTH: 30
<212> TYPE: DNA
<213> ORGANISM: Artificial Sequence
<220> FEATURE:
<223> OTHER INFORMATION: 5'IREnd-02 primer

<400> SEQUENCE: 9
tcctagatca tcagttcata caaacctcca    30

<210> SEQ ID NO 10
<211> LENGTH: 29
<212> TYPE: DNA
<213> ORGANISM: Artificial Sequence
<220> FEATURE:
<223> OTHER INFORMATION: AtUbi10RV1 primer

<400> SEQUENCE: 10
cggtcctaga tcatcagttc atacaaacc    29

<210> SEQ ID NO 11
<211> LENGTH: 28
<212> TYPE: DNA
<213> ORGANISM: Artificial Sequence
<220> FEATURE:
<223> OTHER INFORMATION: AtUbi10RV2 primer

<400> SEQUENCE: 11
cactcgtgtt cagtccaatg accaataa    28

<210> SEQ ID NO 12
<211> LENGTH: 20
<212> TYPE: DNA
<213> ORGANISM: Artificial Sequence
<220> FEATURE:
<223> OTHER INFORMATION: 3'PATEnd05 primer

<400> SEQUENCE: 12
gctcctccaa ggccagttag    20

<210> SEQ ID NO 13
<211> LENGTH: 20
<212> TYPE: DNA
<213> ORGANISM: Artificial Sequence
<220> FEATURE:
<223> OTHER INFORMATION: 3'PATEnd06 primer

<400> SEQUENCE: 13
ccagttaggc cagttaccca    20

<210> SEQ ID NO 14
<211> LENGTH: 15294
<212> TYPE: DNA

<213> ORGANISM: Artificial Sequence
<220> FEATURE:
<223> OTHER INFORMATION: Expected sequence of soybean event 9582.814.19.1

<400> SEQUENCE: 14

```
ttaacaatga ccaagattta tgctatatag aagacttgga gggcttaagg ctatgatata      60
ttatggatga tatggttctg atttgtgtag tttcgaagga tcaaatcaac catttgttgg     120
tacaatggga agaaaaaatg ttttcatcat tccactctat tgaaaaagat ccaacaattg     180
taacaccccg acgaatcaca ccggaaagag aagaatccaa agattgtgta ggtatgagac     240
tgtatagttg atgaaaactt aaaaaaatta attggtacta cttataccaa caagatgcat     300
atatttttcg atagcctatc acataagaac ttcatagtta agggtgctta acttggagta     360
gttatgaaat gagtgacctt ttaaaataat tattgtctta ggttattgta tgaaaataaa     420
aaataataat aaatatacat aaaaaataat aatttataa aattaacctt atattatcat      480
taatttattt ttagattttg ttattcatta ttaatatatg aggtataaat gaaaaatata     540
attaatgtca cattaaaaaa ttaaaatgat aattattttg aaacaaatta tttattttta     600
tacgacaatt ataatagaaa tttgagagta aaaaaaaatt gaaaattcat aaaatatatg     660
aatatattca tttctcctat ccgtcaaata aatctgctcc ataatttatc taagcattgg     720
tcttgtagtt cagagtaata aaattttagc aattattagt tagtacagat acatttaaag     780
aaataatata ttttagcaac tagaagttta taaaaagttt taaattataa agacttatat     840
ataaatttag taaaactaga tggatgtccc aagtaatttt tatataacta ttctcgtaca     900
acattaatga aaatcttgtt tctattattt atatgtatat tattatttta ttttggaaca     960
atatgggatt aaaaactctt ataaattaaa tcttagaata agttttccta acatgttttt    1020
tttatggatg ttttcctaac atgtttggtt atcttagttt tgctttaatt ttgtcggatt    1080
attttttggac tttattaggt aattttgata aaacttttag ttgatgttag tagtttactc    1140
ttacataatg atttgatatt gaatgtgtat aattggaagg caataaatga agatcaagcg    1200
tacaagagtt cgccaatcaa gaggatttga agagagtaaa atattatgcg aagtcccatg    1260
tgaagaaaat ccaaccattg gaataaaaaa taaagttttt tctttggaat tgctaatgct    1320
acagcactta ttggtacttg tcctaaaaat gaaactctag ctatatttag cacttgatat    1380
tcatgaatca aacttctcta tgaaataacc gcggtgcgca tcggtgcctg ttgatcccgc    1440
gcaagtgggg atcttgaagc aagttccgct catcactaag tcgcttagca tgtttgacct    1500
tctcggacaa ctccttcttc tctttaattg atcaacagtc agcatcatca caccaaaagt    1560
taggcccgaa tagtttgaaa ttagaaagct cgcaattgag gtctacaggc caaattcgct    1620
cttagccgta caatattact caccggatcc taaccggtgt gatcatgggc cgcgattaaa    1680
aatctcaatt atatttggtc taatttagtt tggtattgag taaaacaaat tcggcgccat    1740
gcccgggcaa gcggccgcac aagtttgtac aaaaaagcag gctccgcggt gactgactga    1800
aaagcttgtc gacctgcagg tcaacggatc aggatattct tgtttaagat gttgaactct    1860
atggaggttt gtatgaactg atgatctagg accggataag ttcccttctt catagcgaac    1920
ttattcaaag aatgttttgt gtatcattct tgttacattt ttattaatga aaaaatatta    1980
ttggtcattg gactgaacac gagtgttaaa tatggaccag gccccaaata agatccattg    2040
atatatgaat taaataacaa gaataaatcg agtcaccaaa ccacttgcct tttttaacga    2100
gacttgttca ccaacttgat acaaaagtca ttatcctatg caaatcaata atcatacaaa    2160
```

```
aatatccaat aacactaaaa aattaaaaga aatggataat ttcacaatat gttatacgat    2220
aaagaagtta cttttccaag aaattcactg attttataag cccacttgca ttagataaat    2280
ggcaaaaaaa aacaaaaagg aaaagaaata aagcacgaag aattctagaa aatacgaaat    2340
acgcttcaat gcagtgggac ccacggttca attattgcca attttcagct ccaccgtata    2400
tttaaaaaat aaaacgataa tgctaaaaaa atataaatcg taacgatcgt taaatctcaa    2460
cggctggatc ttatgacgac cgttagaaat tgtggttgtc gacgagtcag taataaacgg    2520
cgtcaaagtg gttgcagccg gcacacacga gtcgtgttta tcaactcaaa gcacaaatac    2580
ttttcctcaa cctaaaaata aggcaattag ccaaaaacaa ctttgcgtgt aaacaacgct    2640
caatacacgt gtcattttat tattagctat tgcttcaccg ccttagcttt ctcgtgacct    2700
agtcgtcctc gtcttttctt cttcttcttc tataaaacaa tacccaaagc ttcttcttca    2760
caattcagat ttcaatttct caaaatctta aaaactttct ctcaattctc tctaccgtga    2820
tcaaggtaaa tttctgtgtt ccttattctc tcaaaatctt cgattttgtt ttcgttcgat    2880
cccaatttcg tatatgttct ttggtttaga ttctgttaat cttagatcga agacgatttt    2940
ctgggtttga tcgttagata tcatcttaat tctcgattag ggtttcataa atatcatccg    3000
atttgttcaa ataatttgag ttttgtcgaa taattactct tcgatttgtg atttctatct    3060
agatctggtg ttagttttcta gtttgtgcga tcgaatttgt cgattaatct gagtttttct    3120
gattaacaga gatctccatg gagaacaata tccagaacca gtgtgtccca tacaattgcc    3180
tcaacaatcc tgaagttgag atcctcaacg aagagaggag cactggacgc cttcccttg     3240
acatctccct ctccctcaca aggttccttt tgtctgagtt tgttcctggt gtgggtgtgg    3300
cctttggcct ctttgacctc atctggggct tcatcacccc atctgattgg agcctcttcc    3360
ttctccagat tgaacaattg attgagcaga ggattgagac ccttgaaagg aacagagcca    3420
tcaccacact tcgtggcctt gctgacagct atgaaatcta cattgaagca ctccgtgagt    3480
gggaagccaa tcccaacaat gctcaactcc gtgaagatgt gaggattcgc tttgccaaca    3540
cagatgacgc tttgatcaca gccatcaaca atttcaccct caccagcttt gagatccctt    3600
tgctctcagt ctatgttcaa gctgcaaacc tccacttgag cttgcttagg gatgctgtgt    3660
ccttcggaca aggttgggga cttgacatag ccactgtcaa caatcactac aacagactca    3720
tcaacttgat tcatcgctac accaaacatt gcttggacac ctacaatcaa ggattggaga    3780
acctcagagg caccaacact cgccaatggg caaggttcaa ccagtttaga agggatctca    3840
cactcactgt gcttgacata gttgctctct tccccaacta tgatgttcgc acctaccca    3900
ttcaaaccag ctcccaactt acaagggaaa tctacacctc ctcagtcatt gaggacagcc    3960
cagtttctgc caacataccc aatggtttca accgtgctga gtttggtgtc agaccacccc    4020
atctcatgga cttcatgaac tccttgtttg tgactgccga gactgttagg tcccaaactg    4080
tgtggggagg ccaccttgtt agctcccgca acaccgctgg caaccgcatc aacttcccat    4140
cctatgggt tttcaatcct ggtggagcca tctggattgc agatgaggac ccaaggcctt    4200
tctacagaac cttgtcagat cctgtctttg tcagaggagg cttttggcaat ccacactatg    4260
ttcttggttt gaggggagtg gcttttcagc agactggcac caatcacacc cgcacattca    4320
gaaacagcgg caccattgac agccttgatg agatcccacc tcaagacaac agcggagcac    4380
cctggaacga ctactcccat gtgctcaatc atgtcacctt tgtgcgctgg cctggtgaga    4440
tcagcggttc agattcttgg agagcaccaa tgttctcatg gacccatcgc tctgccacac    4500
ccacaaacac cattgatcca gagagaatca cccagattcc cttggtgaag gcacacacac    4560
```

```
ttcagtctgg aaccacagtt gtcagagggc ctgggttcac tggtggagac attctcagac    4620
gcacctctgg agggccattt gcttacacca ttgtcaacat caatgggcaa cttccccagc    4680
gttaccgtgc cagaatccgc tatgcttcca ccactaactt gagaatctat gtcacagttg    4740
ctggtgaaag gatctttgct ggtcagttca acaagacaat ggacactggt gatccattga    4800
cattccagtc attctcctat gccaccatca acactgcatt cacctttcca atgagccagt    4860
ccagcttcac agtgggtgca gataccttca gctccggcaa tgaggtgtac attgaccgct    4920
ttgagttgat tccagtgact gccacacttg aggctgagtc tgacttggag cgtgctcaga    4980
aggccgtgaa tgctctcttc acctcttcaa atcagattgg gctcaagaca gatgtgactg    5040
actaccatat agaccgtgtt tccaatcttg ttgagtgcct ctctgatgag ttctgcttgg    5100
atgagaagaa agagttgtca gagaaggtca agcacgccaa gaggctctct gatgagagga    5160
acttgcttca agatcccaac ttcagaggga tcaaccgtca attggatcgt ggatggaggg    5220
gatcaactga cataaccatt caaggagtg acgatgtgtt caaggagaac tatgtcacac    5280
tcttggggac ctttgatgag tgctacccaa catacctta ccagaagata gacgaaagca    5340
agctcaaggc ctacacaaga taccagttga gaggttacat tgaggactct caagaccttg    5400
aaatctacct catcagatac aacgccaaac atgagacagt caatgtgcct gggactggtt    5460
cactctggcc actttcagcc ccaagcccca ttggcaagtg tgcccatcac tcacatcact    5520
tctccttgga catagatgtt ggctgcactg acttgaatga ggaccttggt gtgtgggtga    5580
tcttcaagat caagacccaa gatggccatg caaggttggg caatcttgag tttcttgaag    5640
agaaaccact tgttggagaa gcccttgcca gagtgaagag ggctgagaag aaatggaggg    5700
acaagagaga gaagttggag tgggaaacaa acattgtgta caagaagcc aaagaatcag    5760 ttgatgcttt gtttgtgaac tcccaatatg ataggctcca agctgacacc aacatagcaa    5820
tgattcatgc tgcagacaaa agggttcaca gcattcgtga agcataccttcctgaactct    5880 cagtgattcc tggggtcaat gctgcaatct ttgaagagct tgaaggacgc atcttcactg    5940
ccttctcctt gtatgatgca aggaatgtca tcaagaatgg tgacttcaac aatggccttt    6000
cctgctggaa tgtgaaaggg cacgtggatg ttgaagagca gaacaatcac cgctctgtcc    6060
ttgttgtccc tgagtgggaa gctgaagttt cacaagaagt tcgtgtctgc cctggtcgtg    6120
gctacattct tcgtgtgact gcttacaaag aaggctatgg agaaggttgt gtcaccatcc    6180
acgagataga aacaatact gatgaattga agttcagcaa ctgtgttgag gagaggtct    6240 acccaaacaa tactgtcact tgcaatgact acactgcaac tcaagaagag tatgagggca    6300
cttacacttc tcgcaaccgt ggctatgatg agcctatga gagcaactca tctgtgcctg    6360
ctgactatgc ttcagcctat gaagagaagg catacactga tggaaggcgt gacaatcctt    6420
gtgaaagcaa cagaggctat ggggactaca caccctccc agctggctat gtgaccaaag    6480
agttggagta cttcctgaa actgacaagg tttggattga gataggagaa actgaaggca    6540
cattcatagt tgactctgtg gagcttttgc tcatggaaga gtgagtagtt agcttaatca    6600
cctagagctc ggtcaccagc ataattttta ttaatgtact aaattactgt tttgttaaat    6660
gcaattttgc ttttctcggga ttttaatatc aaaatctatt tagaaataca caatattttg    6720
ttgcaggctt gctggagaat cgatctgcta tcataaaat tacaaaaaaa ttttatttgc    6780
ctcaattatt ttaggattgg tattaaggac gcttaaatta tttgtcgggt cactacgcat    6840
cattgtgatt gagaagatca gcgatacgaa atattcgtag tactatcgat aatttatttg    6900
```

```
aaaattcata agaaaagcaa acgttacatg aattgatgaa acaatacaaa gacagataaa      6960
gccacgcaca tttaggatat tggccgagat tactgaatat tgagtaagat cacggaattt      7020
ctgacaggag catgtcttca attcagccca aatggcagtt gaaatactca aaccgcccca      7080
tatgcaggag cggatcattc attgtttgtt tggttgcctt tgccaacatg ggagtccaag      7140
gttgcggccg cgcgccgaaa acaactttgt atacaaaagt tgccgcggtg actgactgaa      7200
ctaaacccag aagtaatta tccaagatgt agcatcaaga atccaatgtt tacgggaaaa       7260
actatggaag tattatgtaa gctcagcaag aagcagatca atatgcggca catatgcaac      7320
ctatgttcaa aaatgaagaa tgtacagata caagatccta tactgccaga atacgaagaa      7380
gaatacgtag aaattgaaaa agaagaacca ggcgaagaaa agaatcttga agacgtaagc      7440
actgacgaca acaatgaaaa gaagaagata aggtcggtga ttgtgaaaga gacatagagg      7500
acacatgtaa ggtggaaaat gtaagggcgg aaagtaacct tatcacaaag gaatcttatc      7560
ccccactact tatcctttta tattttccg tgtcatttt gcccttgagt tttcctatat         7620
aaggaaccaa gttcggcatt tgtgaaaaca agaaaaaatt tggtgtaagc tattttcttt      7680
gaagtactga ggatacaact tcagagaaat ttgtaagttt gtagatccaa caatggacaa     7740
caatcccaac atcaacgagt gcattcctta caactgcctg agcaaccctg aggttgaggt      7800
gctgggtgga gaacggattg agactggtta cacacctatc gacatctcgt tgtcacttac     7860
ccaattcctt ttgtcagagt tcgtgcccgg tgctggattc gtgcttggac ttgtcgatat      7920
catttgggga atctttggtc cctctcaatg ggacgccttt cttgtacaga tagagcagtt     7980
aattaaccaa agaatagaag aattcgctag gaaccaagcc atctcaaggt tagaaggcct    8040
cagcaacctt taccagattt acgcagaatc ttttcgagag tgggaagcag acccgaccaa     8100
tcctgcctta agagaggaga tgcgcattca attcaatgac atgaacagcg cgctgacgac     8160
cgcaattccg ctcttcgccg ttcagaatta ccaagttcct ctttatccg tgtacgtgca      8220 ggctgccaac ctgcacttgt cggtgctccg cgatgtctcc gtgttcggac aacggtgggg     8280
ctttgatgcc gcaactatca atagtcgtta taatgatctg actaggctta ttggcaacta     8340
taccgattat gctgttcgct ggtacaacac gggtctcgaa cgtgtctggg accggattc      8400 tagagattgg gtcaggtaca accagttcag gcagagttg acactaactg tcctagacat     8460
tgtcgctctc tttcccaact acgactctag gcgctaccca atccgtactg tgtcacaatt     8520 gaccccgggaa atctacacaa acccagtcct cgagaacttc gacggtagct ttcgaggctc    8580
ggctcagggc atagagagaa gcatcaggtc tccacacctg atggacatat tgaacagtat     8640
cacgatctac accgatgcgc accgcggtta ttactactgg tcagggcatc agatcatggc    8700
atcacccgtt gggttctctg gaccagaatt cactttccca cttttacggga ctatgggcaa  8760 tgcagctcca caacaacgta ttgttgctca actcggtcag ggcgtgtata gaaccttgtc     8820
cagcactcta tataggagac cttttcaacat cggcatcaac aatcaacaat tgtctgtgct    8880
tgacgggaca gaatttgcct atggaacctc ctcaaatctg ccatccgctg tctacagaaa    8940
gagcggaaca gttgatagct tggatgagat ccctccacag aacaacaacg ttccacctag    9000
gcaagggttt agccatcgcc ttagccatgt gtccatgttc cgttcaggct ttagtaatag    9060
cagcgttagt atcatcagag ctccgatgtt ctcttggata catcgtagtg ctgagtttaa   9120
caacataatt gcatccgata gcattactca gatcccagct gtcaagggga actttctctt   9180
taatggttct gtcatttcag gaccaggatt cactggaggc gacttggtta ggctgaattc   9240
ttccggcaac aacatccaga atagagggta tattgaagtg cccattcact tcccatcgac  9300
```

```
atctaccaga tatcgtgttc gtgtaaggta tgcctctgtt acccctattc acctcaacgt   9360
caattggggt aattcctcca tcttttccaa tacagtacca gcgacagcta catccttgga   9420
taatctccaa tctagcgatt tcggttactt cgaaagtgcc aatgccttca cctcttccct   9480
aggtaacata gtaggtgtta gaaatttctc cggaaccgcc ggagtgataa tcgaccgctt   9540
cgaattcatt cccgttactg caacgctcga ggcagagtct gacttggaaa gagcacagaa   9600
ggcggtgaat gctctgttca cttcgtccaa tcagattggg ctcaagacag atgtgactga   9660
ctatcacatc gatcgcgttt ccaaccttgt tgagtgcctc tctgatgagt tctgtttgga   9720
tgagaagaag gagttgtccg agaaggtcaa acatgctaag cgacttagtg atgagcggaa   9780
cttgcttcaa gatcccaact ttcgcgggat caacaggcaa ctagatcgtg gatggagggg   9840
aagtacggac atcaccattc aaggaggtga tgatgtgttc aaggagaact atgttacgct   9900
cttgggtacc tttgatgagt gctatccaac atacctgtac cagaagatag atgaatcgaa   9960
actcaaagcc tacacaagat accagttgag aggttacatc gaggacagtc aagaccttga  10020
gatctacctc atcagataca acgccaaaca tgagacagtc aatgtgcctg ggacgggttc  10080
actctggcca ctttcagccc caagtcccat cggcaagtgt gcccatcact cacaccactt  10140
ctccttggac atagacgttg gctgtaccga cctgaacgaa gacctcggtg tgtgggtgat  10200
cttcaagatc aagactcaag atggccatgc caggctaggc aatctggagt ttctagaaga  10260
gaaaccactt gttggagaag ccctcgctag agtgaagagg gctgagaaga gtggaggga  10320 caagagagag aagttggaat gggaaacaaa cattgtgtac aaagaagcca agaaagcgt  10380 tgacgctctg tttgtgaact ctcagtatga taggctccaa gctgatacca acatagctat  10440
gattcatgct gcagacaaac gcgttcatag cattcgggaa gcttaccttc ctgaacttag  10500
cgtgattccg ggtgtcaatg ctgctatctt tgaagagtta aagggcgca tcttcactgc  10560 attctccttg tatgatgcga ggaatgtcat caagaatggt gacttcaaca atggcctatc  10620
ctgctggaat gtgaaagggc acgtagatgt agaagaacag aacaatcacc gctctgtcct  10680
tgttgttcct gagtgggaag cagaagtttc acaagaagtt cgtgtctgtc ctggtcgtgg  10740
ctacattctt cgtgttaccg cgtacaaaga aggatacgga gaaggttgcg tcaccataca  10800
cgagattgag aacaacaccg acgagctgaa gttcagcaac tgcgtcgagg aggaagtcta  10860
cccaaacaac accgtaactt gcaatgacta cactgcgact caagaggagt atgagggtac  10920
ttacacttct cgcaatcgag gatacgatgg agcctatgag agcaactctt ctgtacccgc  10980
tgactatgca tcagcctatg aggagaaggc ttacaccgat ggacgtaggg acaatccttg  11040
cgaatctaac agaggctatg ggactacac accgttacca gccggctatg tcaccaaaga  11100
gttagagtac tttccagaaa ccgacaaggt ttggattgag attggagaaa cggaaggaac  11160
attcattgtt gatagcgtgg agttacttct gatggaggaa tgagtagtta gcttaatcac  11220
ctagagctcg gttacctatc aaaatctatt tagaaataca caatattttg ttgcaggctt  11280
gctggagaat cgatctgcta tcataaaaat tacaaaaaaa ttttatttgc ctcaattatt  11340
ttaggattgg tattaaggac gcttaaatta tttgtcgggt cactacgcat cattgtgatt  11400
gagaagatca gcgatacgaa atattcgtag tactatcgat aatttatttg aaaattcata  11460
agaaaagcaa acgttacatg aattgatgaa acaatacaaa gacagataaa gccacgcaca  11520
tttaggatat tggccgagat tactgaatat tgagtaagat cacggaattt ctgacaggag  11580
catgtcttca attcagccca aatggcagtt gaaatactca aaccgcccca tatgcaggag  11640
```

```
cggatcattc attgtttgtt tggttgcctt tgccaacatg ggagtccaag gttgcggccg    11700
cgcgccgacc cagcttttctt gtacaaagtg gttgcggccg cttaattaaa tttaaatgcc   11760
cgggcgttta acgcggccgc cttaattaag gccggcctgc agcaaaccca gaaggtaatt    11820
atccaagatg tagcatcaag aatccaatgt ttacgggaaa aactatggaa gtattatgta    11880
agctcagcaa gaagcagatc aatatgcggc acatatgcaa cctatgttca aaaatgaaga    11940
atgtacagat acaagatcct atactgccag aatacgaaga agaatacgta gaaattgaaa    12000
aagaagaacc aggcgaagaa aagaatcttg aagacgtaag cactgacgac aacaatgaaa    12060
agaagaagat aaggtcggtg attgtgaaag agacatagag gacacatgta aggtggaaaa    12120
tgtaagggcg gaaagtaacc ttatcacaaa ggaatcttat cccccactac ttatcctttt    12180
atattttttcc gtgtcatttt tgcccttgag ttttcctata taggaaccaa gttcggcat    12240
ttgtgaaaac aagaaaaaat ttggtgtaag ctattttctt tgaagtactg aggatacaac    12300
ttcagagaaa tttgtaagtt tgtagatctc catgtctccg gagaggagac cagttgagat    12360
taggccagct acagcagctg atatggccgc ggtttgtgat atcgttaacc attacattga    12420
gacgtctaca gtgaacttta ggacagagcc acaaacacca caagagtgga ttgatgatct    12480
agagaggttg caagatagat acccttggtt ggttgctgag gttgagggtg ttgtggctgg    12540
tattgcttac gctgggccct ggaaggctag gaacgcttac gattggacag ttgagagtac    12600
tgtttacgtg tcatatagc atcaaaggtt gggcctagga tccacattgt acacacattt    12660
gcttaagtct atggaggcgc aaggttttaa gtctgtggtt gctgttatag gccttccaaa    12720
cgatccatct gttaggttgc atgaggcttt gggatacaca gcccggggta cattgcgcgc    12780
agctggatac aagcatggtg gatggcatga tgttggtttt tggcaaaggg attttgagtt    12840
gccagctcct ccaaggccag ttaggccagt tacccagatc tgaggtaccc tgagcttgag    12900
cttatgagct tatgagctta gagctcggat ccactagtaa cggccgccag tgtgctggaa    12960
ttcgcccttg actagatagg cgcccagatc ggcggcaata gcttcttagc gccatcccgg    13020
gttgatccta tctgtgttga aatagttgcg gtgggcaagg ctctctttca gaaagacagg    13080
cggccaaagg aacccaaggt gaggtgggct atggctctca gttccttgtg gaagcgcttg    13140
gtctaaggtg cagaggtgtt agcgggatga agcaaaagtg tccgattgta acaagatatg    13200
ttgatcctac gtaaggatat taagtatgt attcatcact aatataatca gtgtattcca    13260
atatgtacta cgatttccaa tgtctttatt gtcgccgtat gtaatcggcg tcacaaaata    13320
atccccggtg actttctttt aatccaggat gaaataatat gttattataa ttttgcgat    13380
ttggtccgtt ataggaattg aagtgtgctt gcggtcgcca ccactcccat ttcataattt    13440
tacatgtatt tgaaaaataa aaatttatgg tattcaattt aaacacgtat acttgtaaag    13500
aatgatatct tgaaagaaat atagtttaaa tatttattga taaaataaca agtcaggtat    13560
tatagtccaa gcaaaaacat aaattttatg atgcaagttt aaattcagaa atatttcaat    13620
aactgattat atcagctggt acattgccgt agatgaaaga ctgagtgcga tattatggtg    13680
taatacatag cggccgggtt tctagtcacc ggttaggatc cgtttaaact cgaggctagc    13740
gcatgcacat agacacacac atcatctcat tgatgcttgg taataattgt cattagattg    13800
ttttttatgca tagatgcact cgaaatcagc caatttttaga caagtatcaa acggatgtga    13860
cttcagtaca ttaaaaacgt ccgcaatatg atattcatta atttatatt atctaaaaga    13920
gttaaaagag aaaaaagaaa tatgacaatt tttttcttttc acatcttcta acctaaaagt    13980
atgactctat ggaggctaag tttagaaaaa gatacggatc tagggtgtgg aaacatcaat    14040
```

```
ggtcaactcc ttttatattt caatcaattg ggttttgctt tatctttaca ttttctcctt    14100
ttattttcca cgtctattca aatctacttg ttagcgggtg attactcttt tttcttttat    14160
agatgccaat tatttctctc ctatgtatta aattagagta tattgtcttg aaagtgactt    14220
agtattttag tttatagtct cttaaagaac gacacctttt attcttaact ctctttatca    14280
agttttaatt taaaattatt ttaaattaag tatgcataca tatcttaata ttttcttaa     14340 ttattttttaa attccctaaa tttaatgttt tcatacaatg taagagatat acatattaat   14400
tatatttaaa gataaaactt actttcctgc aataaaataa agaaaaggac agtcatacaa    14460
ttatataatt aatccagaat atttatagct tttaaacatt tattttctat caattaagta    14520
ataactttaa ataaaattaa gagtactttt ttatactcca aagaatttat ttattttcaa    14580
caaaatcgtc tgactgtttc aattgatcat tatcagccta gcataaccta aatttcattt    14640
tcaaacataa cttttggcac caaatcaccc ggcattgcaa aaaagtcttt tgcgatatga    14700
ccctccacga cgcagaacca ctgttattca ttaccatcac ttttaatcct aatttcccat    14760
acacttaccc tttccatgac atcttcaaag cctttatttt gcttttcttg tttaagctgt    14820
tttaacctaa tttcatgcat ataaacaaag agtaaagcaa aggcaaatat ttgtacgtat    14880 agttttttaga cagaaaagga aagtaaatta tagagataat gaagtttgct cttttaaatt   14940
cgtcgtgatg ttatccatca tatctaaatg cttattcctg tttttgtctt ttttctcttt    15000
taccggagtt tattttatat aattaattaa agttagtaga tctatattct ttttcataga   15060
taatccatct tctttggagg cacatcgatc attaatcata gagttttgag aagcattatc    15120
actaaagctt caattaatta tatccaataa acggtattgg tgtatgatgt tatgatagca    15180
aatagataat ctaatctata cgagccacaa aaggggcatg aactctatct cgaagaaatt    15240
ggagatgaag ggattgagat tggcaccttg tgctattatt gcccactaat catt           15294
```

<210> SEQ ID NO 15
<211> LENGTH: 10212
<212> TYPE: DNA
<213> ORGANISM: Artificial Sequence
<220> FEATURE:
<223> OTHER INFORMATION: Sequence of soybean event pDAB4468.04.16.1.
    Including the 5' genomic flanking sequence, pDAB4468 T-strand
    insert, and 3' genomic flanking sequence.

<400> SEQUENCE: 15

```
ctgtcgttgg attcacagaa cattgacgcc agttttcact tcgttatctt tgaattcatt      60
aaaatcgaat ctctcaccta tacccccca ttttctaat ccatcataat caaaattcat       120
aaatgaatca gttaccatta ccataatacc ttttgaaaa tgagtttgaa taatcagtat      180
ctttagaaaa ctaattaaga aattaaataa aaaatattta tcatgaagat gagtgtaaga    240
aaaattatga aaagtataac tttatacatt tctataaaat tatttttct tttaatttct     300 taattaatat cctaagtaaa tgagttaata tttatctttc aaaaattctt atagtcgcca    360
attaattttc ccatgcaatg acaacttgtc cgtattctac gtggtaggtt aggctacctg    420
ccgagacaaa ttgccttgag acaaattcaa tagagaaccc ttccaaggga ccattataaa    480
tagagaactt tcattaaccg ataagccaca cccttttcaat caaacacaaa cacttgaagt   540
actaagttag tgtgtttgag caaattaact atggcttcgt tttgttctag attgacaatt    600
tgtttggctc tgtttgtcct catatggggg agtgccaatg cacaactttc tacaaacttt    660
tactaccatt catgtccaaa cctcttctcc tctgtgaaat ccacagtgca atctgccata    720
```

| | |
|---|---|
| tctaaggaga cccgcatggg tgcttctctc cttcgcttgt tcttccacga ttgctttgtc | 780 |
| aatgtaattt atttgcacct tctcccactt acatacaaat atgctaagct tacatatagc | 840 |
| tcctctttct accacttgca tgcatcatct aattttgttt gaaacaacac ttgttccttt | 900 |
| tattatacac atcatctttg ataaaatttt gtcgtgtgca acttttttt agtgtgttaa | 960 |
| tcagttctat gatgatacta ttagttaaga aattttaatg cacttaataa accattttaa | 1020 |
| gtactttaac cgttcaatga tattatatat ttaaagataa taaatatttc tgcttttgtt | 1080 |
| tctatattag tgtagttaag aaccttctta cttcttagct agctaaatat taatgagtaa | 1140 |
| acattaacaa atgcagggat gtgatggttc aattctattg gatgacacat caagcttcac | 1200 |
| cggagagaag aacgcaaacc ccaacaggaa ctctgctcgt ggattcgagg ttattgacaa | 1260 |
| cattaaatca gccgtggaga aagtgtgtcc aggagttgtt tcctgcgcag atatccttgc | 1320 |
| catcgctgcc agagactctg ttcagattgt aagtggtcaa acaaccaaca aaaacacatt | 1380 |
| aaactaaatc attaaattgt acatatcaaa attaattacc aatttagtac cacacatgca | 1440 |
| attaaagaga acattttgtt gattttgatc aatatagctt ggaggcccta catggaatgt | 1500 |
| taaacttgga agaagagacg ctagaactgc tagccaatct gctgctaaca atggcatccc | 1560 |
| tgcacccact tcaaaccttn accaactcat ctcaagattt agcgctcttg gactttccac | 1620 |
| caaggacttg gtcgccttgt ccggtacaaa acatatatca cataattttc caattaatta | 1680 |
| catttcaatc atatagtaaa atttctcaat taattaggaa catgagaaac ttatagtcac | 1740 |
| acgttctttt gttgaggaat attgcatggt ttaattttgc tttcattagg tggtcacaca | 1800 |
| attggacaag caaggtgcac aaacttcaga gcccgcatct acaacgagac caacatagaa | 1860 |
| accgcatttg caaggactag gcagcaaagc tgccctagaa catcagggtc aggggacaac | 1920 |
| aatctggcac cacttgatct tcaaactcca accagctttg acaactacta cttcaagaac | 1980 |
| ctcgttcaga agaagggtct cctccactct gatcagcaac tgttcaacgg tgggtccacc | 2040 |
| gactccattg tgcgtggcta cagcaccaac ccgggcacct tctcctctga tttcgccgcc | 2100 |
| gccatgatca agatgggaga cattagtcct ctcactggct ccaatggaga aatcaggaag | 2160 |
| aattgtagaa ggattaacta atttgattca gtcttgaata ttaagggtcc tacacatacg | 2220 |
| caagcaattt aattgtgttt aataagttgt taaaacatgt tttggttgta ttttggattc | 2280 |
| ctagtgtagt ttcggtgatc aatgccgtct actttagtgt gttctacttc cctttattt | 2340 |
| tgtttctttt ttactttttc cttaactata ttgtaggaaa aaaaaaatcc tttatcaagc | 2400 |
| atttatcaag aacggagttt gcttttaat tttcccttca taacattcca tcagaattca | 2460 |
| gttttgcttt tgcttctaaa ttacgttcaa atcagggatg ataatcggtt aggtaatata | 2520 |
| tacagtaccc cttgcatagt cacgtttgaa aaatataatc atacttagtt cggtaacaat | 2580 |
| ttaaattatc attctcgtaa tcattagcta cttatgcact catatccgta tccgctactt | 2640 |
| gctcttgtcg taagtcaata aattaatata aaaaaatact taaaacttgt tacaactaaa | 2700 |
| ttaaaaattt attttaaat cattcaagca ccagtcagca tcatcacacc aaaagttagg | 2760 |
| cccgaatagt ttgaaattag aaagctcgca attgaggtct acaggccaaa ttcgctctta | 2820 |
| gccgtacaat attactcacc ggatcctaac cggtgtgatc atgggccgcg attaaaaatc | 2880 |
| tcaattatat ttggtctaat ttagtttggt attgagtaaa acaaattcga accaaaccaa | 2940 |
| aatataaata tatagttttt atatatatgc ctttaagact ttttatagaa ttttctttaa | 3000 |
| aaaatatcta gaaatatttg cgactcttct ggcatgtaat atttcgttaa atatgaagtg | 3060 |
| ctccattttt attaaccttta aataattggt tgtacgatca cttttcttatc aagtgttact | 3120 |

```
aaaatgcgtc aatctctttg ttcttccata ttcatatgtc aaaacctatc aaaattctta   3180
tatatctttt tcgaatttga agtgaaattt cgataattta aaattaaata gaacatatca   3240
ttatttaggt atcatattga tttttatact taattactaa atttggttaa ctttgaaagt   3300
gtacatcaac gaaaaattag tcaaacgact aaaataaata aatatcatgt gttattaaga   3360
aaattctcct ataagaatat tttaatagat catatgtttg taaaaaaaat taatttttac   3420
taacacatat atttacttat caaaaatttg acaaagtaag attaaaataa tattcatcta   3480
acaaaaaaaa aaccagaaaa tgctgaaaac ccggcaaaac cgaaccaatc caaaccgata   3540
tagttggttt ggtttgattt tgatataaac cgaaccaact cggtccattt gcacccctaa   3600
tcataatagc tttaatattt caagatatta ttaagttaac gttgtcaata tcctggaaat   3660
tttgcaaaat gaatcaagcc tatatggctg taatatgaat ttaaaagcag ctcgatgtgg   3720
tggtaatatg taatttactt gattctaaaa aaatatccca agtattaata atttctgcta   3780
ggaagaaggt tagctacgat ttacagcaaa gccagaatac aatgaaccat aaagtgattg   3840
aagctcgaaa tatacgaagg aacaaatatt tttaaaaaaa tacgcaatga cttggaacaa   3900
aagaaagtga tatatttttt gttcttaaac aagcatcccc tctaaagaat ggcagttttc   3960
ctttgcatgt aactattatg ctcccttcgt tacaaaaatt ttggactact attgggaact   4020
tcttctgaaa atagtggcca ccgcttaatt aaggcgcgcc atgcccgggc aagcggccgc   4080
acaagtttgt acaaaaaagc aggctccgcg gtgactgact gaaaagcttg tcgacctgca   4140
ggtcaacgga tcaggatatt cttgtttaag atgttgaact ctatggaggt ttgtatgaac   4200
tgatgatcta ggaccggata agttcccttc ttcatagcga acttattcaa agaatgtttt   4260
gtgtatcatt cttgttacat tgttattaat gaaaaaatat tattggtcat tggactgaac   4320
acgagtgtta aatatggacc aggcccccaaa taagatccat tgatatatga attaaataac   4380
aagaataaat cgagtcacca aaccacttgc cttttttaac gagacttgtt caccaacttg   4440
atacaaaagt cattatccta tgcaaatcaa taatcataca aaaatatcca ataacactaa   4500
aaaattaaaa gaaatggata atttcacaat atgttatacg ataaagaagt tacttttcca   4560
agaaattcac tgattttata agcccacttg cattagataa atggcaaaaa aaaacaaaaa   4620
ggaaaagaaa taaagcacga agaattctag aaaatacgaa atacgcttca atgcagtggg   4680
acccacggtt caattattgc caattttcag ctccaccgta tatttaaaaa ataaaacgat   4740
aatgctaaaa aaatataaat cgtaacgatc gttaaatctc aacggctgga tcttatgacg   4800
accgttagaa attgtggttg tcgacgagtc agtaataaac ggcgtcaaag tggttgcagc   4860
cggcacacac gagtcgtgtt tatcaactca aagcacaaat acttttcctc aacctaaaaa   4920
taaggcaatt agccaaaaac aactttgcgt gtaaacaacg ctcaatacac gtgtcatttt   4980
attattagct attgcttcac cgccttagct ttctcgtgac ctagtcgtcc tcgtcttttc   5040
ttcttcttct tctataaaac aatacccaaa gcttcttctt cacaattcag atttcaattt   5100
ctcaaaatct taaaaacttt ctctcaattc tctctaccgt gatcaaggta aatttctgtg   5160
ttccttattc tctcaaaatc ttcgattttg ttttcgttcg atcccaattt cgtatatgtt   5220
ctttggttta gattctgtta atcttagatc gaagacgatt ttctgggttt gatcgttaga   5280
tatcatctta attctcgatt agggtttcat aaatatcatc cgatttgttc aaataatttg   5340
agttttgtcg aataattact cttcgatttg tgatttctat ctagatctgg tgttagtttc   5400
tagtttgtgc gatcgaattt gtcgattaat ctgagttttt ctgattaaca gagatctcca   5460
```

```
tggctcagac cactctccaa atcacaccca ctggtgccac cttgggtgcc acagtcactg   5520
gtgttcacct tgccacactt gacgatgctg gtttcgctgc cctccatgca gcctggcttc   5580
aacatgcact cttgatcttc cctgggcaac acctcagcaa tgaccaacag attacctttg   5640
ctaaacgctt tggagcaatt gagaggattg gcggaggtga cattgttgcc atatccaatg   5700
tcaaggcaga tggcacagtg cgccagcact ctcctgctga gtgggatgac atgatgaagg   5760
tcattgtggg caacatggcc tggcacgccg actcaaccta catgccagtc atggctcaag   5820
gagctgtgtt cagcgcagaa gttgtcccag cagttggggg cagaacctgc tttgctgaca   5880
tgagggcagc ctacgatgcc cttgatgagg caacccgtgc tcttgttcac caaaggtctg   5940
ctcgtcactc ccttgtgtat tctcagagca agttgggaca tgtccaacag gccgggtcag   6000
cctacatagg ttatggcatg gacaccactg caactcctct cagaccattg gtcaaggtgc   6060
atcctgagac tggaaggccc agcctcttga tcggccgcca tgcccatgcc atccctggca   6120
tggatgcagc tgaatcagag cgcttccttg aaggacttgt tgactgggcc tgccaggctc   6180
ccagagtcca tgctcaccaa tgggctgctg agatgtggt tgtgtgggac aaccgctgtt   6240
tgctccaccg tgctgagccc tgggatttca gttgccacg tgtgatgtgg cactccagac   6300
tcgctggacg cccagaaact gagggtgctg ccttggtttg agtagttagc ttaatcacct   6360
agagctcggt caccagcata attttatta atgtactaaa ttactgtttt gttaaatgca   6420 atttgcttt ctcgggattt aatatcaaa atctatttag aaatacacaa tattttgttg   6480
caggcttgct ggagaatcga tctgctatca taaaaattac aaaaaaattt tatttgcctc   6540
aattatttta ggattggtat taaggacgct taaattattt gtcgggtcac tacgcatcat   6600
tgtgattgag aagatcagcg atacgaaata ttcgtagtac tatcgataat ttatttgaaa   6660
attcataaga aaagcaaacg ttacatgaat tgatgaaaca atacaaagac agataaagcc   6720
acgcacattt aggatattgg ccgagattac tgaatattga gtaagatcac ggaatttctg   6780
acaggagcat gtcttcaatt cagcccaaat ggcagttgaa atactcaaac cgccccatat   6840
gcaggagcgg atcattcatt gtttgtttgg ttgcctttgc caacatggga gtccaaggtt   6900
gcggccgcgc gccgacccag cttcttgta caaagtggtt gcggccgctt aattaaattt   6960
aaatgcccgg gcgtttaaac gcggccgctt aattaaggcc ggcctgcagc aaacccagaa   7020
ggtaattatc caagatgtag catcaagaat ccaatgttta cgggaaaaac tatggaagta   7080
ttatgtaagc tcagcaagaa gcagatcaat atgcggcaca tatgcaacct atgttcaaaa   7140
atgaagaatg tacagataca agatcctata ctgccagaat acgaagaaga atacgtagaa   7200
attgaaaaag aagaaccagg cgaagaaaag aatcttgaag acgtaagcac tgacgacaac   7260
aatgaaaaga agaagataag gtcggtgatt gtgaaagaga catagaggac acatgtaagg   7320
tggaaaatgt aagggcggaa agtaaaccta tcacaaagga atcttatccc ccactactta   7380
tccttttata ttttttccgtg tcattttgc ccttgagttt tcctatataa ggaaccaagt   7440 tcggcattg tgaaaacaag aaaaaatttg tgtaagcta ttttctttga agtactgagg   7500
atacaacttc agagaaattt gtaagtttgt agatctccat gtctccggag aggagaccag   7560
ttgagattag gccagctaca gcagctgata tggccgcgt tgtgatatc gttaaccatt   7620 acattgagac gtctacagtg aactttagga cagagccaca aacaccacaa gagtggattg   7680
```

```
atgatctaga gaggttgcaa gatagatacc cttggttggt tgctgaggtt gagggtgttg    7740
tggctggtat tgcttacgct gggccctgga aggctaggaa cgcttacgat tggacagttg    7800
agagtactgt ttacgtgtca cataggcatc aaaggttggg cctaggatcc acattgtaca    7860
cacatttgct taagtctatg gaggcgcaag gttttaagtc tgtggttgct gttataggcc    7920
ttccaaacga tccatctgtt aggttgcatg aggctttggg atacacagcc cggggtacat    7980
tgcgcgcagc tggatacaag catggtggat ggcatgatgt tggttttggg caaagggatt    8040
ttgagttgcc agctcctcca aggccagtta ggccagttac ccagatctga ggtaccctga    8100
gcttgagctt atgagcttat gagcttagag ctcggatcca ctagtaacgg ccgccagtgt    8160
gctggaattc gcccttgact agataggcgc ccagatcggc ggcaatagct tcttagcgcc    8220
atcccgggtt gatcctatct gtgttgaaat agttgcggtg ggcaaggctc tctttcagaa    8280
agacaggcgg ccaaaggaac ccaaggtgag gtgggctatg gctctcagtt ccttgtggaa    8340
gcgcttggtc taaggtgcag aggtgttagc gggatgaagc aaaagtgtcc gattgtaaca    8400
agatatgttg atcctacgta aggatattaa agtatgtatt catcactaat ataatcagtg    8460
tattccaata tgtactacga tttccaatgt ctttattgtc gccgtatgta atcggcgtca    8520
caaaataatc cccggtgact ttcttttaat ccaggatgaa ataatatgtt attataattt    8580
ttgcgatttg gtccgttata ggaattgaag tgtgcttgcg gtcgccacca ctcccatttc    8640
ataattttac atgtatttga aaataaaaa tttatggtat tcaatttaaa cacgtatact    8700
tgtaaagaat gatatcttga agaaatata gtttaaatat ttattgataa aataacaagt    8760
caggtattat agtccaagca aaaacataaa tttattgatg caagttttaaa ttcagaaata    8820 tttcaataac tgattatatc agctggtaca ttgccgtaga tgaaagactg agtgcgatat    8880
tatggtgtaa tacatagcgg ccgggtttct agtcaccggt taggatccgt ttaaactcga    8940
ggctagcgca tgcacataga cacacacatc atctcattga tgcttggtaa taattgtcat    9000
tagattgttt ttatgcatag atgcactcga aatcagccaa ttttagacaa gtatcaaacg    9060
gatgtgactt cagtacatta aaaacgtccg caatgtgtta ttaagttgtc taagcgtcaa    9120 tatttaatt cttaacaatc aatatttaa ttcttaaact ttattaaatc taacaataaa    9180
ctgtaagaac taattcttaa acttcaataa acaatactgc gttttagtaa ttaaattaat    9240
aatatataga tatagatata taatttgtca acatattctt acctattttt ccattgaaat    9300
atgttagcaa gttcaaaaaa agttttgaca aaaaactcta ctatcttttg tttcatttac    9360
tttatgtgag ggataataa gtaatataac atttagttta tttaaagaaa ataaaaaagt    9420
taatttctct ttctgccact gatactctat ggtggagaga tccgatgcag tggtggagcc    9480
tggcctcgac acataagtgt gacgacgcag ctgttgaaga gatctgattc gacggtgggg    9540
taatgcatgg tggttgacag gttgatgggt ggagaagacg taattgctac cgccgtcaac    9600
ggaggaagga gcaaagatgt ctcgtatgtg aaaattatgc ggttgagatg ccgtttcatt    9660
ccctttaaaa aaatcccttg atggttgcaa tgcaaattaa aaattgaaaa ataattaat    9720 tgttcaaatt aaagatttag catgaaaaaa aaaacactta attgtgccca tgactccatg    9780
acctgcgtaa cttgggaagg aaaggaattt ttttgctaaa ggaaggcatg ggaagatgag    9840
agaggagaga gaatcagtgg aagtgagaga aattaacttt tgtttttta aaaactaaat    9900 attatattac tattatatat atatatatat atatataaaa gatttttag ctggattctt    9960 gatataaaaa atttctcacc atattttatta ttatatattt ttttgagat ctcaaaaaag   10020 gaagttggat ttcttctcaa taactctaaa aaattattcc tatttcaaaa aatatttttt   10080
```

```
atgtctttct ctaattgatg aataatatct atttaagtat attttattgt gaaatccaca  10140
aaagtgactg ataaatctaa tttaggatct accattagag aaaaataaat aaattcttat  10200
attatatgtg at                                                      10212
```